US010889845B2

(12) United States Patent
Rahman et al.

(10) Patent No.: US 10,889,845 B2
(45) Date of Patent: Jan. 12, 2021

(54) PRODUCTION OF N-GLYCOPROTEINS FOR ENZYME ASSISTED GLYCOMODIFICATION

(71) Applicants: UNIVERSITY OF COPENHAGEN, Copenhagen K (DK); DANMARKS TEKNISKE UNIVERSITET, Kgs. Lyngby (DK)

(72) Inventors: Shamim Herbert Rahman, Valby (DK); Carsten Behrens, Copenhagen N (DK); Malene Bech Vester-Christensen, Vedbæk (DK); Henrik Clausen, Holte (DK); Zhang Yang, Vanløse (DK); Adnan Fevzi Halim, Malmö (SE); Eric Bennett, Kgs. Lyngby (DK)

(73) Assignees: UNIVERSITY OF COPENHAGEN, Copenhagen (DK); DANMARKS TEKNISKE UNIVERSITET, Kgs. Lyngby (DK)

( * ) Notice: Subject to any disclaimer, the term of this patent is extended or adjusted under 35 U.S.C. 154(b) by 0 days.

(21) Appl. No.: 15/745,300

(22) PCT Filed: Jun. 15, 2016

(86) PCT No.: PCT/EP2016/063753
§ 371 (c)(1),
(2) Date: Jan. 16, 2018

(87) PCT Pub. No.: WO2017/008982
PCT Pub. Date: Jan. 19, 2017

(65) Prior Publication Data
US 2019/0203247 A1    Jul. 4, 2019

Related U.S. Application Data

(60) Provisional application No. 62/193,433, filed on Jul. 16, 2015.

(51) Int. Cl.
| A61K 48/00 | (2006.01) |
| C07H 21/04 | (2006.01) |
| C12P 21/00 | (2006.01) |
| C07K 14/505 | (2006.01) |
| C07K 14/61 | (2006.01) |
| C07K 16/00 | (2006.01) |
| C12N 15/90 | (2006.01) |
| C12N 9/64 | (2006.01) |
| C12N 5/00 | (2006.01) |
| C12N 5/071 | (2010.01) |

(52) U.S. Cl.
CPC .......... *C12P 21/005* (2013.01); *C07K 14/505* (2013.01); *C07K 14/61* (2013.01); *C07K 16/00* (2013.01); *C12N 5/00* (2013.01); *C12N 5/0682* (2013.01); *C12N 9/6437* (2013.01); *C12N 15/907* (2013.01); *C07H 21/04* (2013.01); *C07K 2317/41* (2013.01); *C12N 2501/724* (2013.01); *C12N 2510/02* (2013.01)

(58) Field of Classification Search
CPC ..... C12N 15/85; C12N 2510/00; C07H 21/04
USPC ...................................... 424/93.21; 536/23.5
See application file for complete search history.

(56) References Cited

U.S. PATENT DOCUMENTS

2010/0074888 A1    3/2010  Aragane

FOREIGN PATENT DOCUMENTS

| WO | WO 2015/134488 | 9/2015 |
| WO | WO 2016/091268 | 6/2016 |

OTHER PUBLICATIONS

Lin et al., 2016, US 20160369240 A1, effective filing date, Mar. 4, 2014.*
Zhang et al., "Engineered CHO cells for Production of Diverse, Homogeneous Glycoproteins," Nature Biotechnology, vol. 33, No. 8, pp. 842-844, Aug. 2015.
University of Copenhagen, Notification of Transmittal of the International Search Report and the Written Opinion of the International Search Authority for PCT/EP2016/063753, dated Nov. 11, 2016, 16 pages.

* cited by examiner

*Primary Examiner* — Shin Lin Chen
(74) *Attorney, Agent, or Firm* — Knobbe, Martens, Olson & Bear, LLP

(57) ABSTRACT

The present invention relates to a cell comprising a gene encoding a polypeptide of interest, wherein the polypeptide of interest is expressed comprising one or more posttranslational modification patterns. These modifications are useful for example in improvement of pharmacokinetic properties, i.e. by attaching PEG chains to proteins. The present invention also relates to methods for producing the antibodies and compositions comprising the antibodies, and their uses.

5 Claims, 35 Drawing Sheets
Specification includes a Sequence Listing.

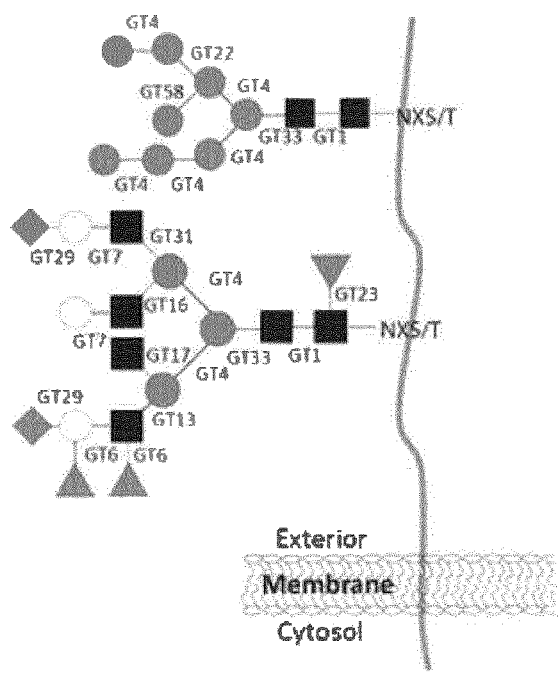
B. N-glycan
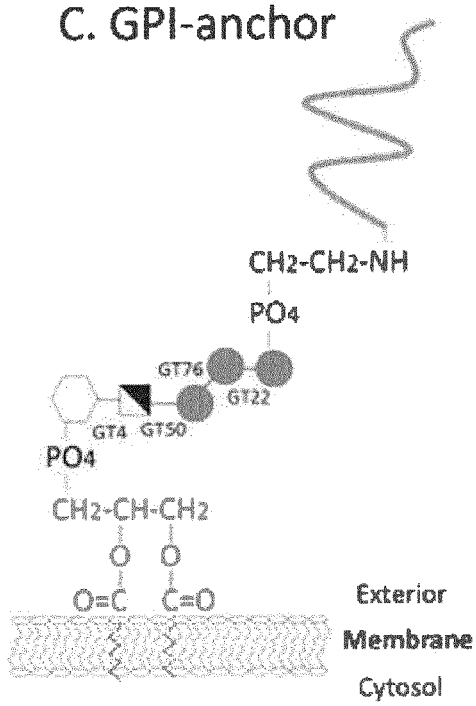
C. GPI-anchor
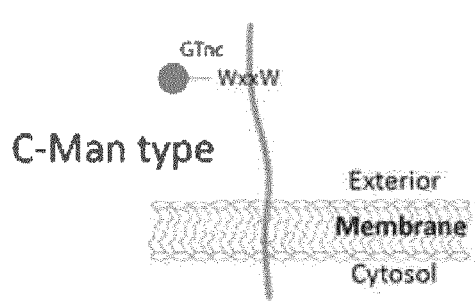
D. C-glycan
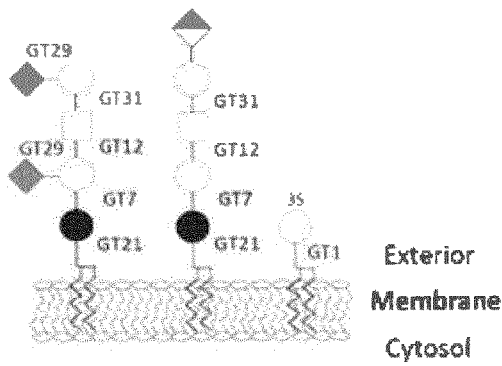
E. Glycosphingolipids
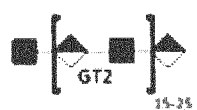
F. Hyaluronan
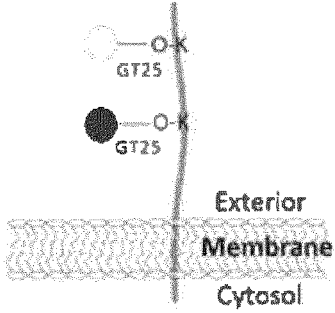
G. HO-Lysine glycan/O-Gal
Fig. 1B-G O-GalNAc
Core 1, only short structures are synthezised
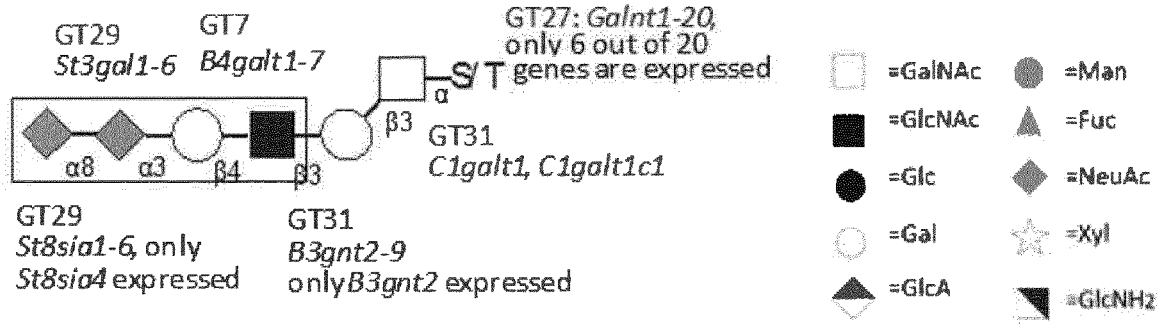
Core 2, missing in CHO-GS/K1
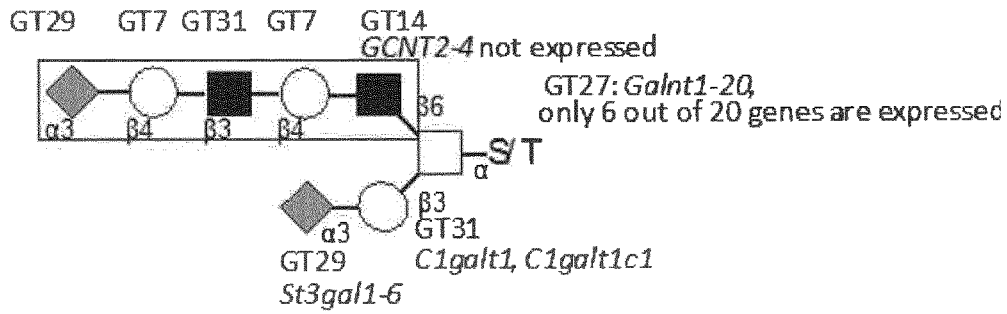
Core 3, missing in CHO-GS/K1
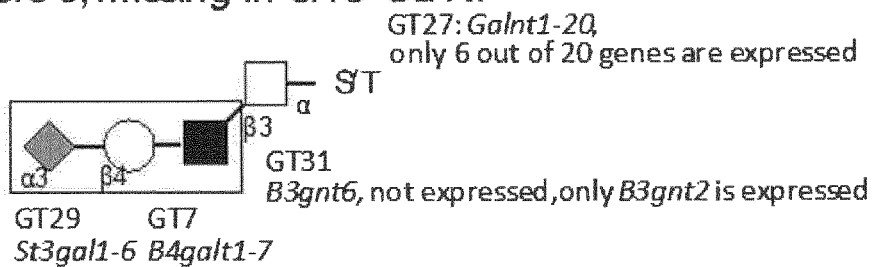
Core 4, missing in CHO-GS/K1
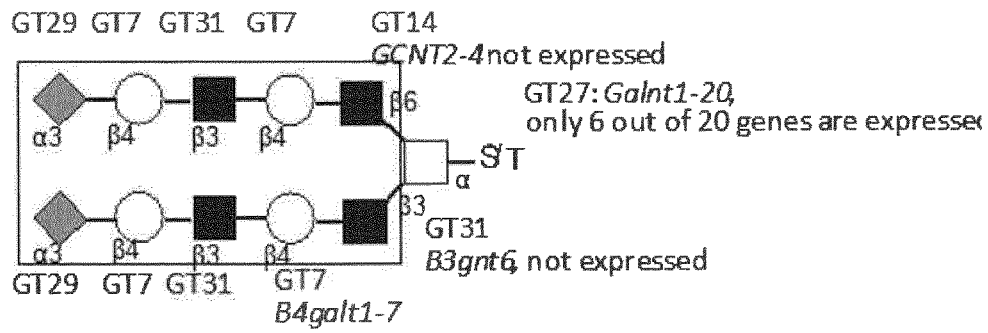
Fig. 2A1

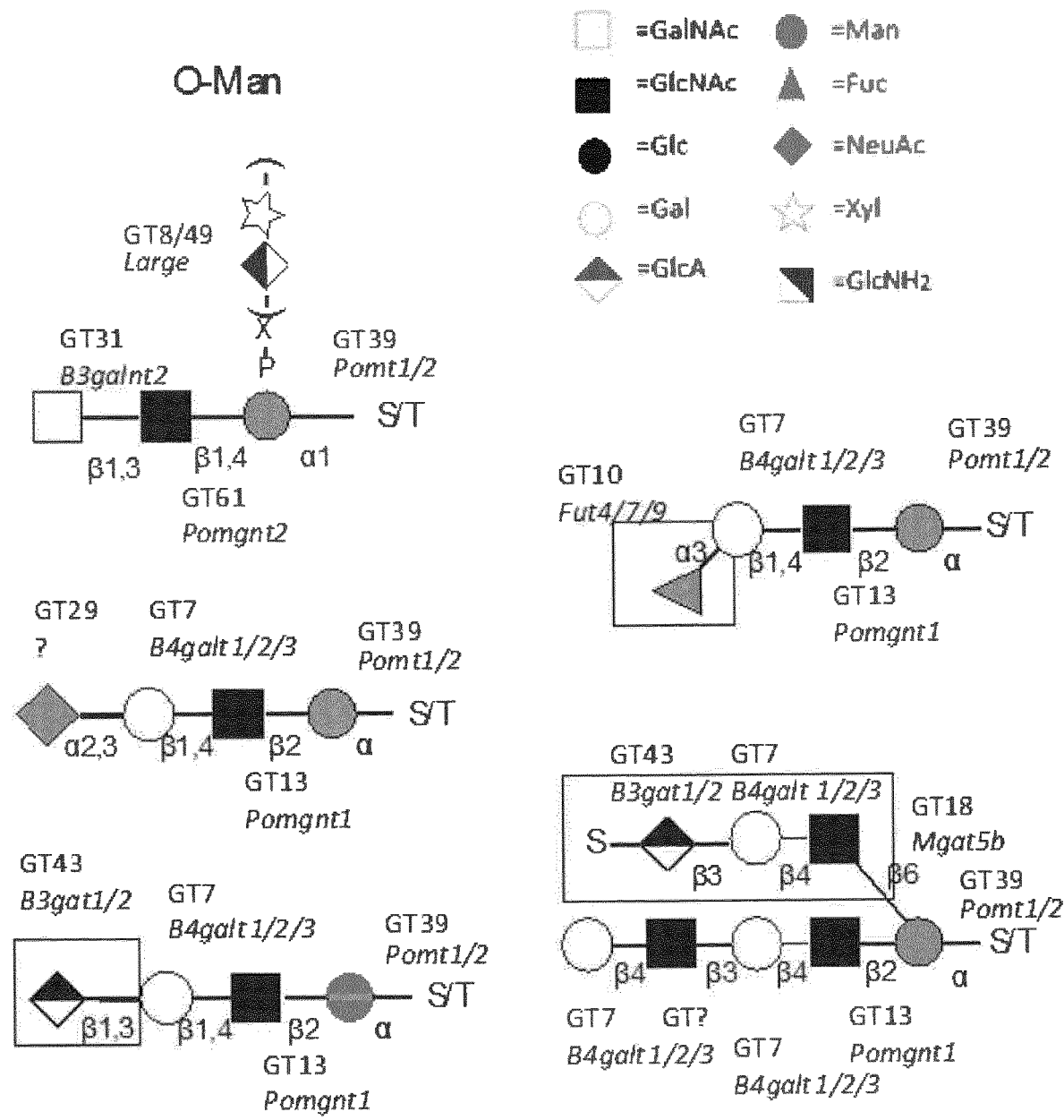
Fig. 2A2

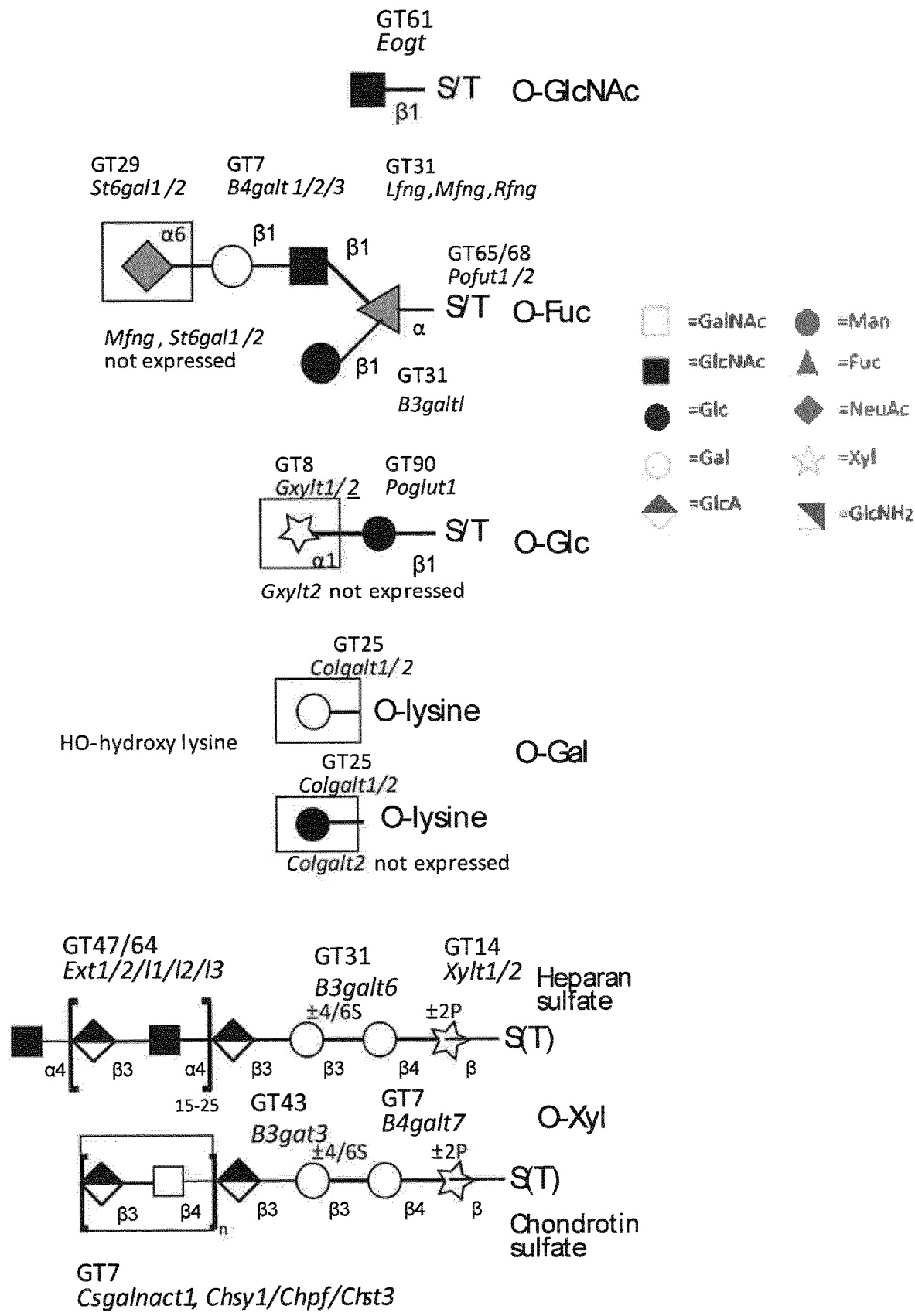
Fig. 2A3

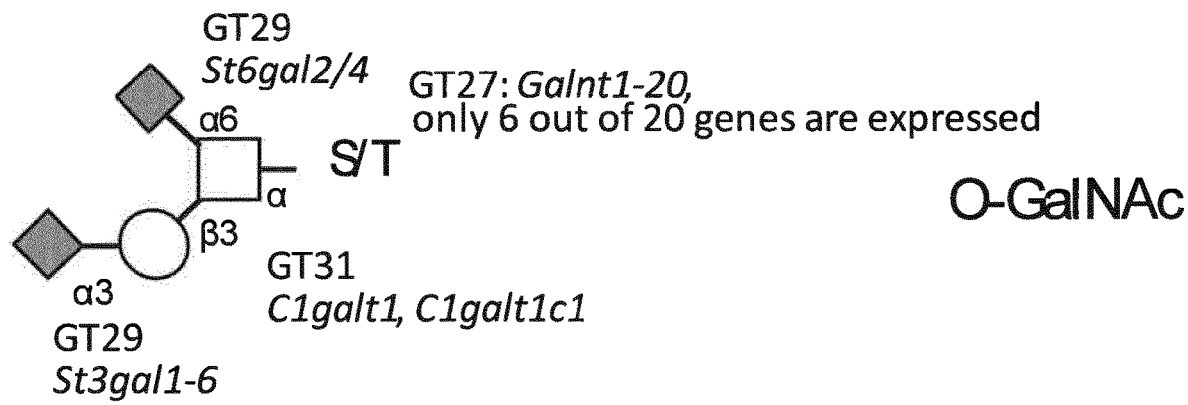
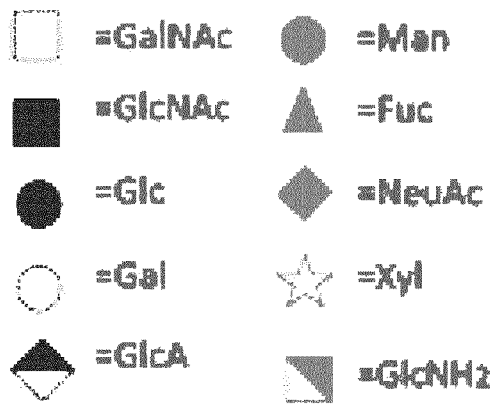
Fig. 2A4

D C-glycan
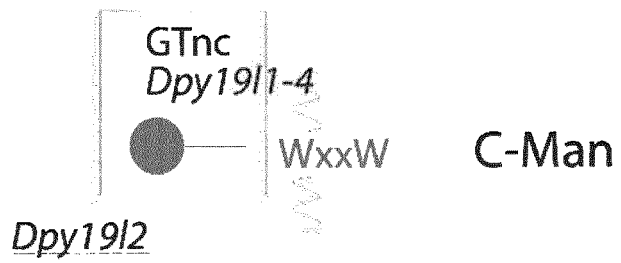
E
GPI-anchor
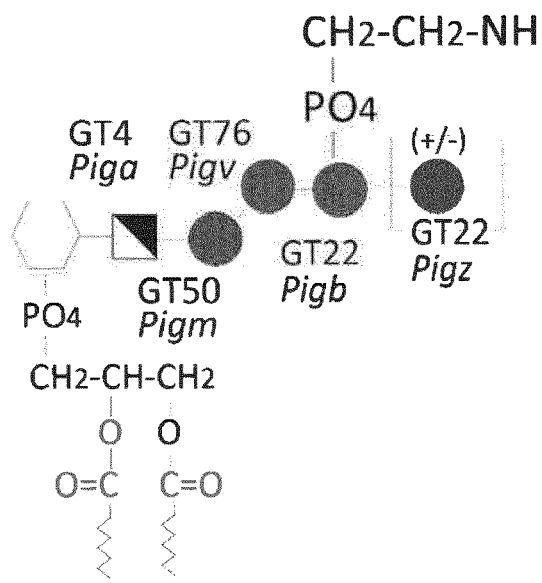
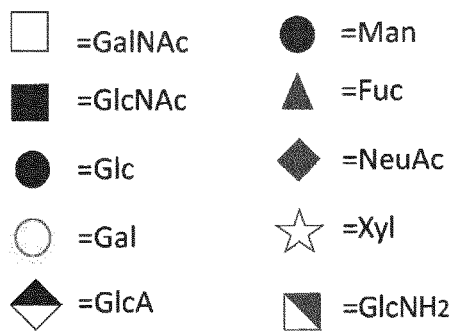
Fig. 2D-E

A

B

PRODUCTION OF N-GLYCOPROTEINS FOR ENZYME ASSISTED GLYCOMODIFICATION

TECHNICAL FIELD OF THE INVENTION

The present invention relates to a cell comprising a gene encoding a polypeptide of interest, wherein the polypeptide of interest is expressed comprising one or more posttranslational modification patterns. These modifications are useful for example in improvement of pharmacokinetic properties, i.e. by attaching PEG or HEP chains to proteins. The present invention also relates to methods for producing glycoproteins and compositions comprising the glycoproteins, and their uses.

BACKGROUND OF THE INVENTION

Glycoprotein biologics is the fastest growing class of therapeutics, and most of these can only be produced recombinantly in mammalian cells with capacity for human-like glycosylation. The Chinese hamster ovary (CHO) cell has gained a leading role as host cell for recombinant production of glycoprotein therapeutics mainly because it produces rather simple N-glycans with branching and capping similar to what is produced in some human cells.

Notably, CHO produce complex-type heterogenous N-glycans with bi-, tri-, and tetraantennary structures with core α6Fucose (Fuc), a minor amount of poly-N-Acetyllactosamine (poly-LacNAc) mainly on the α1,6 arm of tetraantennary structures, and exclusive capping of LacNAc with α2,3 linked neuraminic acid (NeuAc).

CHO does not generally produce the non-human and in man immunogenic capping structures, such as N-glycolylneuraminic acid (NeuGc) or α3Gal, although the occurrence of these have been reported perhaps as a result of gene induction. N-glycosylation may vary for different proteins as well as for different glycosites in individual proteins, and e.g. IgG antibodies are produced with truncated N-glycan structures at the conserved Asn297 glycosite (biantennary structures with core α6Fuc, limited LacNAc, and NeuAc capping).

A major concern with CHO is the substantial heterogeneity in N-glycan processing, which can be difficult to control during bioprocessing and can pose issues for bioactivity as well as biosafety.

Thus, a major activity in bioprocessing of therapeutics is devoted to glycan analysis and control of fermentation to achieve consistency.

Substantial efforts in the last two decades have been devoted to genetic glycoengineering of CHO cells with the aims to expand the capacity for glycosylation, reduce heterogeneity, and improve or alter especially sialylation.

These studies have essentially all used random integration of cDNAs encoding glycosyltransferases and experienced problems with stability, consistency, and predictability of the introduced glycosylation capacity. The major obstacle has been the need to rely on overexpression of glycosyltransferases and competition with the endogenous expressed enzymes because of lack of simple methods to knock these out in cell lines.

Thus, only very few such glycoengineered CHO cells have not reached production of clinical therapeutics. One successful glycoengineering strategy has, however, emerged after the discovery that IgGs without core α6Fuc on the Asn297 N-glycan exhibits markedly higher Antibody-Dependent Cell Cytotoxicity (ADCC).

Thus, using two rounds of homologous recombination both alleles of the fut8 gene encoding the α6fucosyltransferase controlling core fucosylation was knocked out in CHO, and at least one therapeutic IgG produced in CHO without the fut8 gene is now in clinical use.

More recently, the fut8 gene was knocked out using precise gene editing with Zinc finger nuclease (ZFN) gene targeting with a fraction of time and resources spent.

The emergence of precise gene editing technologies for knockout (KO) and knockin (KI) have opened up for an entirely different level of speed and ease with which stable genetic manipulation of host cell lines to remove and introduce glycosyltransferase genes can be achieved, and this will undoubtedly impact engineering of mammalian host cell factories for recombinant production of therapeutics.

Thus, there is a need for mammalian, and especially CHO cells, that have specific glycosylation patterns with or without sialylation.

SUMMARY OF THE INVENTION

The present invention relates to a cell comprising a gene encoding a polypeptide of interest, wherein the polypeptide of interest is expressed comprising one or more posttranslational modification patterns.

One object of the present invention relates to a cell comprising one or more glycosyltransferase genes that have been inactivated, and that has new and/or more homogeneous stable glycosylation capacities, wherein mgat2 has been knocked out (KO), and with and without KO of mgat4A and/or mgat4B and/or mgat5 allowing production of N-glycans with monoantennary structure.

Another object of the present invention relates to a cell comprising one or more glycosyltransferase genes that have been inactivated, and that has new and/or more homogeneous stable glycosylation capacities, wherein mgat2 has been knocked out (KO), and with and without KO of mgat4A and/or mgat4B and/or mgat5 in combination with KO of sialyltransferases allowing production of N-glycans with monoantennary structure and without sialic acid capping.

Yet another object of the present invention relates to a cell comprising one or more glycosyltransferase genes that have been inactivated, and that has new and/or more homogeneous stable glycosylation capacities, wherein mgat2 has been knocked out (KO), and with and without KO of mgat4A and/or mgat4B and/or mgat5 in combination with KO of sialyltransferases and B3gnt2 allowing production N-glycans with monoantennary structure and without sialic acid capping and without poly-LacNAc.

In one embodiment of the present invention the cell is a mammalian cell or an insect cell.

In another embodiment of the present invention the cell is derived from Chinese hamster ovary or from human kidney.

In a further embodiment of the present invention the cell is selected from the group consisting of CHO, NS0, SP2/0, YB2/0, CHO-K1, CHO-DXB11, CHO-DG44, CHO-S, HEK293, HUVEC, HKB, PER-C6, NS0, or derivatives of any of these cells. In one embodiment of the present invention is the cell a CHO cell.

In another embodiment of the present invention the cell furthermore encodes an exogenous protein of interest.

In yet another embodiment of the present invention the protein of interest is an antibody, an antibody fragment, such as a Fab fragment, an Fc domain of an antibody, or a polypeptide.

In yet another embodiment of the present invention the protein of interest is a coagulation factor such as coagulation factor II (FII), coagulation factor V (FV), coagulation factor VII (FVIIa), coagulation factor VIII (FVIII), coagulation factor IX (FIX), coagulation factor X (FX), or coagulation factor XIII (FXIII).

One aspect of the present invention relates to a method for the production of di- and triPEGylated erythropoietin (EPO) glycoproteins, the method comprising the step of enzymatic glycoPEGylation of glycoengineered EPO variants.

Another aspect of the present invention relates to a method for the production of recombinant glycoproteins, comprising the step of generating a cell with specific glycosylation properties, wherein specific glycosylation property is the capacity for monoantennary N-glycan synthesis.

A further aspect of the present invention relates to a glycoprotein obtainable from a method according to the present invention.

In one embodiment of the present invention has the glycostructure outcome one or more of the following changes selected from the group consisting of simpler glycan structure, more homogeneous product, more sialic acids per molecule, non-sialylated, non-galactosylated, more homogeneous bi-antennary, more homogeneous monoantennary, more homogeneous triantennary, more homogeneous without poly-LacNAc, higher productivity in cell culture, new stable homogeneous glycosylation capacities, more human glycostructure, more homogeneous glycosylation and improved ADCC targeting of IgG, modified fucose level, no fucose, improved substrate for generating glycoconjugates.

One aspect of the present invention relates to a glycoprotein according to the present invention, which is a homogeneous glycoconjugate produced from a glycoprotein having a simplified glycan profile.

Another aspect of the present invention relates to a glycoprotein according to the present invention, which is a homogeneous glycoprotein conjugate comprising a polymer selected from, PEG, HEP, XTEN, PSA, HES.

A further aspect of the present invention relates to a glycoprotein according to the present invention, which is a homogeneous PEGylated protein conjugate produced from a protein variant according to the invention having a simplified glycan profile.

Another aspect of the present invention relates to a glycoprotein according to the present invention, which is a homogeneous PEGylated EPO conjugate produced from an EPO variant having a simplified glycan profile.

One aspect of the present invention relates to a glycoprotein according to the present invention, which is a simplified enzymatic glycoPEGylation process using glycoengineered EPO variants that provides high yield of di- and triPEGylated EPO forms.

Another aspect of the present invention relates to a glycoprotein according to the present invention, which is a protein conjugate according to the invention comprising FII, FV, FVIIa, FVIII, FIX, FX, FXIII, a Fab fragment of an antibody, or a Fc domain of an antibody.

A further aspect of the present invention relates to a glycoprotein according to the present invention, which is a protein-protein conjugate produced from a glycoprotein with a simplified glycan profile.

In one embodiment of the present invention is the glycoprotein according to the present invention a protein-protein conjugate produced from a glycoprotein with a simplified glycan profile comprising a Fab fragment and one of either FII, FV, FVIIa, FVIII, FIX, FX or FXIII.

In another embodiment of the present invention is the glycoprotein according to the present invention a protein-protein conjugate produced from a glycoprotein with a simplified glycan profile comprising a Fc Domain and one of either FII, FV, FVIIa, FVIII, FIX, FX or FXIII.

In a further embodiment of the present invention is the glycoprotein according to the present invention a homogeneous PEGylated EPO conjugate produced from an EPO variant having a simplified glycan profile.

One aspect of the present invention relates to the use of recombinant glycoproteins comprising monoantennary N-glycans for enzymatic modification of polypeptides.

BRIEF DESCRIPTION OF THE FIGURES

Unless specified differently all glycoprofiling analyses are performed with EPO expressed in CHO-GS cells engineered as indicated. Glycoprofiling Figures are MALDI-TOF spectra of PNGase F released permethylated N-glycans.

Figure 1A:
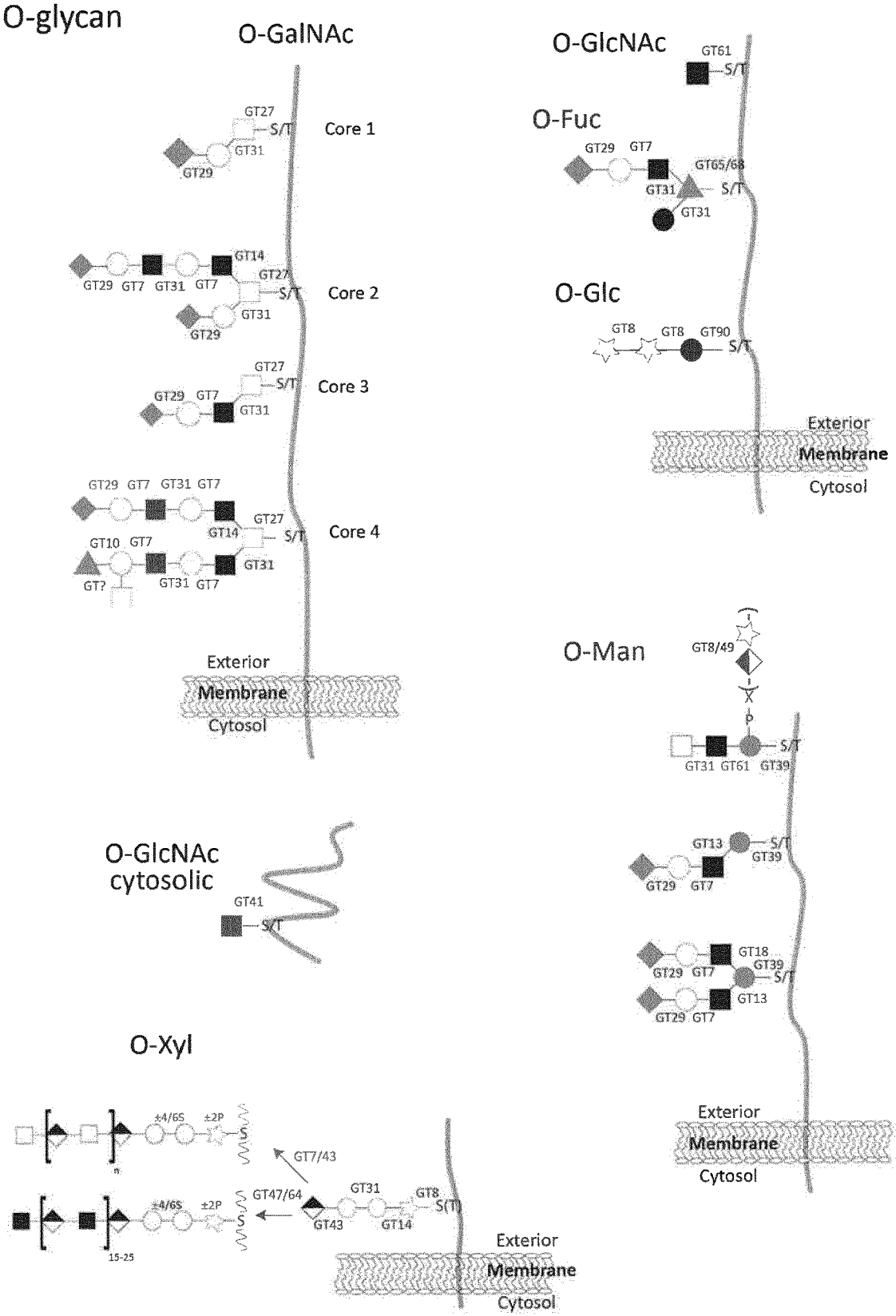
FIG. 1. A graphic depiction of the human CAZy GT families involved in the biosynthesis of the major mammalian glycoconjugates and their different glycosylaton pathways. The common mammalian glycan structures are depicted for (A) O-glycans including O-GalNAc, O-GlcNAc, O-Fuc, O-Glc, O-Man, O-Xyl; (B) N-glycans; (C) GPI-anchors; (D) C-glycans; (E) glycospingolipids; (F) hyaloronan and (G) hydroxy-lysine. Designations for monosaccharides according to the Consortium for Functional Glycomics are indicated (http://www.functionalglycomics.org).
Figure 2B:
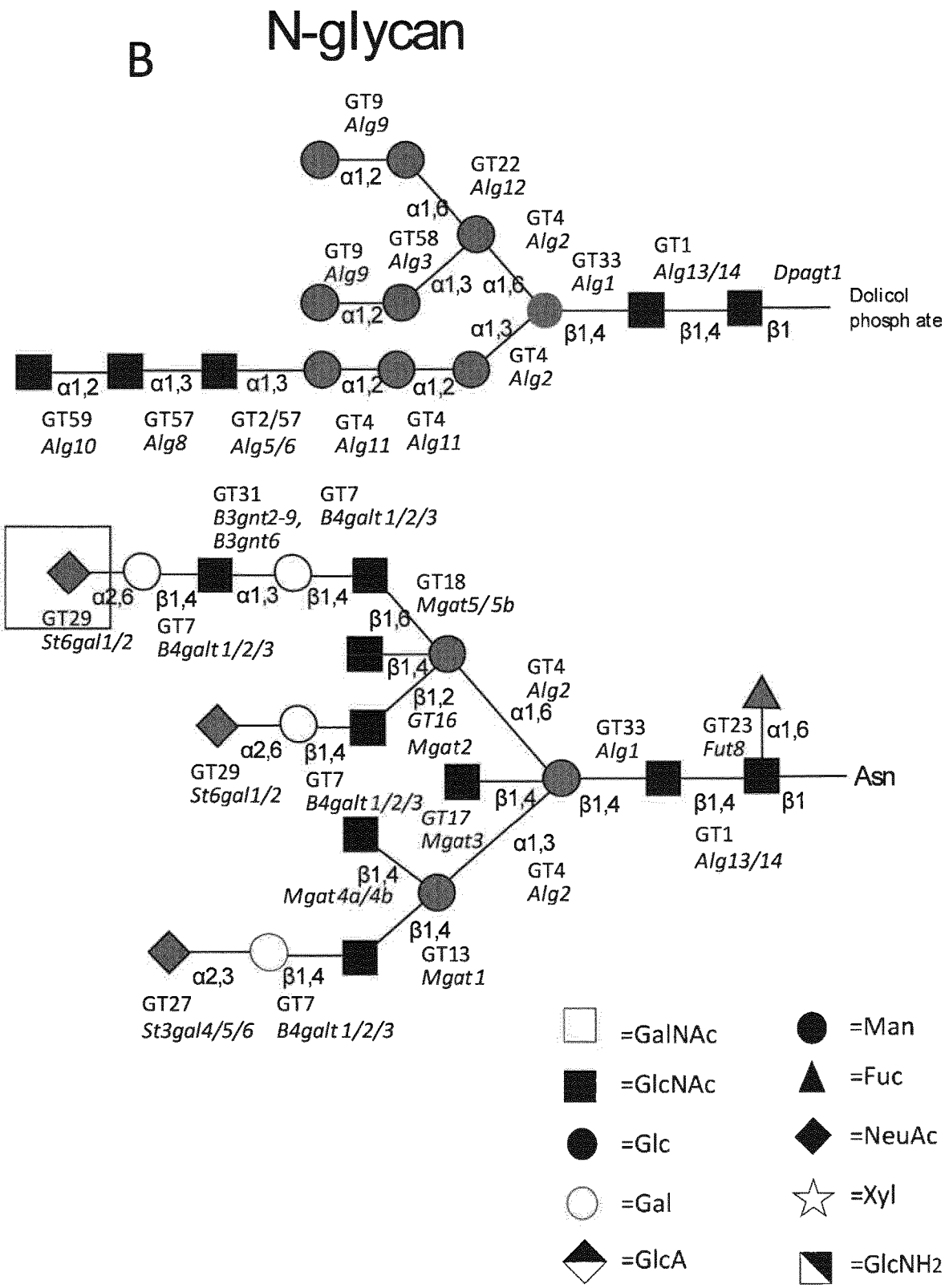
FIG. 2 A graphic representation of the different glycan structures and glycosylation pathways found in CHO cell lines with designations of glycosyltransferase genes expressed in CHO cell lines and their predicted role in biostynthic steps. The genes are assigned to the major confirmed or putative functions in the O-glycosylation (O-GalNAc, O-Fuc, O-Glc, O-GlcNAc, O-Xyl, and O-Man) and N-glycosylation pathways relevant for recombinant glycoprotein therapeutics today. (A) O-GalNAc glycosylation pathway with extended core 1, core 2, core 3, and core 4 structures; (B)N-glycosylation pathway; (C) glycosphingolipid biosynthetic pathways; (D)C-glycan, and (E) GPI-anchors. The CAZy families of glycosyltransferase (GT genes are notated and GT genes expressed in CHO cell lines are shown. Glycan structures not synthesized in CHO are boxed. Designations for monosaccharides according to the Consortium for Functional Glycomics are indicated.
Figure 2C:
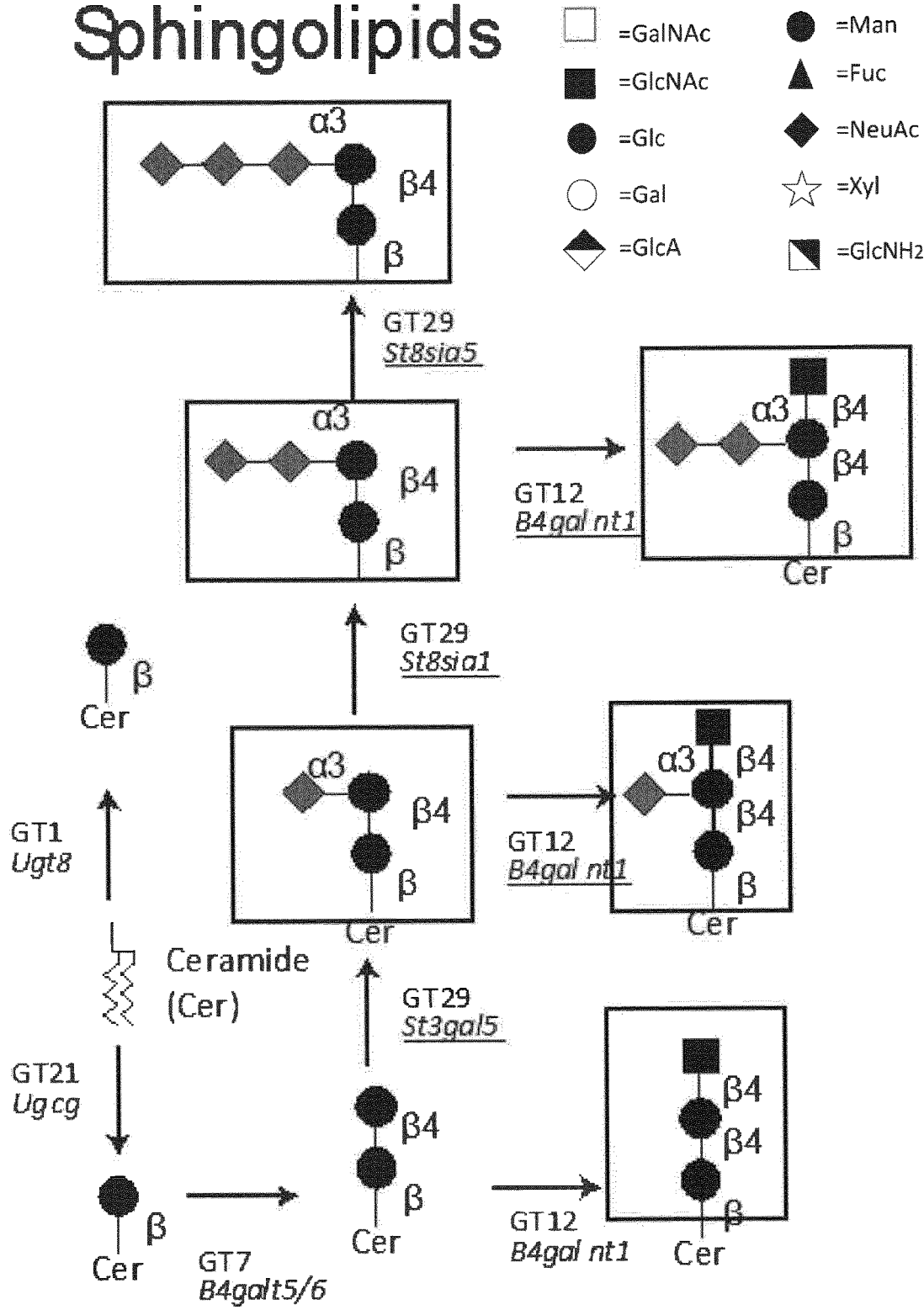
Figure 3A:
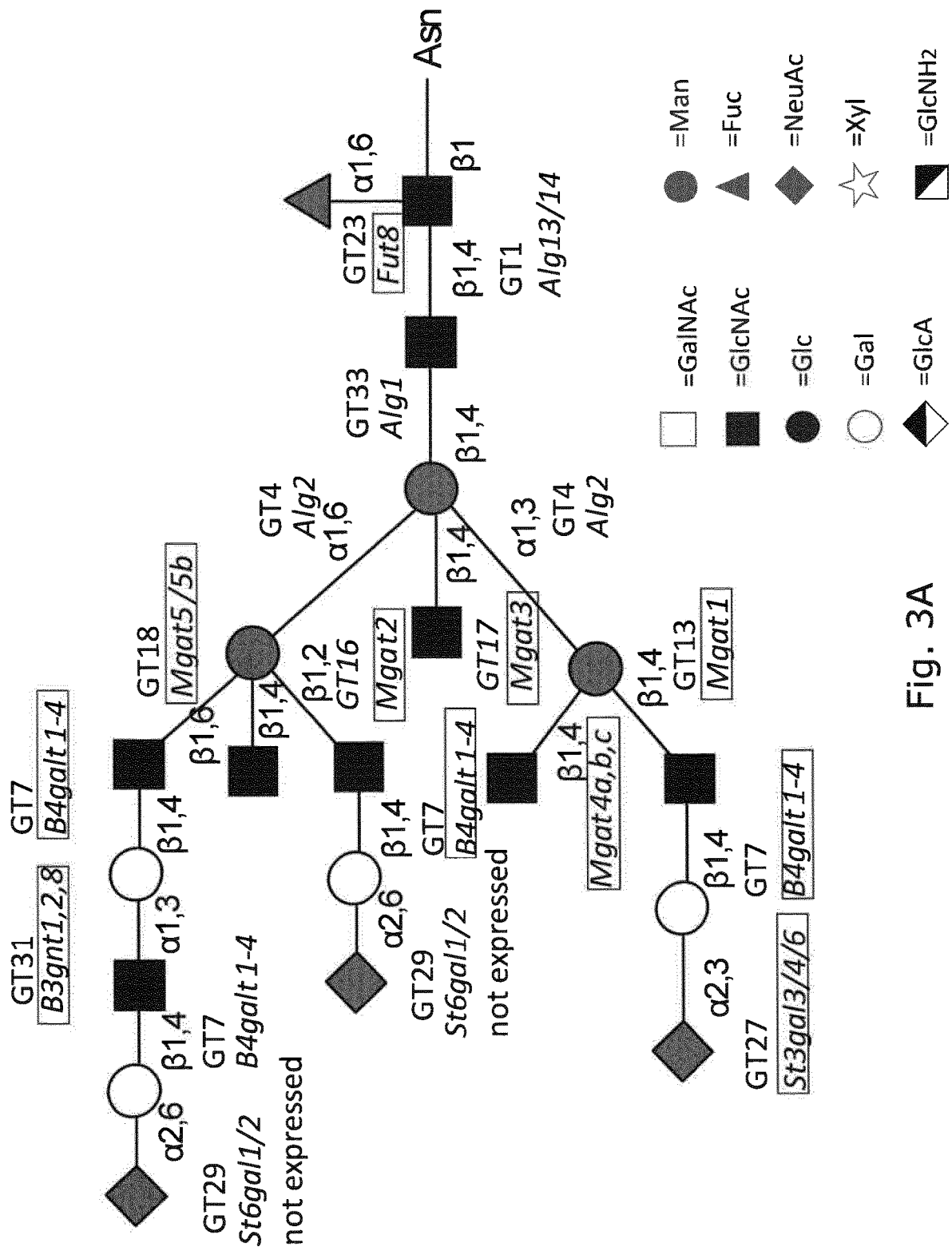
FIG. 3 Graphic depictions of all genes encoding isoenzymes with potential to regulate N-glycosylation branching, elongation, and terminal capping expressed in CHO. The depiction shows the knockout screen of glycosyltransferase genes involved in N-glycosylation in CHO using human EPO as recombinant expressed reporter glycoprotein. (A) The common tetraantennary N-glycan with poly-LacNAc on the β6-antenna and capping by sialic acids is shown, the knockout genes are boxed, and genes not expressed in the CHO cells are annotated. Note that human ST6Gal-I (ST6GAL1) has been introduced by ZFN-mediated knock-in. Designations for monosaccharides according to the Consortium for Functional Glycomics (CFG) are indicated. (B) Schematic depiction of the actual nuclease targeted regions relative to the predicted general domain structure of type II glycosyltransferase proteins (upper panel) and the targeted exon for each gene numbering the respective genes from first coding exon (lower panel). The exon structure depiction only includes the first targeted exons and does not include all exons for all genes.
Figure 3B:
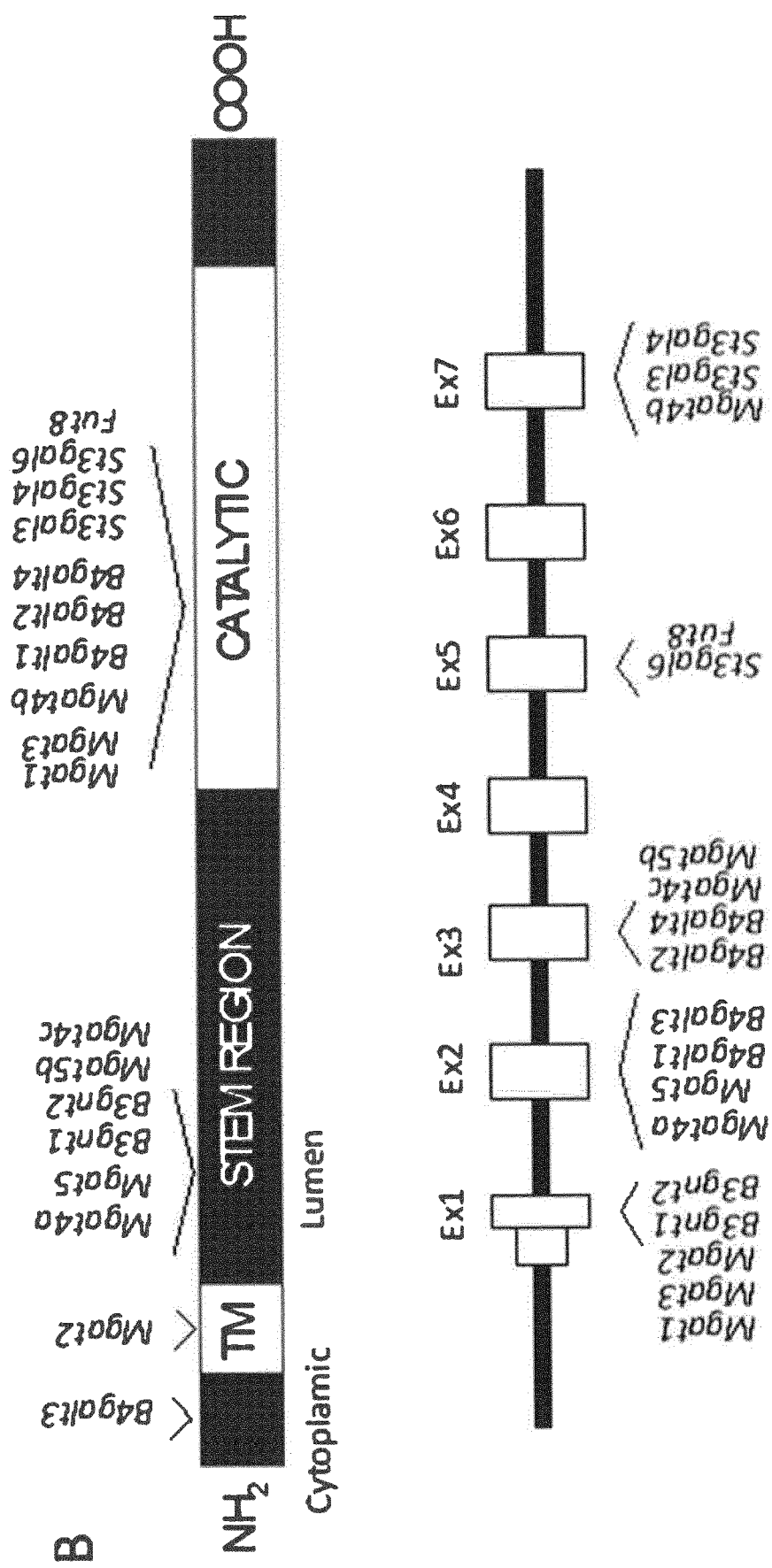
Figure 4:
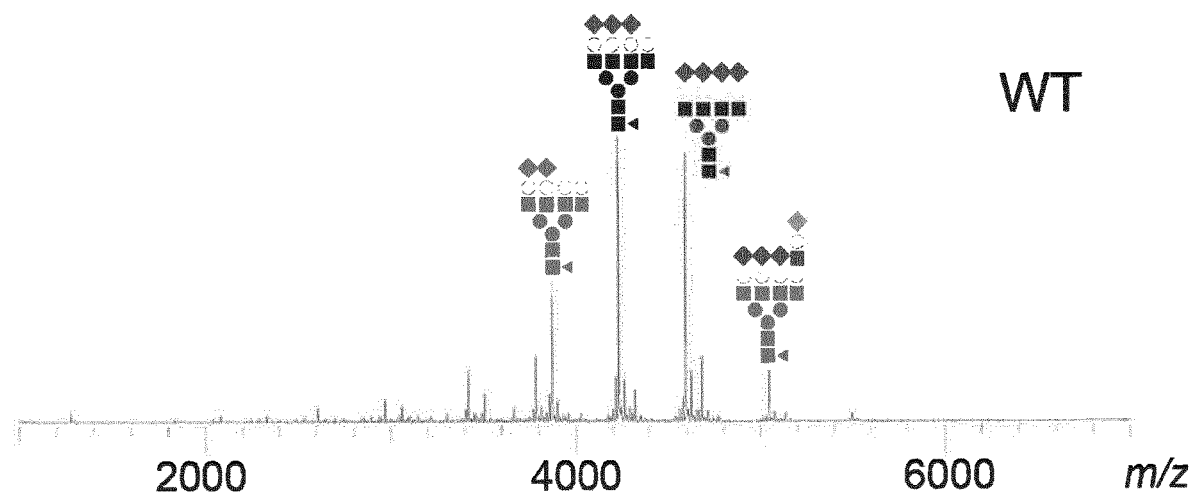
FIG. 4 Glycoprofiling of EPO expressed in CHO WT cells. MALDI-TOF spectra of PNGase F released permethylated N-glycans with predicted structures for the four major species.
Figure 5A:
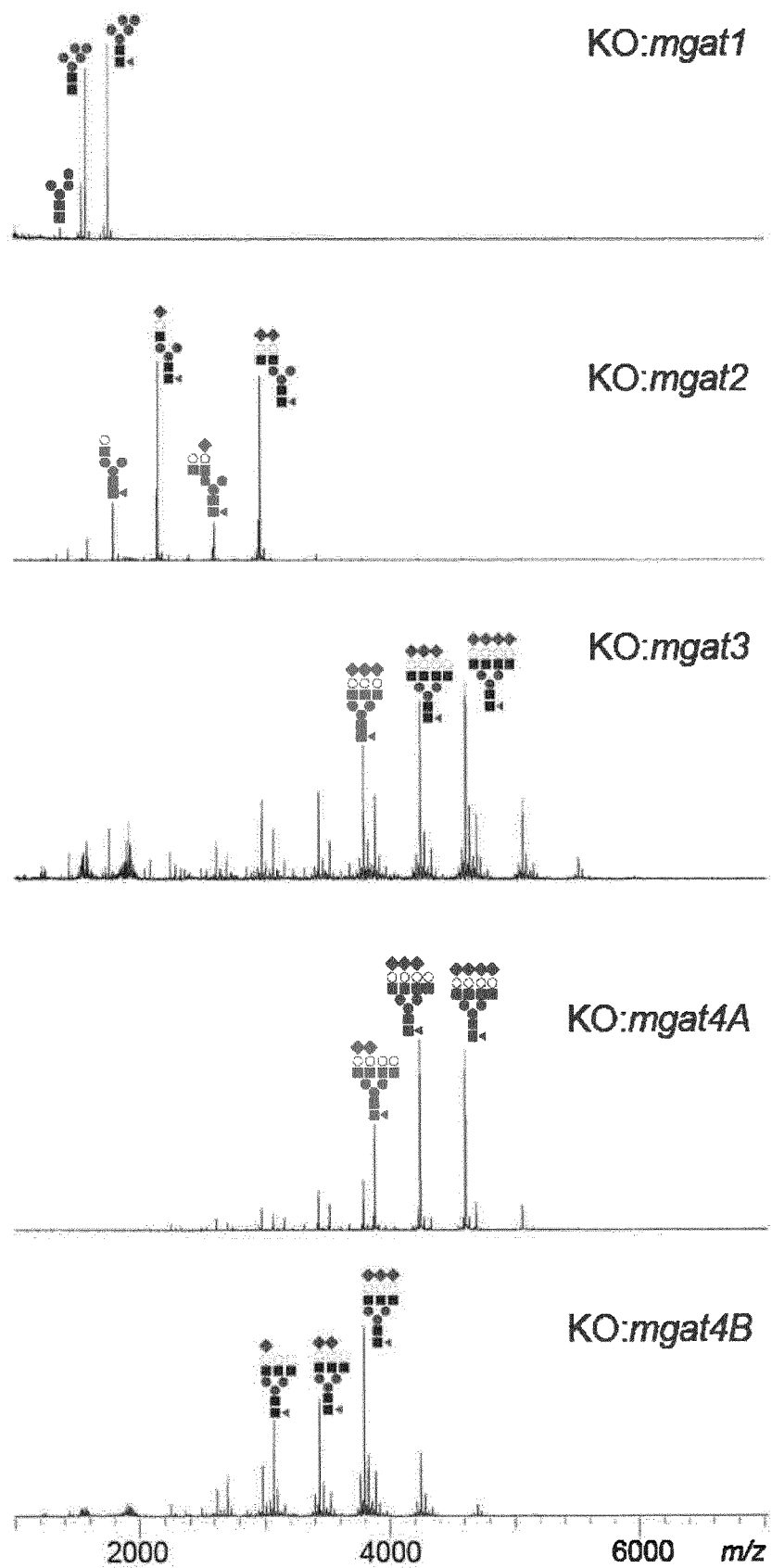
FIG. 5 Glycoprofiling of EPO expressed in CHO cells with KO of genes involved in complex type N-glycan biosynthesis and antennary formation, showing that double KO of mgat4B/5 and triple KO of mgat4A/4B/5 results in homogeneous biantennary N-glycans with a minor amount of poly-LacNAc. Since single KO of mgat4A had minor effects compared to WT it is likely that minor amounts of triantennary structures are present in the double mgat4B/5 KO.
Figure 5B:
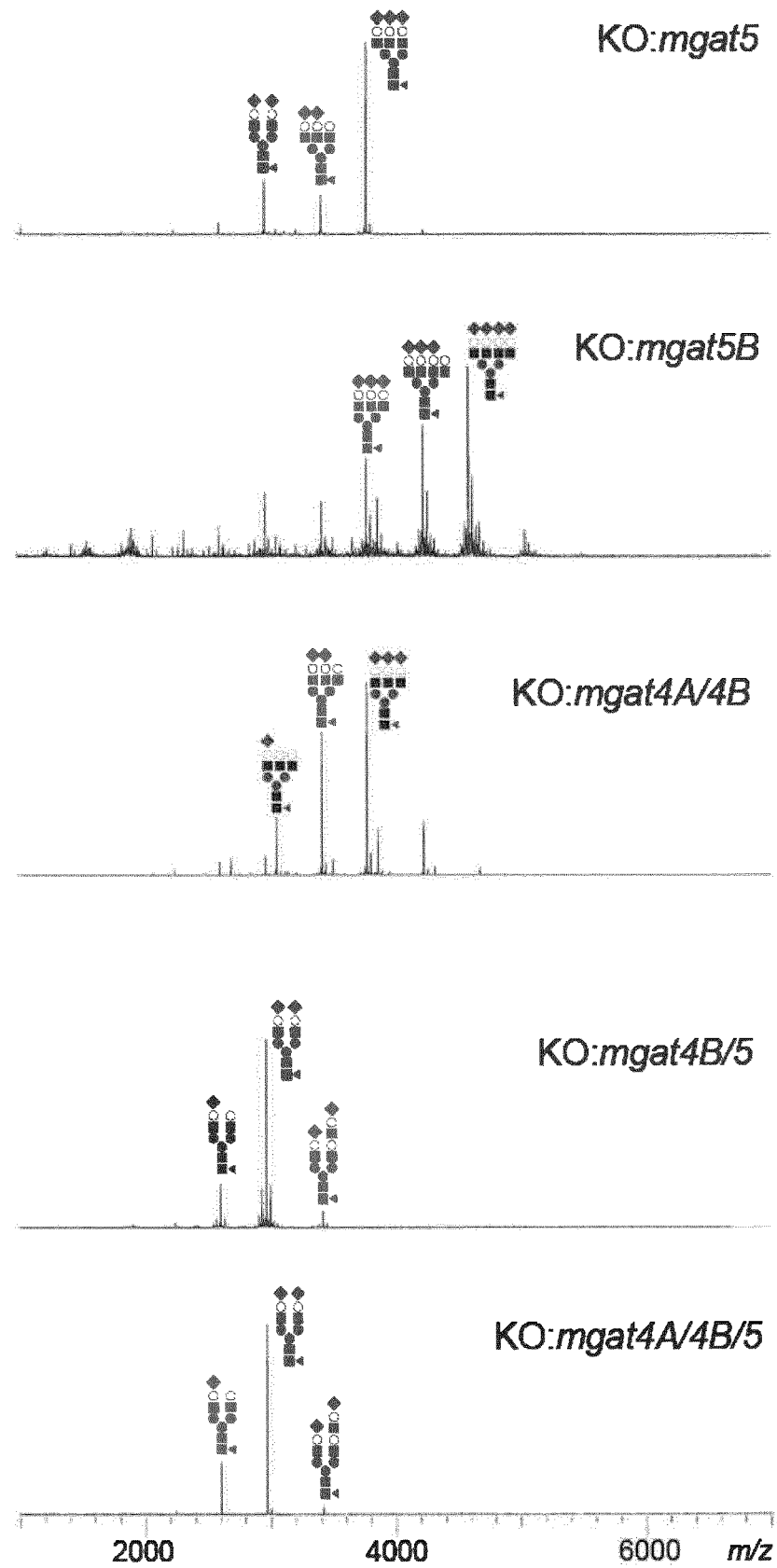
Figure 6:
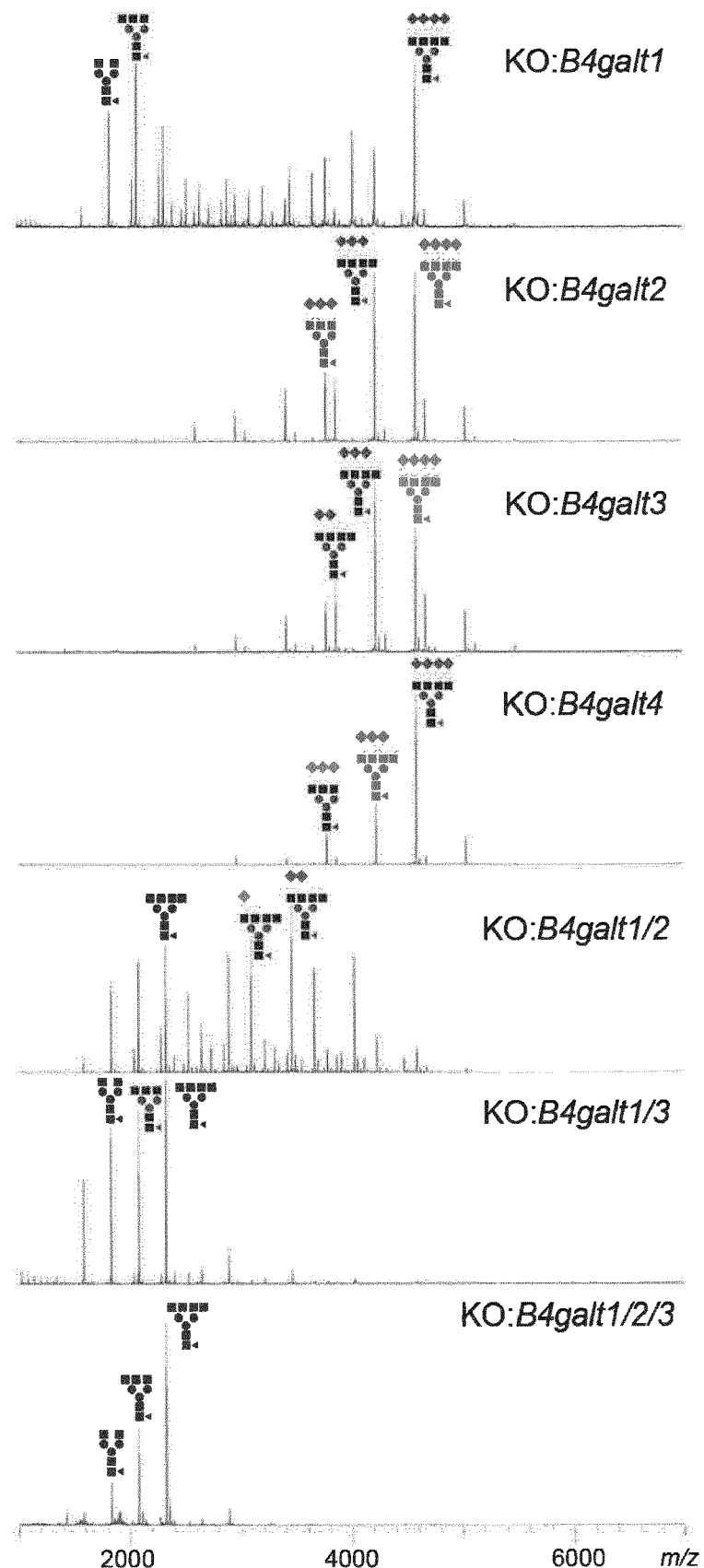
FIG. 6 Glycoprofiling with KO of B4galt1/2/3/4 genes involved in LacNAc biosynthesis, showing that only B4galt1 KO alone produced substantial albeit partial loss of galactosylation, while only stacked KO of B4galt1/3 resulted in near complete loss of galactosylation, while stacked KO of B4galt1/3 resulted in near complete loss of galactosylation. Stacked KO of B4galt1/2/3 resulted in essentially complete loss of galactosylation.
Figure 7:
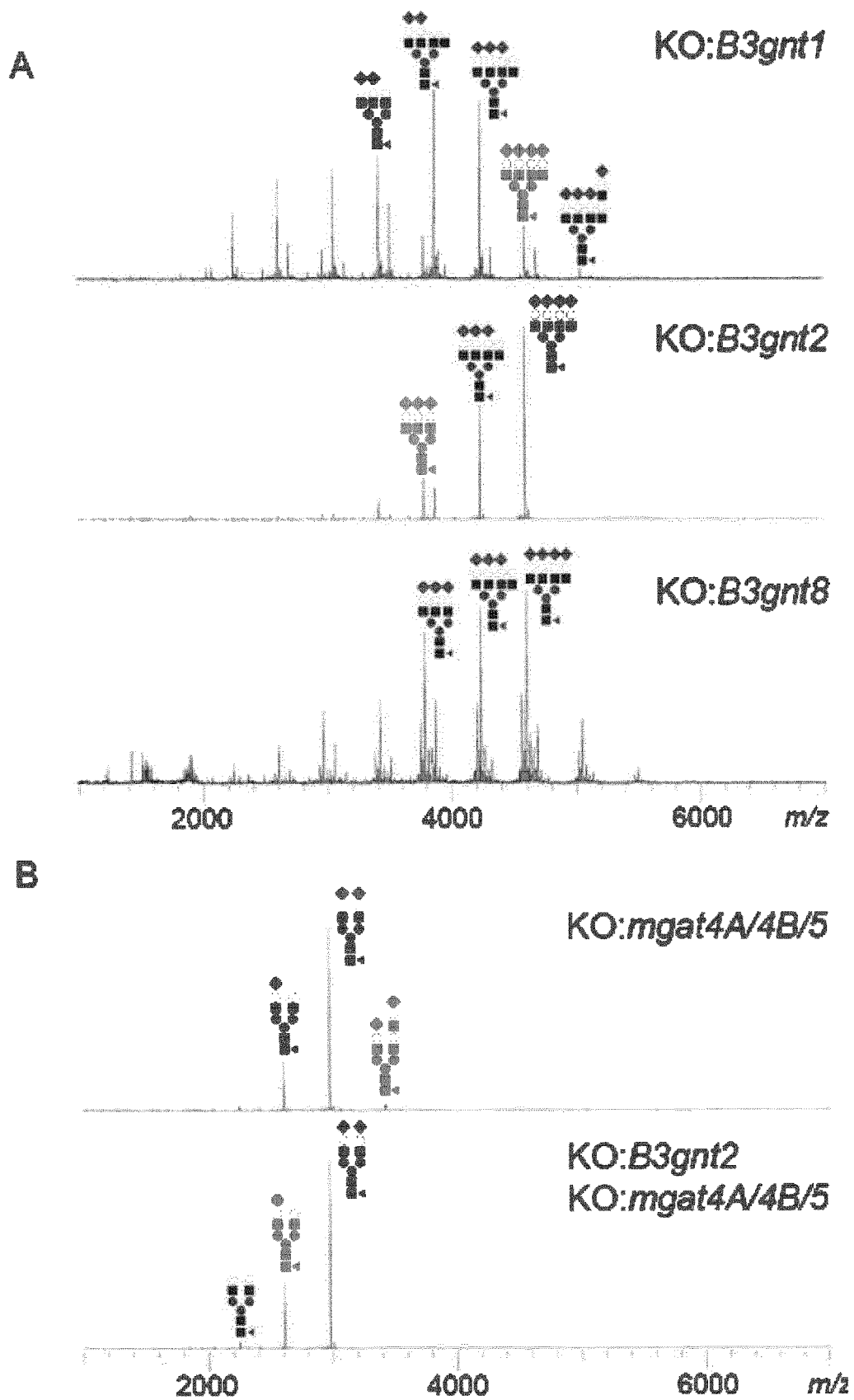
FIG. 7 Glycoprofiling with KO of three β3GlcNAc-transferase genes showing that KO of B3gnt2 results in complete loss of poly-LacNAc, whereas KO of B3gnt1 and B3gnt1 had no effects. Lower PANEL shows that KO of B3gnt2 in combination with mgat4A/4B/5 results in complete loss of poly-LacNAc on biantennary structures.
Figure 8:
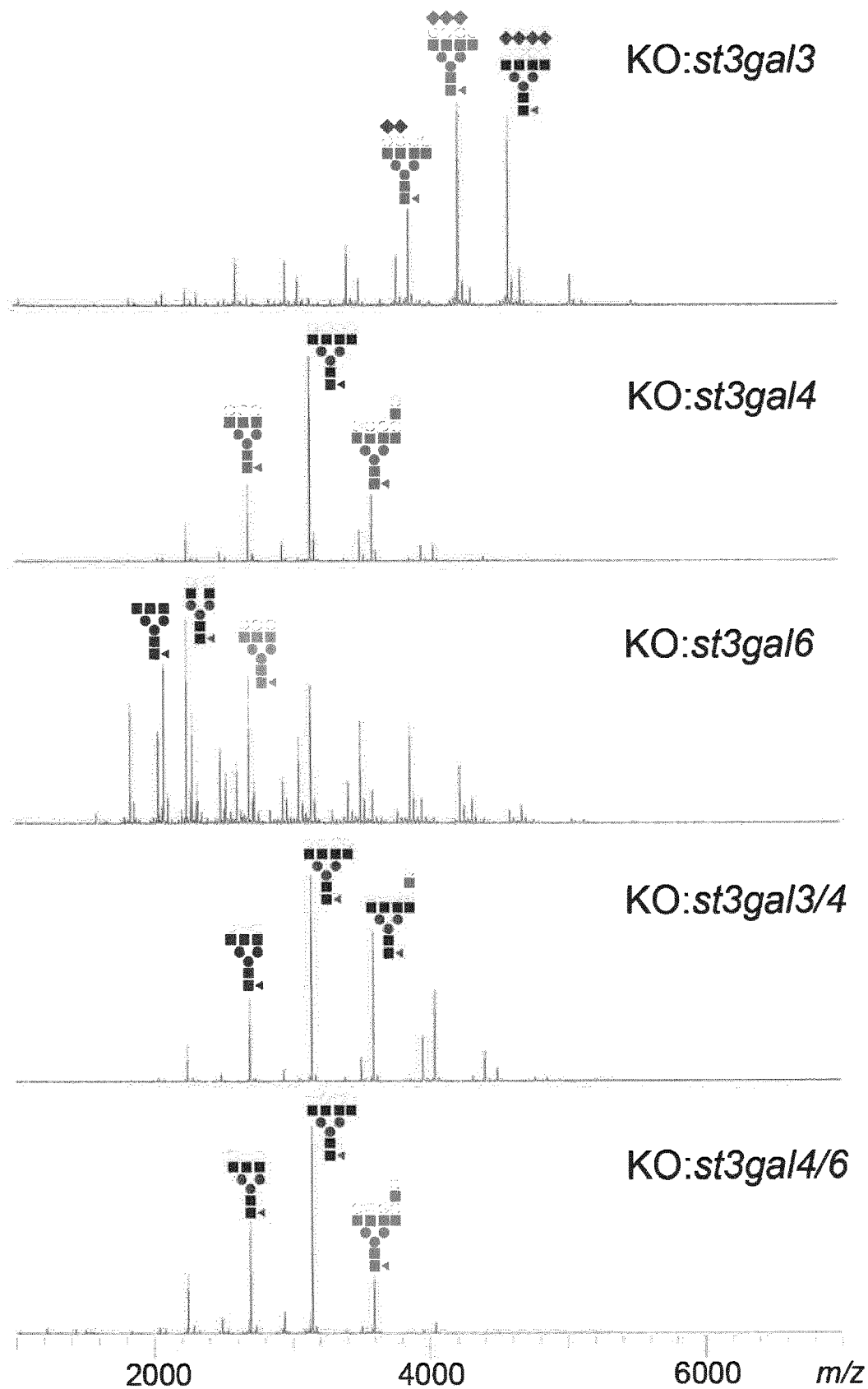
FIG. 8 Glycoprofiling with KO of three α2,3sialyltransferase genes with claimed roles in N-glycosylation, showing that only the double KO of st3gal4/6 resulted in complete loss of sialic acid capping.
Figure 9:
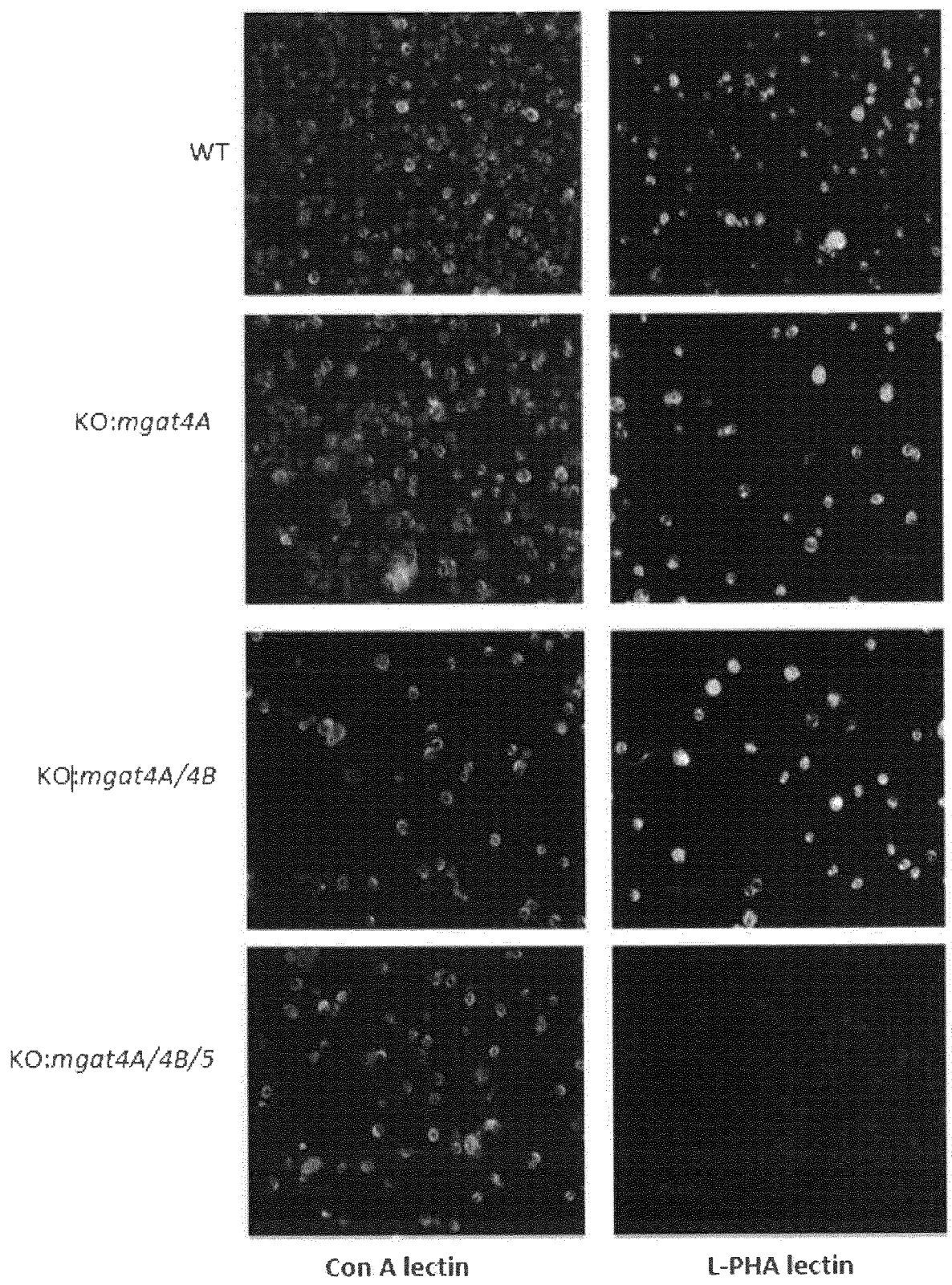
FIG. 9 Immunoflourescense cytology with ConA and L-PHA lectin staining showing loss of L-PHA with knockout of mgat5.
Figure 10A:
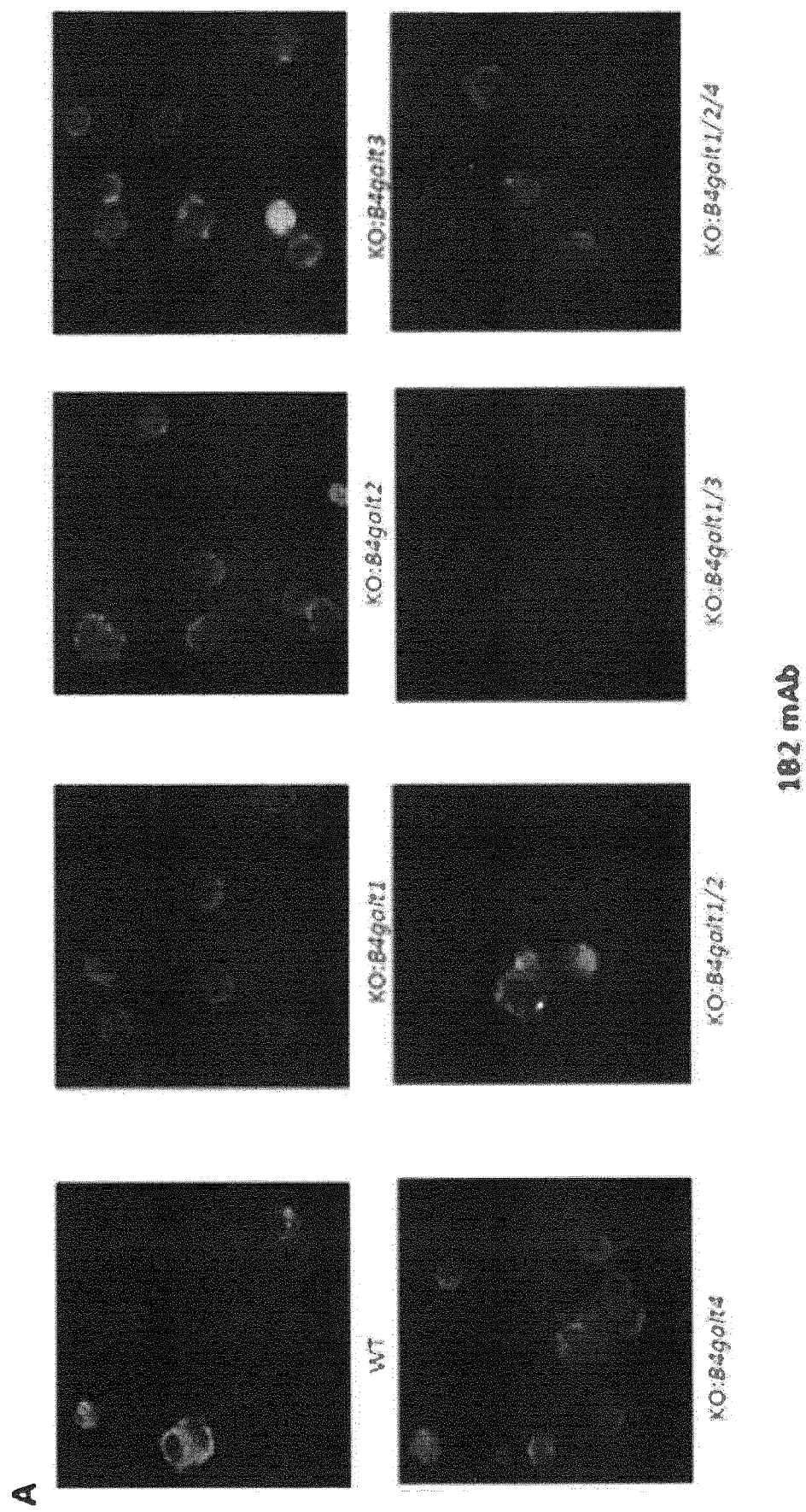
FIG. 10 Immunoflourescense cytology with a monoclonal antibody (clone 1B2) to LacNAc. Panel A shows surprisingly that only stacked KO of B4galt1/3, and not B4galt1/2/4, abolished galactosylation. Panel B shows that KO of B4galt1 in CHO-GS with KO of mgat4A/4B/5 eliminated immunoreactivity for LacNAc while KO of B4galt2, 3, and 4 in the same CHO-GS had no substantial effects.
Figure 10B:
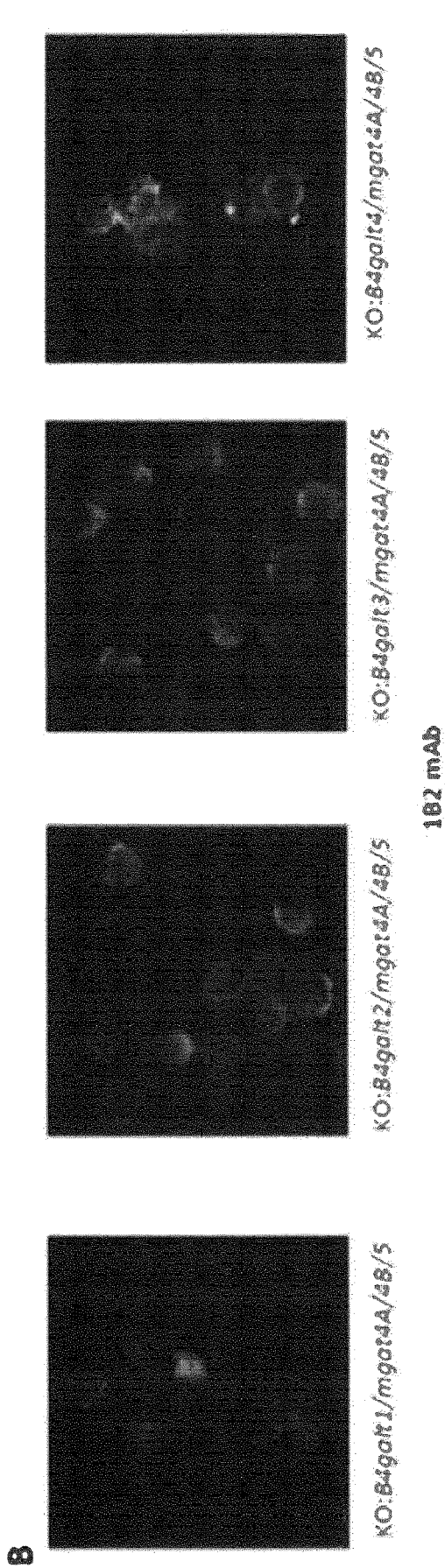
Figure 11:
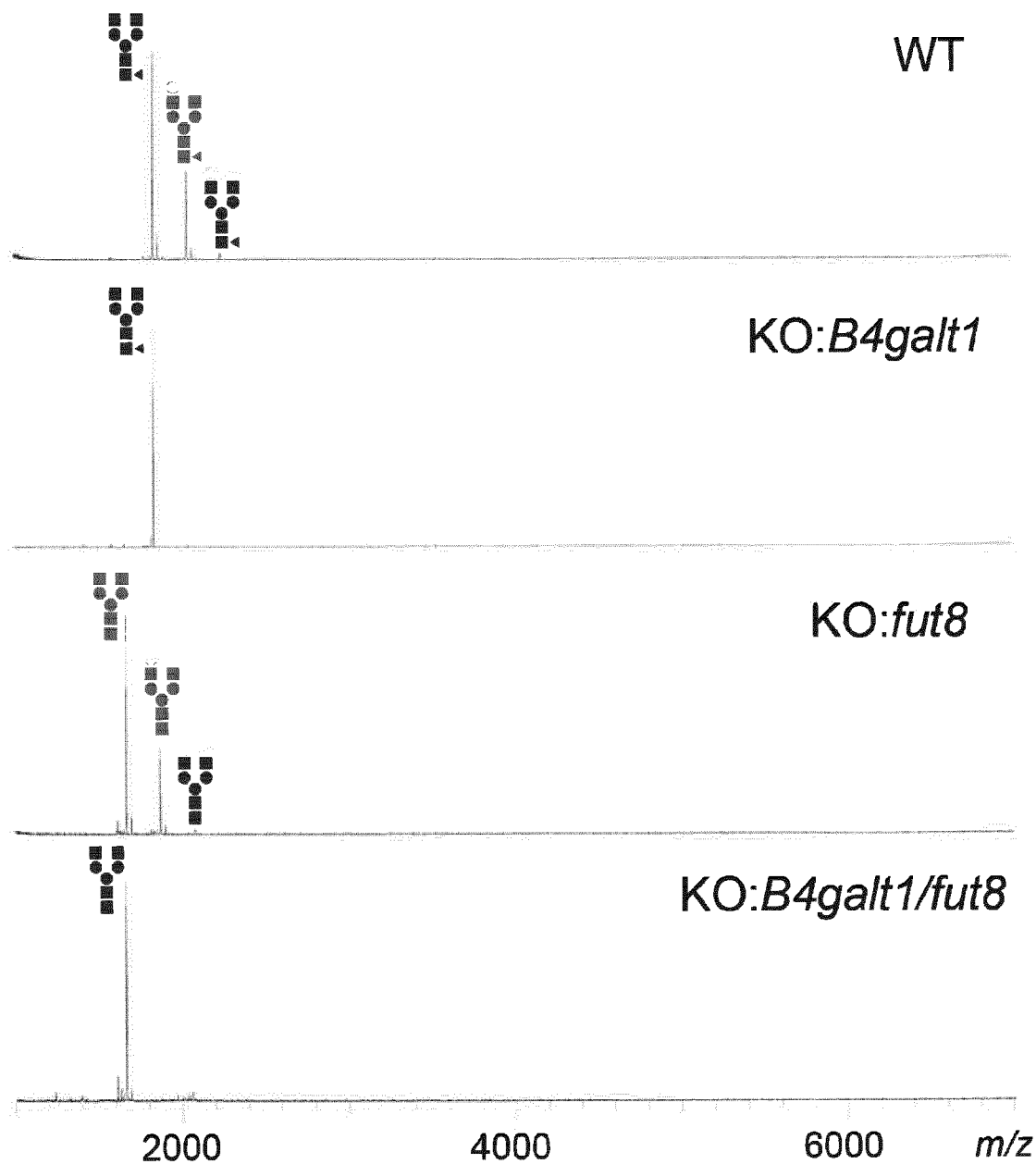
FIG. 11 Recombinant expression of a therapeutic IgG in CHO with KO of B4galt1 resulted in homogenous biantennary N-glycans without galactosylation. Glycoprofiling of IgG produced in CHO WT and B4galt1 KO showing essentially complete loss of the incomplete galactosylation and sialylation characteristic for the conserved N-glycan at Asn297. KO of B4galt1 in combination with fut8 resulted in N-glycans without galactosylation and fucose.
Figure 12:
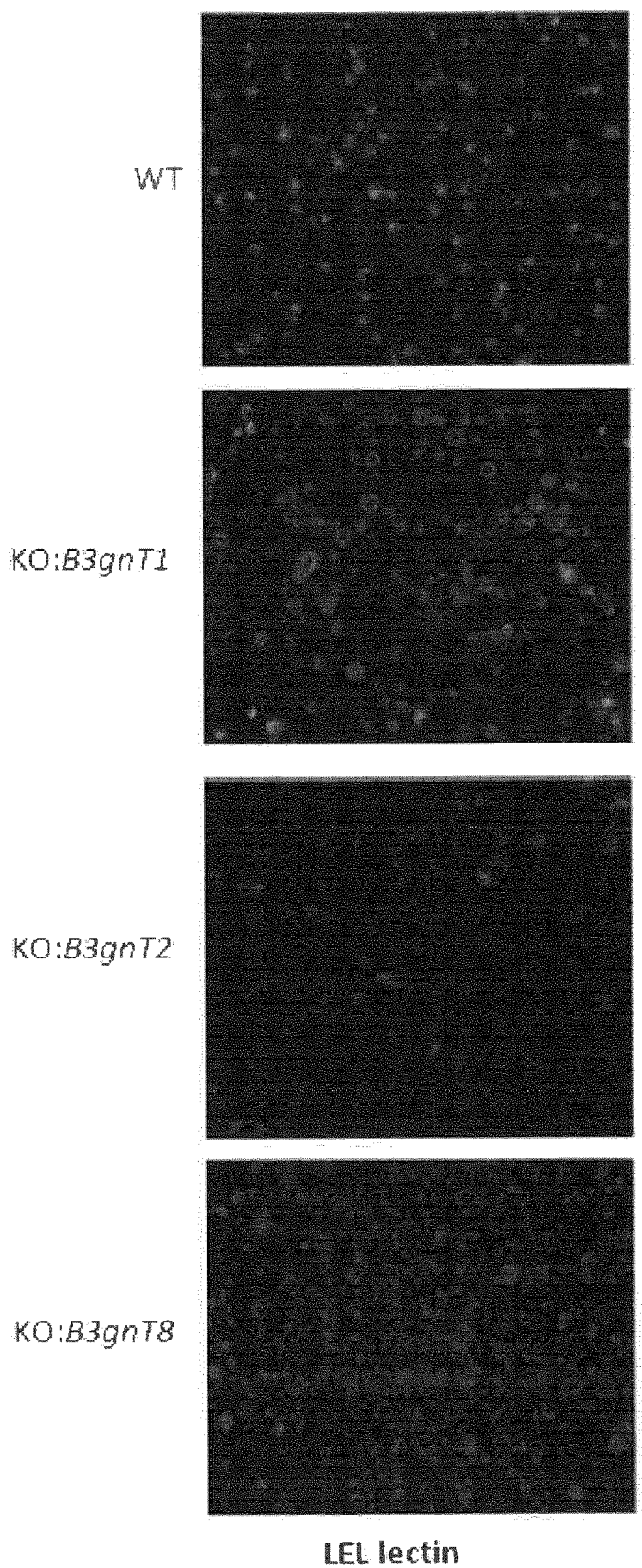
FIG. 12 Immunoflourescense cytology with LEL lectin shows that B3gnt2 is the key gene controlling the LacNAc initiation in CHO cells.
Figure 13:
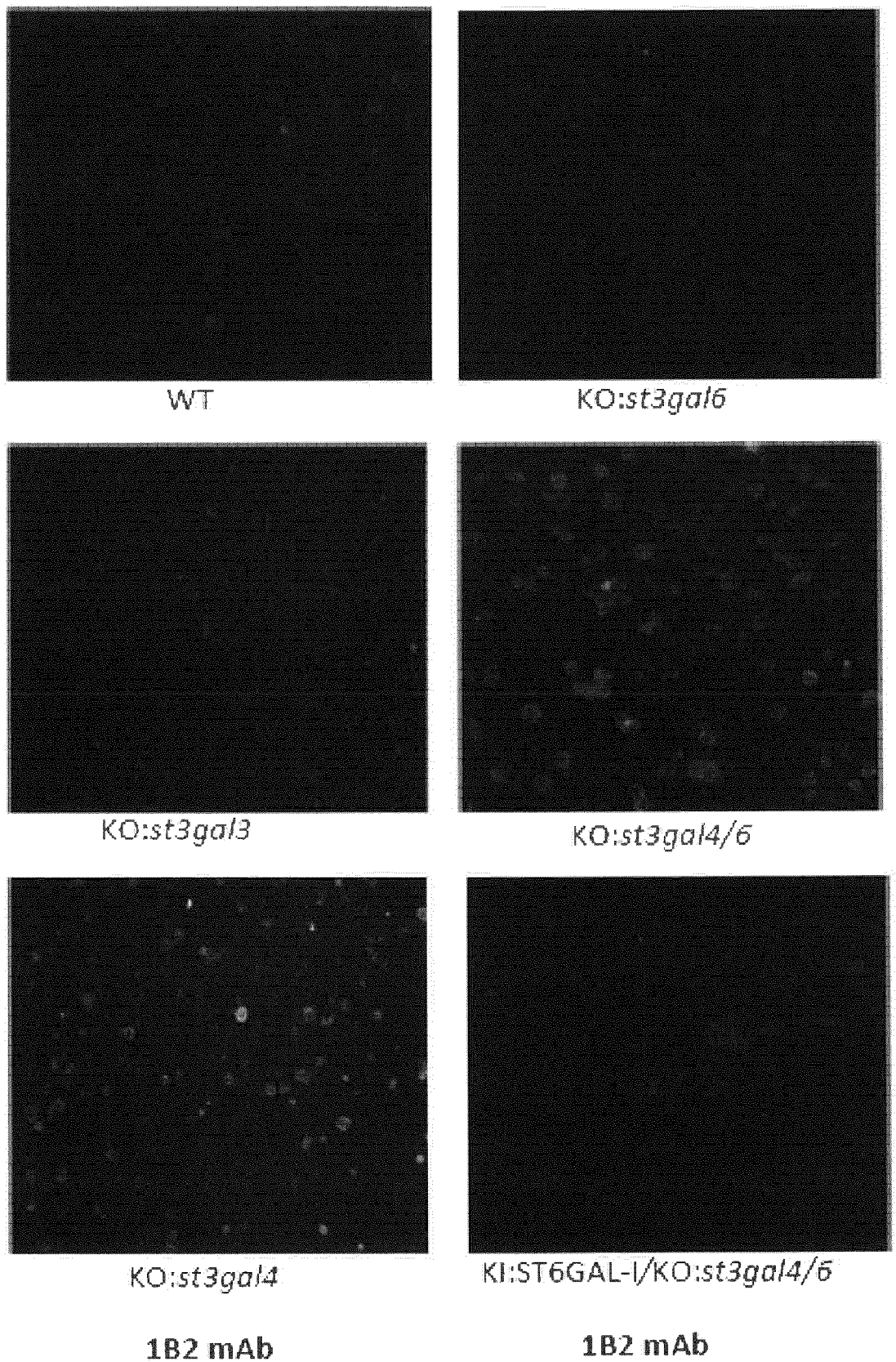
FIG. 13 Immunoflourescense cytology with monoclonal antibody to LacNAc (1B2). Knockout of St3gal3, St3gal4, and St3gal6 individually using immunocytology to evaluate exposure of LacNAc shows that only KO of St3gal4 produced substantial exposure of LacNAc.
Figure 14A:
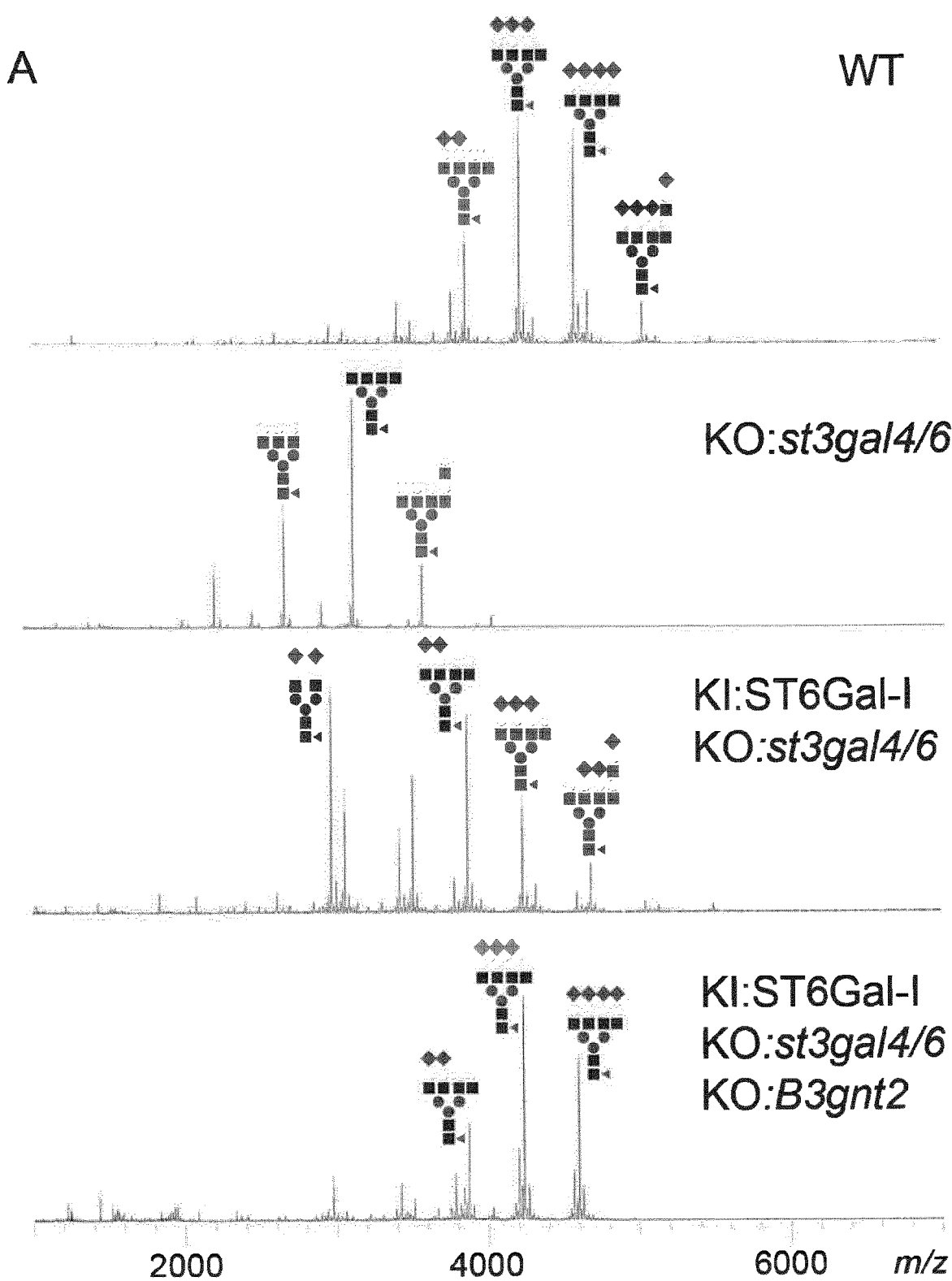
FIG. 14 Glycoprofiling of EPO expressed in CHO with KO of mgat4a/4b/5 and ZFN-mediated knockin of human ST6GAL1. Panel A shows profiling of EPO with homogenous α2,6NeuAc capping of the complete range of N-glycan antennary structures. Also shown is KI of ST6GAL1 in CHO with KO of mgat4a/4b/5/B3gnt2, which produced more homogeneous tetraantennary structures. Panel B shows profiling with additional KO of mgat4a/4b/5 where EPO is produced with homogenous biantennary N-glycans capped by α2,6NeuAc. Also shown are KI of human ST3Gal-4 in combination with KO of st3gal4/6/mgat4a/4b/5/63gnt2 where EPO is produced with homogeneous biantennary N-glycans without poly-LacNAc and capped by α2,3NeuAc.
Figure 14B:
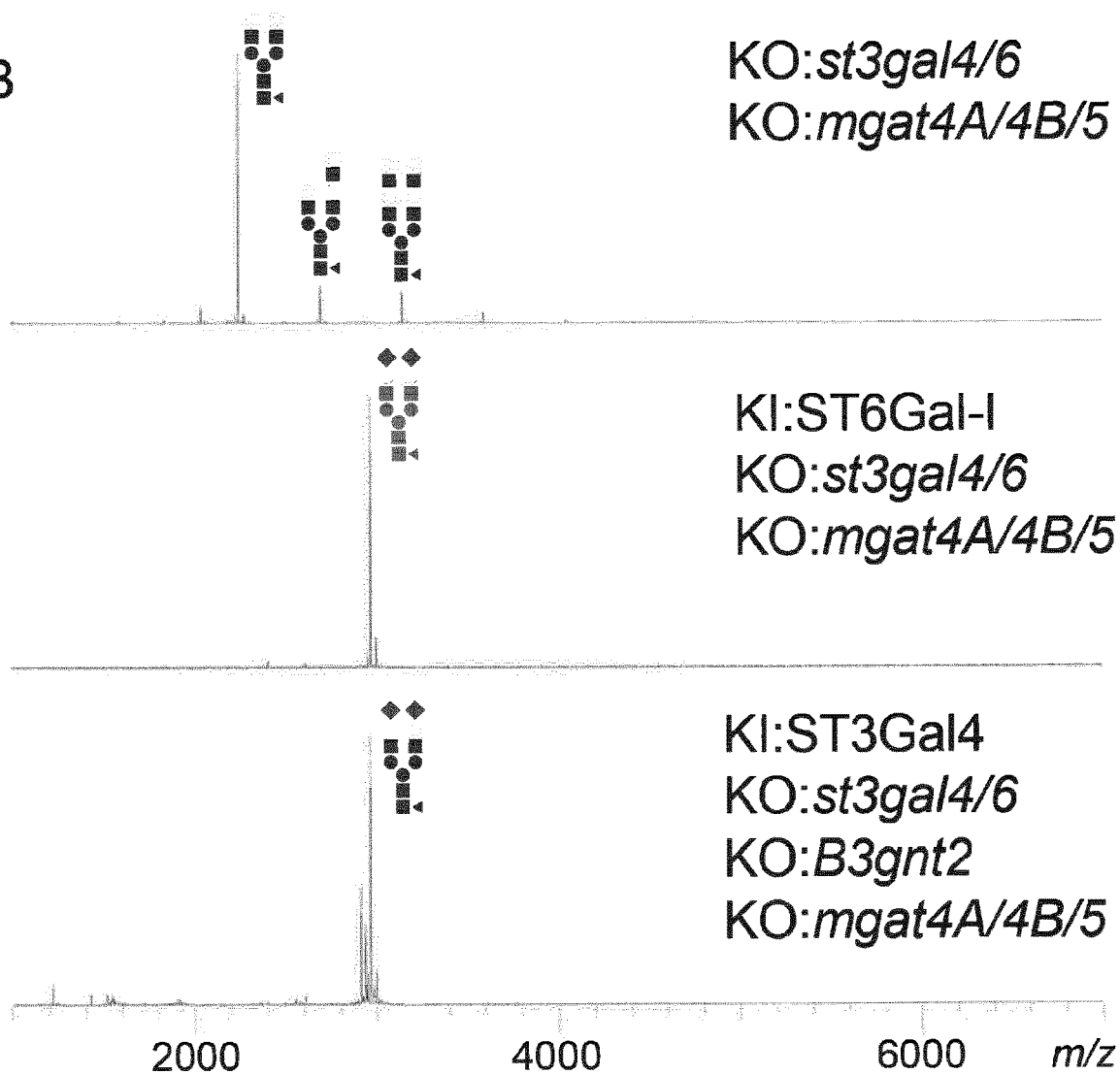
Figure 15A:
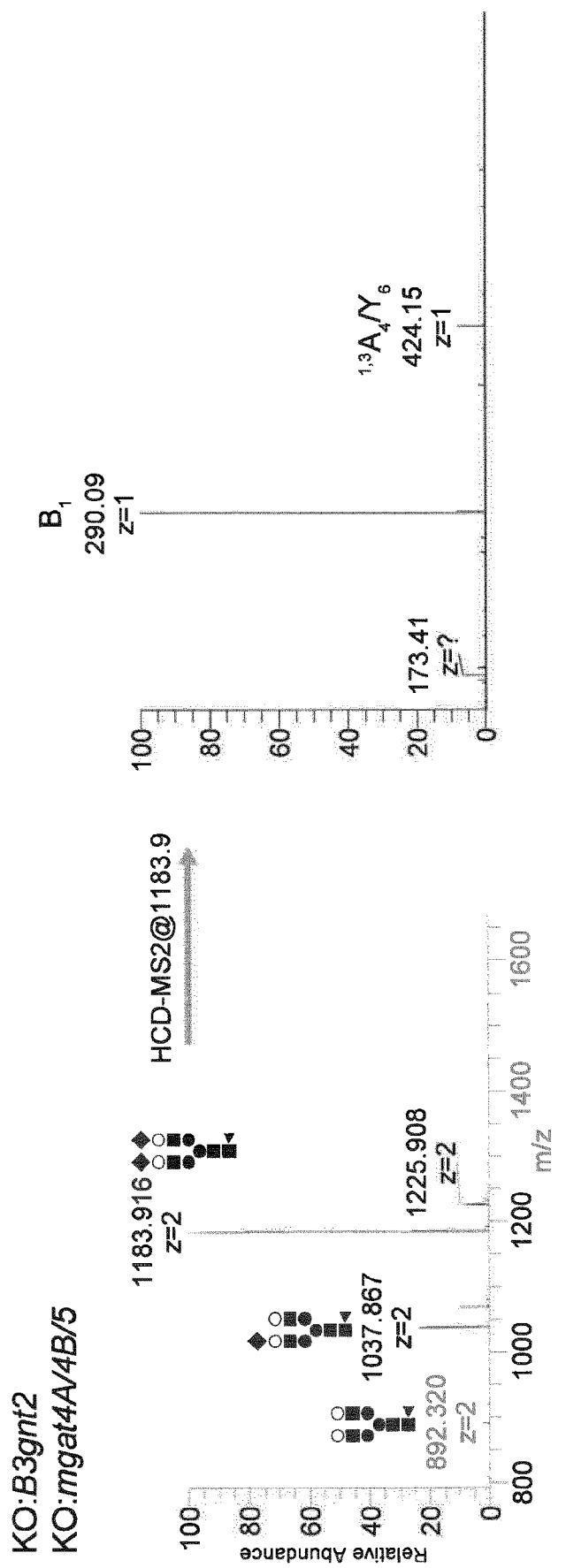
FIG. 15 Negative ion ESI-MS/MS of the precursor ions at m/z 1183.92 (sialylated biantennary N-glycan with core fucose) from EPO produced in CHO with Mgat4a/4b/5 KO (Top Panels) and with both Mgat4a/4b/5 and st3gal4/6 KO and KI of ST6GAL1 (Bottom Panels). The presence of the diagnostic fragment ions at m/z 306.12 demonstrates the presence of α2,6 terminal sialylation.
Figure 15B:
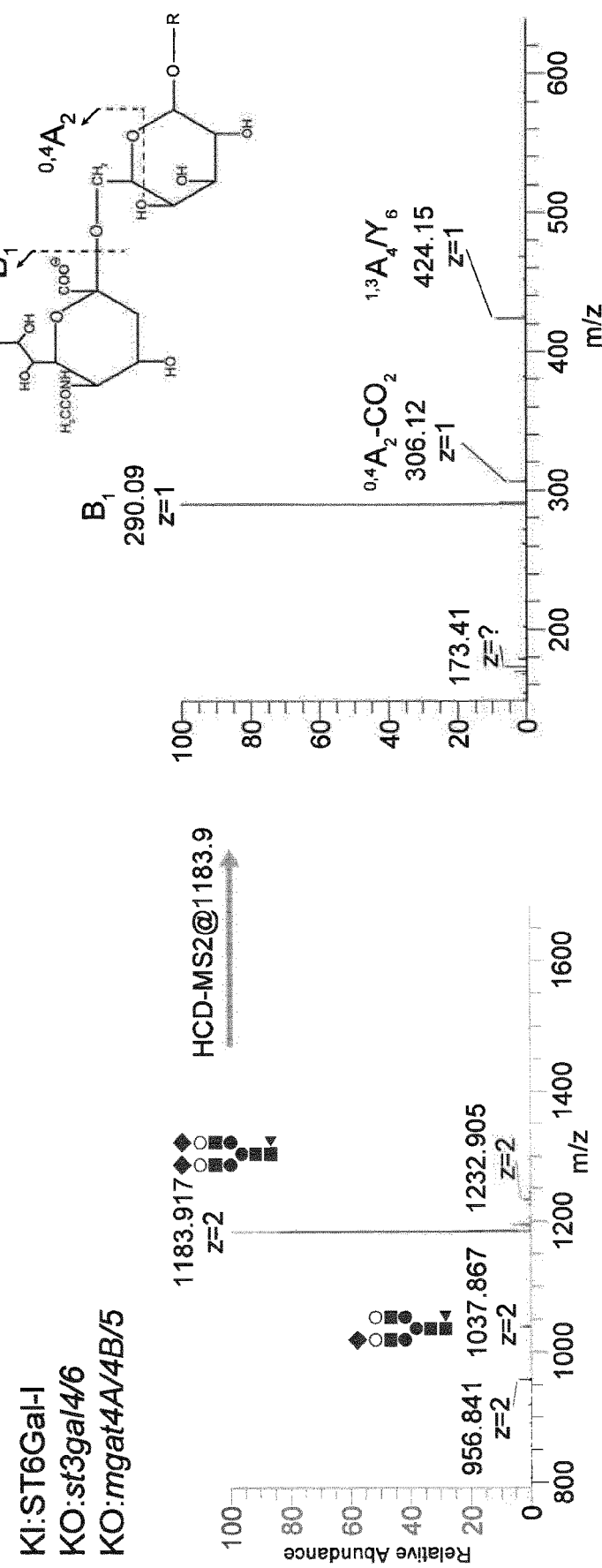
Figure 16:
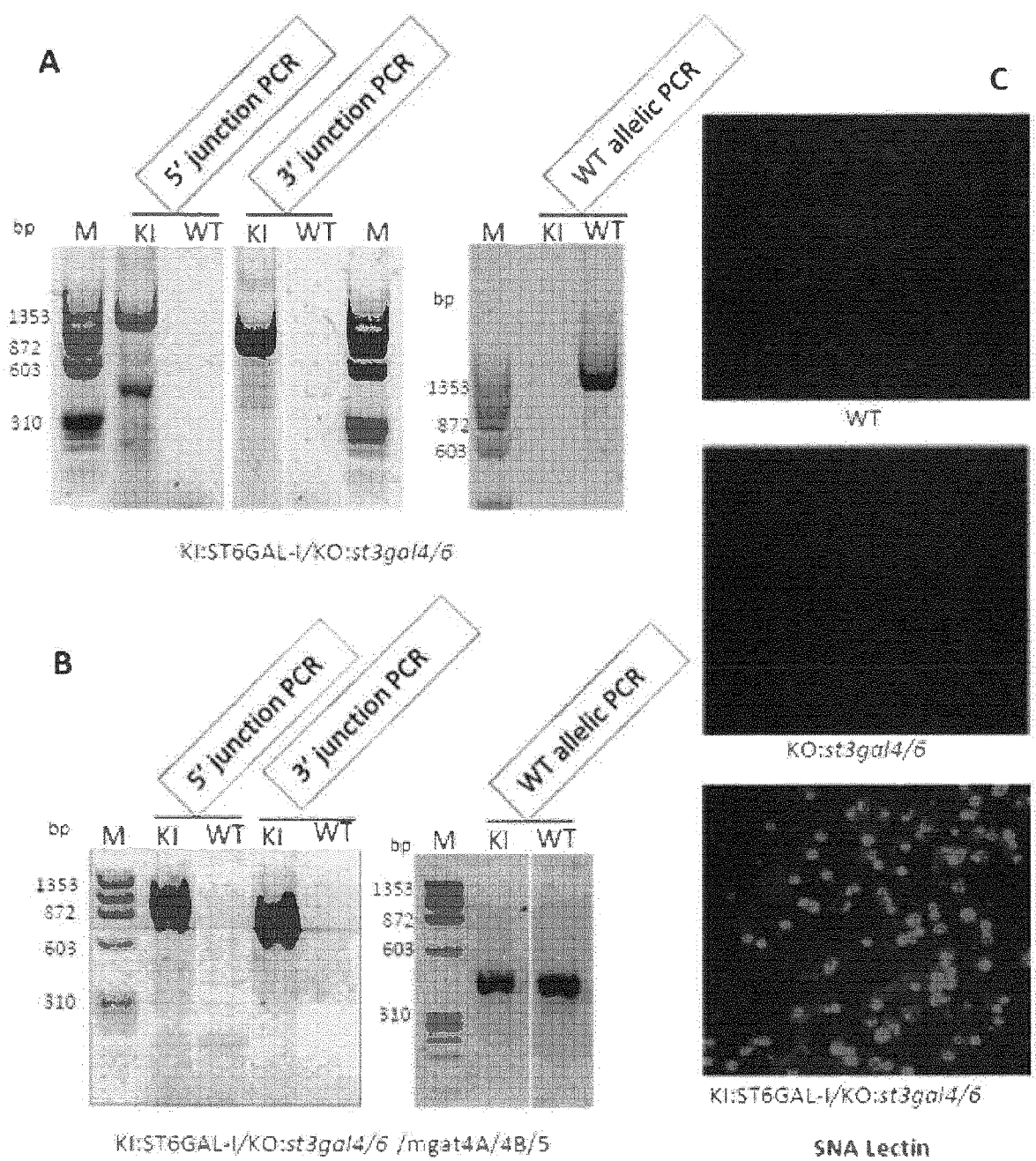
FIG. 16 Analysis of targeted KI of ST6GAL1 by junction PCR. Panel A shows that a modified ObLiGaRe targeted KI strategy utilizing two inverted ZFN binding sites flanking the ST6GAL1 full open reading frame in donor plasmid was used. 5' and 3' junction PCR confirmed targeted integration into the Safeharbor#1 site in the CHO clone with st3gal4/6 KO. (b) 5' and 3' junction PCR confirmed targeted integration in the CHO clone with st3gal4/6/mgat4a/4b/5 KO. The status of allelic copy number of integration was determined by WT allelic PCR. The presence of desired band in WT allelic PCR indicates the presence of Safeharbor#1 site without the integration of targeted KI of gene of interest on at least one of the allele. The results showed biallelic integration of ST6Gal-I at Safeharbor#1 site in the CHO st3gal4/6 KO clone and monoallelic integration in the mgat4a/4b/5/St3gal4/6 KO clone. The ObLiGaRe KI strategy was highly efficient with approximately 30-50% single cloned cells expressing ST6GAL1 as evaluated by antibody and lectin immunocytology.
Figure 17:
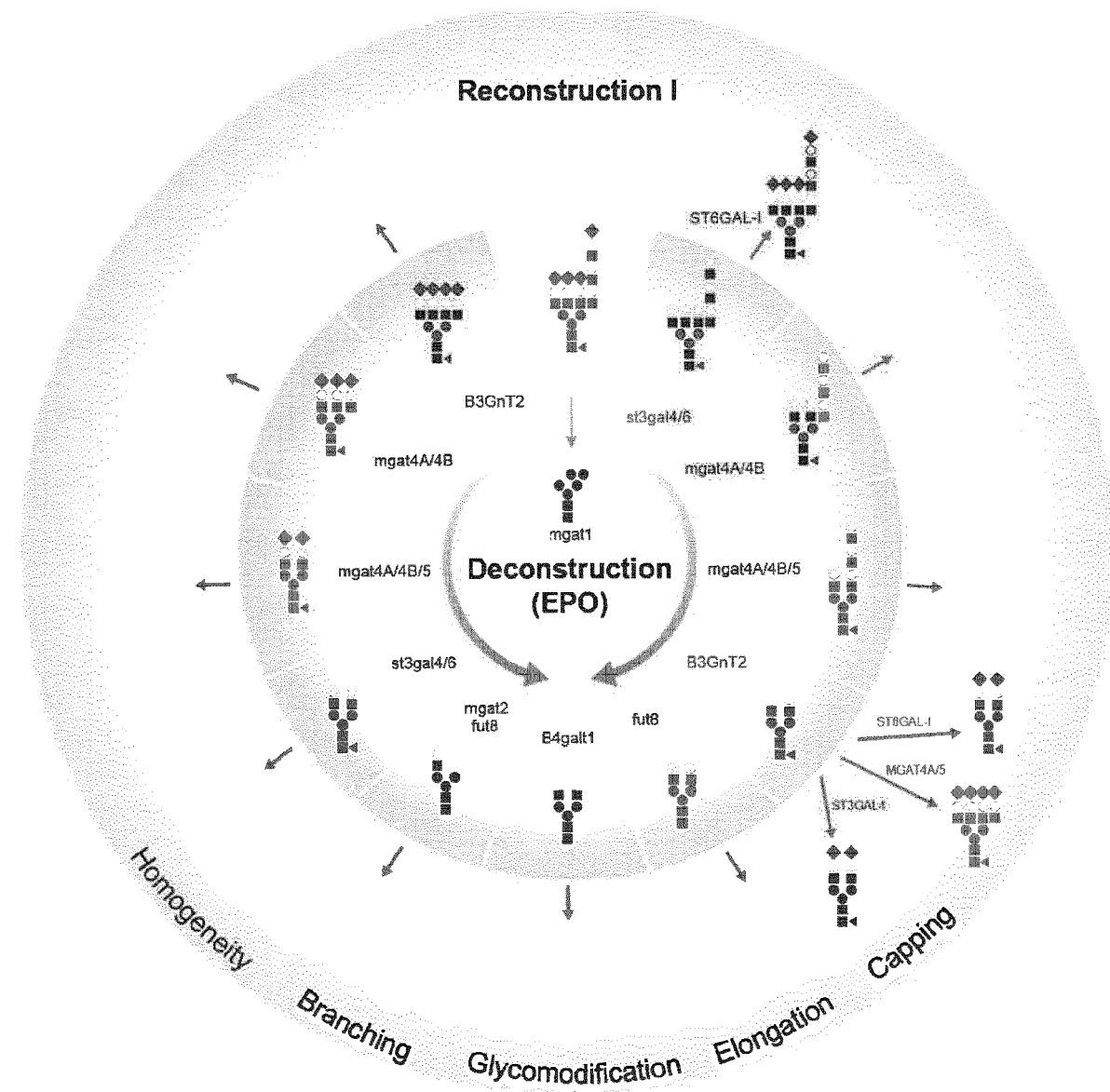
FIG. 17 Graphic depiction of the genetic deconstruction of N-glycosylation in CHO established using EPO as N-glycoprotein reporter. Several KO CHO lines have potential for production of glycoprotein therapeutics with more homogenous glycosylation (e.g. biantennary α2,3-sialylated N-glycans for EPO, and biantennary non-galactosylated/sialylated with and without core Fuc for IgG. Examples of reconstruction based on KI are shown producing homogenous α2,6-sialylation after KO of α2,3-sialylation capacities with either WT N-glycan branching heterogeneity or homogenous biantennary structure, homogeneous α2,3-sialylation after KO of endogeneous sialylation, and homogeneous tetranatennary structures with α2,6-sialylation after KO of endogeneous branching and sialylation capacities. Reconstruction may address homogeneity as shown, but also branching, poly-LacNAc elongation, and any type of capping as indicated.
Figure 18:
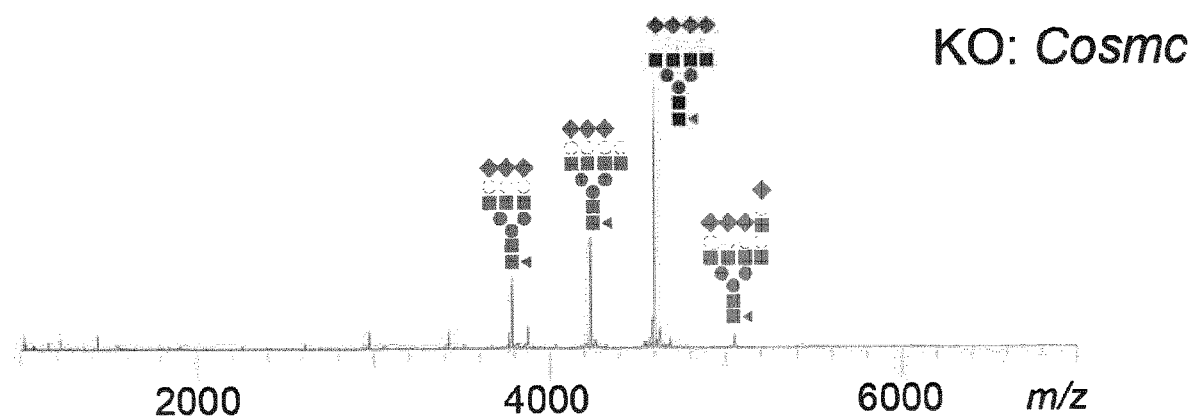
FIG. 18 Glycoprofiling of EPO expressed in CHO with KO of Cosmc to eliminate O-GalNAc elongation with Gal and NeuAc showing improved capacity for sialic acid capping of N-glycans at all three N-glycosites present in EPO, when compared to WT as shown in FIG. 4.
Figure 19:
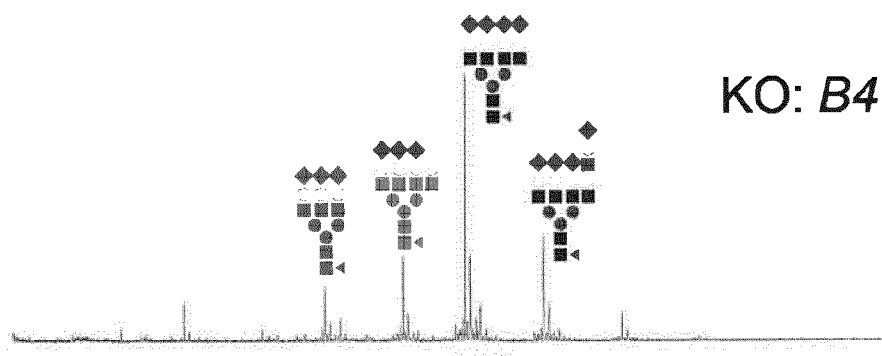
FIG. 19 Glycoprofiling of EPO expressed in CHO with KO of B4galT7 to eliminate O-Xyl elongation with Gal (PANEL A) and Pomgnt1 to eliminate O-Man elongation with Gal and NeuAc (PANEL B) showing enhanced capacity for sialic acid capping of N-glycans at all three N-glycosites present in EPO. PANEL C illustrates glycoprofiling of EPO expressed in double KO of B4galt7 and pomgnt1, and Panel D illustrates glycoprofiling of EPO expressed in triple KO of B4galt7, pomgnt1, and cosmc showing the same improved capacity for sialic acid capping of N-glycans in EPO.
Figure 19:
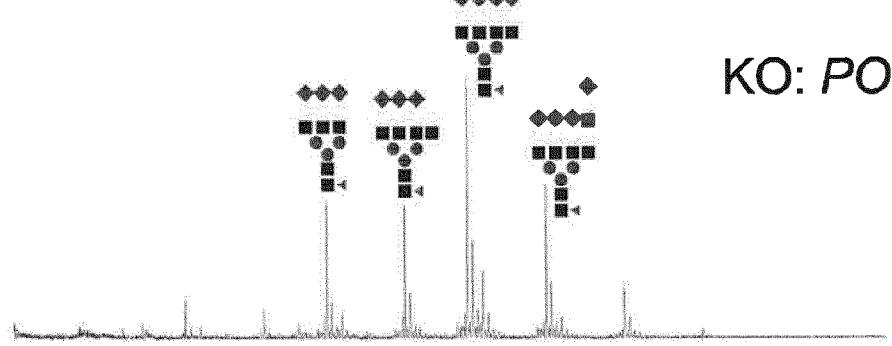
Figure 19:
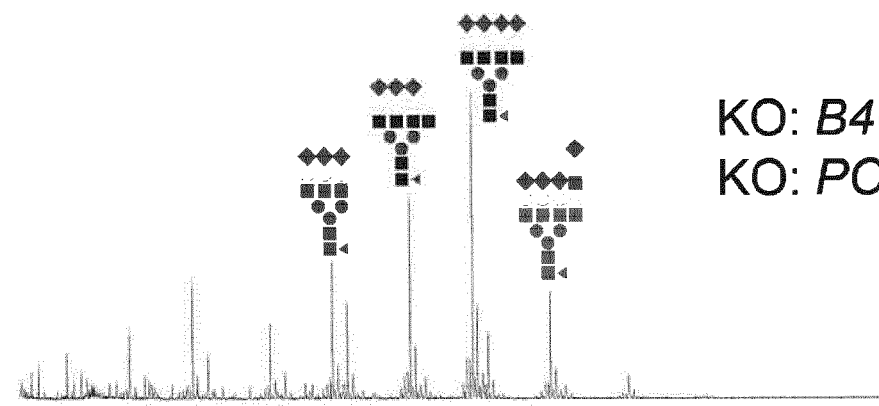
Figure 19:
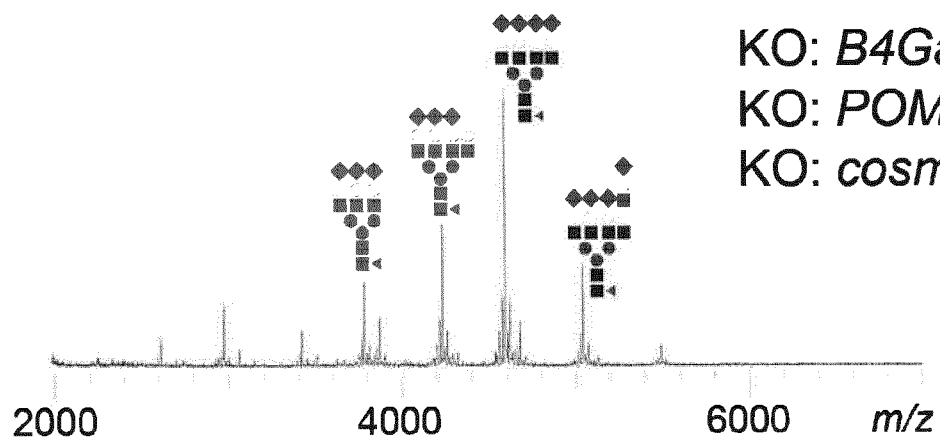
Figure 20:
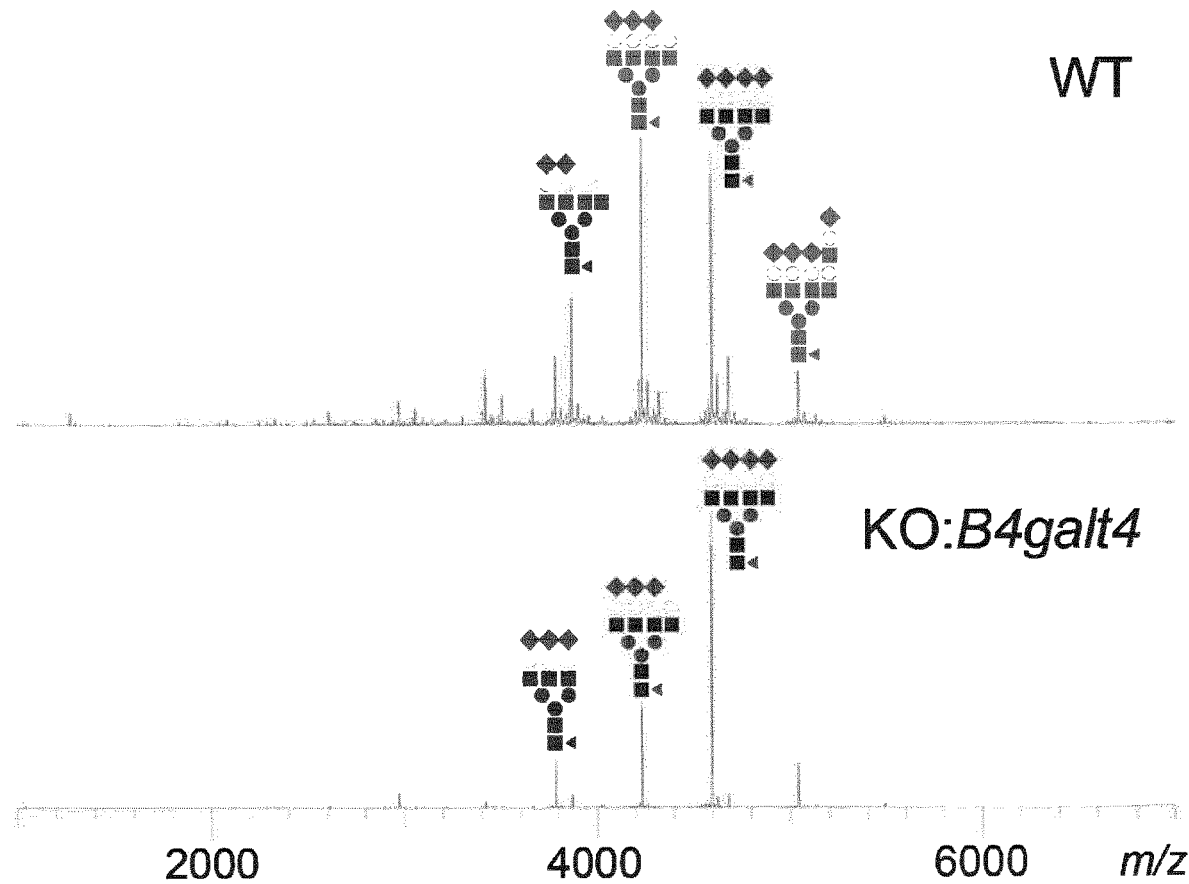
FIG. 20 Glycoprofiling of EPO expressed in CHO with KO of B4galT4 to eliminate a galactosyltransferase paralog not utilized for N-glycans and this glycosylation pathway showing improved capacity for sialic acid capping of N-glycans at all three N-glycosites present in EPO.

The present invention will now be described in more detail in the following.

DETAILED DESCRIPTION OF THE INVENTION

Sugar chains of glycoproteins are roughly divided into two types, namely a sugar chain which binds to asparagine (N-glycoside-linked sugar chain) and a sugar chain which binds to other amino acid such as serine, threonine (O-glycoside-linked sugar chain), based on the binding form to the protein moiety.

The sugar chain terminus which binds to asparagine is called a reducing end, and the opposite side is called a non-reducing end. It is known that the N-glycoside-linked sugar chain includes a high mannose type in which mannose alone binds to the non-reducing end of the core structure; a complex type in which the non-reducing end side of the core structure has at least one parallel branches of galactose-N-acetylglucosamine (hereinafter referred to as "Gal-GlcNAc") and the non-reducing end side of Gal-GlcNAc has a structure of sialic acid, bisecting N-acetylglucosamine or the like; a hybrid type in which the non-reducing end side of the core structure has branches of both of the high mannose type and complex type.

In general, most of the humanized antibodies of which application to medicaments is in consideration are prepared using genetic recombination techniques and produced using Chinese hamster ovary tissue-derived CHO cell as the host cell. As described above, the sugar chain structure play important roles for the structure, function, size, circulatory half-life, and pharmacokinetic behaviour of glycoprotein drugs. Moreover, the sugar structure plays a remarkably important role in the effector function of antibodies and differences are observed in the sugar chain structure of glycoproteins expressed by host cells, development of a host cell which can be used for the production of an antibody having higher effector function is desired.

Thus, an object of the present invention is to provide a cell capable of expressing a gene encoding a polypeptide of interest, wherein the polypeptide of interest is expressed comprising one or more posttranslational modification patterns.

In one embodiment of the present invention is the posttranslational modification pattern a glycosylation.

The optimal glycoform of a glycoprotein may be identified by the following process:
(i) producing a plurality of different glycoforms of said glycoprotein by expressing in cell lines harboring at least one novel glycosylation capacity for example by harboring two or more modifications of GT gene expression levels, and (ii) determination of the activity of the different glyco forms in comparison with a reference glycoprotein in (a) suitable bioassay(s); and (iii) selection of the glycoform with the higher/highest activity and determination of the production cell genotype fingerprint which is correlated with the higher/highest activity level of said glycoprotein.

The above described process allows the identification of the optimal glycoform of a glycoprotein. For those skilled in the art by using the genotype fingerprint identified in (iii) may generate an efficient engineered cell line with the optimal genotype for producing glycoprotein with said glycoform.

The genes involved in this highly complex machinery have been examined by the present inventors (see the examples) and effects have been identified.

Thus, in one aspect of the present invention is one or more of the group selected from mgat4A, mgat4B, mgat4C, mgat5, mgat5B, B4galt1, B4galt2, B4galt3, B4galt4, B3gnt1, B3gnt2, B3gnt8, st3gal3, st3gal4, and st3gal6 involved in the posttranslational modification patterns.

In another aspect of the present invention are one or more of these genes knocked out or in.

The present invention relates to a cell comprising a gene encoding a polypeptide of interest, wherein the polypeptide of interest is expressed comprising one or more posttranslational modification patterns.

One object of the present invention relates to a cell comprising one or more glycosyltransferase genes that have been inactivated, and that has new and/or more homogeneous stable glycosylation capacities, wherein mgat2 has been knocked out (KO), and with and without KO of mgat4A and/or mgat4B and/or mgat5 allowing production of N-glycans with monoantennary structure.

A preferred embodiment of the present invention relates to a cell comprising one or more glycosyltransferase genes that have been inactivated, and that has new and/or more homogeneous stable glycosylation capacities, wherein mgat2 has been knocked out (KO), and with or without KO of mgat4A and/or mgat4B and/or mgat5 allowing production of N-glycans with monoantennary structure.

One embodiment of the present invention relates to a cell comprising one or more glycosyltransferase genes that have been inactivated, and that has new and/or more homogeneous stable glycosylation capacities, wherein mgat2 has been knocked out (KO).

Another embodiment of the present invention relates to the cell as described herein, wherein mgat2 has been knocked out (KO), and with KO of mgat4A and/or mgat4B and/or mgat5 allowing production of N-glycans with monoantennary structure.

Yet another embodiment of the present invention relates to the cell as described herein, wherein mgat2 and mgat4A has been knocked out (KO), allowing production of N-glycans with monoantennary structure.

A further embodiment of the present invention relates to the cell as described herein, wherein mgat2 and mgat4B has been knocked out (KO), allowing production of N-glycans with monoantennary structure.

An even further embodiment of the present invention relates to the cell as described herein, wherein mgat2 and mgat5 has been knocked out (KO), allowing production of N-glycans with monoantennary structure.

Another embodiment of the present invention relates to the cell as described herein, wherein mgat2 has been knocked out (KO) together with KO of one or more of the genes selected from the group consisting of mgat4A, mgat4B and mgat5.

Another object of the present invention relates to a cell comprising one or more glycosyltransferase genes that have been inactivated, and that has new and/or more homogeneous stable glycosylation capacities, wherein mgat2 has been knocked out (KO), and with and without KO of mgat4A and/or mgat4B and/or mgat5 in combination with KO of sialyltransferases allowing production of N-glycans with monoantennary structure and without sialic acid capping.

A preferred embodiment of the present invention relates to a cell comprising one or more glycosyltransferase genes that have been inactivated, and that has new and/or more homogeneous stable glycosylation capacities, wherein mgat2 has been knocked out (KO), and with or without KO of mgat4A and/or mgat4B and/or mgat5 in combination with KO of sialyltransferases allowing production of N-glycans with monoantennary structure and without sialic acid capping.

One embodiment of the present invention relates to a cell comprising one or more glycosyltransferase genes that have been inactivated, and that has new and/or more homogeneous stable glycosylation capacities, wherein mgat2 has been knocked out (KO) in combination with KO of sialyltransferases allowing production of N-glycans with monoantennary structure and without sialic acid capping.

Another embodiment of the present invention relates to the cell as described herein, wherein mgat2 has been knocked out (KO), and with KO of mgat4A and/or mgat4B and/or mgat5 in combination with KO of sialyltransferases allowing production of N-glycans with monoantennary structure and without sialic acid capping.

Yet another embodiment of the present invention relates to the cell as described herein, wherein mgat2 and mgat4A has been knocked out (KO) in combination with KO of sialyltransferases allowing production of N-glycans with monoantennary structure and without sialic acid capping.

A further embodiment of the present invention relates to the cell as described herein, wherein mgat2 and mgat4B has been knocked out (KO), in combination with KO of sialyltransferases allowing production of N-glycans with monoantennary structure and without sialic acid capping.

An even further embodiment of the present invention relates to the cell as described herein, wherein mgat2 and mgat5 has been knocked out (KO), in combination with KO of sialyltransferases allowing production of N-glycans with monoantennary structure and without sialic acid capping.

Another embodiment of the present invention relates to the cell as described herein, wherein mgat2 has been knocked out (KO) in combination with KO of sialyltransferases and with KO of one or more of the genes selected from the group consisting of mgat4A, mgat4B and mgat5.

Yet another object of the present invention relates to a cell comprising one or more glycosyltransferase genes that have been inactivated, and that has new and/or more homogeneous stable glycosylation capacities, wherein mgat2 has been knocked out (KO), and with and without KO of mgat4A and/or mgat4B and/or mgat5 in combination with KO of sialyltransferases and B3gnt2 allowing production N-glycans with monoantennary structure and without sialic acid capping and without poly-LacNAc.

A cell comprising one or more glycosyltransferase genes that have been inactivated, and that has new and/or more homogeneous stable glycosylation capacities, wherein mgat2 has been knocked out (KO), and with or without KO of mgat4A and/or mgat4B and/or mgat5 in combination with KO of sialyltransferases and B3gnt2 allowing production N-glycans with monoantennary structure and without sialic acid capping and without poly-LacNAc.

One embodiment of the present invention relates to a cell comprising one or more glycosyltransferase genes that have been inactivated, and that has new and/or more homogeneous stable glycosylation capacities, wherein mgat2 has been knocked out (KO) in combination with KO of sialyltransferases and B3gnt2 allowing production N-glycans with monoantennary structure and without sialic acid capping and without poly-LacNAc.

Another embodiment of the present invention relates to the cell as described herein, wherein mgat2 has been knocked out (KO), and with KO of mgat4A and/or mgat4B and/or mgat5 in combination with KO of sialyltransferases and B3gnt2 allowing production N-glycans with monoantennary structure and without sialic acid capping and without poly-LacNAc.

Yet another embodiment of the present invention relates to the cell as described herein, wherein mgat2 and mgat4A has been knocked out (KO) in combination with KO of sialyltransferases and B3gnt2 allowing production N-glycans with monoantennary structure and without sialic acid capping and without poly-LacNAc.

A further embodiment of the present invention relates to the cell as described herein, wherein mgat2 and mgat4B has been knocked out (KO), in combination with KO of sialyltransferases and B3gnt2 allowing production N-glycans with monoantennary structure and without sialic acid capping and without poly-LacNAc.

An even further embodiment of the present invention relates to the cell as described herein, wherein mgat2 and mgat5 has been knocked out (KO), in combination with KO of sialyltransferases and B3gnt2 allowing production N-glycans with monoantennary structure and without sialic acid capping and without poly-LacNAc.

Another embodiment of the present invention relates to the cell as described herein, wherein mgat2 has been knocked out (KO) in combination with KO of sialyltransferases and B3gnt2 and with KO of one or more of the genes selected from the group consisting of mgat4A, mgat4B and mgat5.

In one embodiment of the present invention the cell is a mammalian cell or an insect cell.

In another embodiment of the present invention the cell is derived from Chinese hamster ovary or from human kidney.

In a further embodiment of the present invention the cell is selected from the group consisting of CHO, NS0, SP2/0, YB2/0, CHO-K1, CHO-DXB11, CHO-DG44, CHO-S, HEK293, HUVEC, HKB, PER-C6, NS0, or derivatives of any of these cells. In one embodiment of the present invention is the cell a CHO cell.

In another embodiment of the present invention the cell furthermore encodes an exogenous protein of interest.

In yet another embodiment of the present invention is the protein of interest an antibody, an antibody fragment, such as a Fab fragment, an Fc domain of an antibody, or a polypeptide.

In yet another embodiment of the present invention the protein of interest is a coagulation factor such as coagulation factor II (FII), coagulation factor V (FV), coagulation factor VII (FVIIa), coagulation factor VIII (FVIII), coagulation factor IX (FIX), coagulation factor X (FX), or coagulation factor XIII (FXIII).

One aspect of the present invention relates to a method for the production of di- and triPEGylated glycoproteins, the method comprising the step of enzymatic glycoPEGylation of glycoengineered variants.

In one embodiment of the present invention is the glycoprotein EPO.

Another aspect of the present invention relates to a method for the production of recombinant glycoproteins, comprising the step of generating a cell with specific glycosylation properties, wherein specific glycosylation property is the capacity for monoantennary N-glycan synthesis.

A further aspect of the present invention relates to a method for producing an enzymatically modified glycoprotein, comprising the step of generating a cell with specific glycosylation properties, and the enzymatically modification of interest.

In one embodiment of the present invention is the enzymatically modification a polymer.

In another embodiment of the present invention is the enzymatically modification a conjugation to another protein.

A further aspect of the present invention relates to a glycoprotein obtainable from a method according to the present invention.

In one embodiment of the present invention has the glycostructure outcome one or more of the following changes selected from the group consisting of simpler glycan structure, more homogeneous product, more sialic acids per molecule, non-sialylated, non-galactosylated, more homogeneous bi-antennary, more homogeneous monoantennary, more homogeneous triantennary, more homogeneous without poly-LacNAc, higher productivity in cell culture, new stable homogeneous glycosylation capacities, more human glycostructure, more homogeneous glycosylation and improved ADCC targeting of IgG, modified fucose level, no fucose, improved substrate for generating glycoconjugates.

One aspect of the present invention relates to a glycoprotein according to the present invention, which is a homogeneous glycoconjugate produced from a glycoprotein having a simplified glycan profile.

Another aspect of the present invention relates to a glycoprotein according to the present invention, which is a homogeneous glycoprotein conjugate comprising a polymer.

The glycoprotein can be enzymatically modified with the polymer, and the glycoprotein can be produced by the cell according to the present invention.

Another aspect of the present invention relates to a glycoprotein according to the present invention, which is a homogeneous glycoprotein conjugate comprising a polymer selected from, PEG, HEP, XTEN, PSA, HES.

A further aspect of the present invention relates to a glycoprotein according to the present invention, which is a homogeneous PEGylated protein conjugate produced from a protein variant according to the invention having a simplified glycan profile.

Another aspect of the present invention relates to a glycoprotein according to the present invention, which is a homogeneous PEGylated protein conjugate produced from an protein variant having a simplified glycan profile.

One aspect of the present invention relates to a glycoprotein according to the present invention, which is a simplified enzymatic glycoPEGylation process using glycoengineered protein variants that provides high yield of di- and triPEGylated protein forms.

Another aspect of the present invention relates to a glycoprotein according to the present invention, which is a protein conjugate according to the invention comprising FII, FV, FVIIa, FVIII, FIX, FX, FXIII, a Fab fragment of an antibody, or a Fc domain of an antibody.

A further aspect of the present invention relates to a glycoprotein according to the present invention, which is a protein-protein conjugate produced from a glycoprotein with a simplified glycan profile.

In one embodiment of the present invention is the glycoprotein according to the present invention a protein-protein conjugate produced from a glycoprotein with a simplified glycan profile comprising a Fab fragment and one of either FII, FV, FVIIa, FVIII, FIX, FX or FXIII.

In another embodiment of the present invention is the glycoprotein according to the present invention a protein-protein conjugate produced from a glycoprotein with a simplified glycan profile comprising a Fc Domain and one of either FII, FV, FVIIa, FVIII, FIX, FX or FXIII.

In a further embodiment of the present invention is the glycoprotein according to the present invention a homogeneous PEGylated EPO conjugate produced from an EPO variant having a simplified glycan profile.

One aspect of the present invention relates to the use of recombinant glycoproteins comprising monoantennary N-glycans for enzymatic modification of polypeptides.

Knockout means full or partial impairment of the function of the gene of interest.

In one aspect of the present invention is one or more of the above mentioned genes knocked out using zinc finger nucleases ZFN. ZFNs can be used for inactivation of a FUT8 gene or any of the other genes disclosed herein. ZFNs comprise a zinc finger protein (ZFP) and a nuclease (cleavage) domain.

In another aspect of the present invention is one or more of the above mentioned genes knocked out using transcription activator-like effector nucleases (TALENs).

TALENs are artificial restriction enzymes generated by fusing a TAL effector DNA binding domain to a DNA cleavage domain.

In yet another aspect of the present invention is one or more of the above mentioned genes knocked out using CRISPRs (clustered regularly interspaced short palindromic repeats).

CRISPRs are DNA loci containing short repetitions of base sequences. Each repetition is followed by short segments of "spacer DNA" from previous exposures to a virus.

CRISPRs are often associated with cas genes that code for proteins related to CRISPRs. The CRISPR/Cas system is a prokaryotic immune system that confers resistance to foreign genetic elements such as plasmids and phages and provides a form of acquired immunity.

CRISPR spacers recognize and cut these exogenous genetic elements in a manner analogous to RNAi in eukaryotic organisms.

The CRISPR/Cas system is used for gene editing (adding, disrupting or changing the sequence of specific genes) and gene regulation in species throughout the tree of life. By delivering the Cas9 protein and appropriate guide RNAs into a cell, the organism's genome can be cut at any desired location.

In a further embodiment of the present invention the cell does or does not have α-1,6-fucosyltransferase activity.

The cell of the present invention may by a cell that does not comprise the gene of interest to be expressed or the cell may comprise the gene of interest to be expressed. The cell that does not comprise the gene of interest to be expressed is usually called "a naked cell".

The host cell of the present invention may be any host, so long as it can express an antibody molecule. Examples include a yeast cell, an animal cell, an insect cell, a plant cell and the like.

In one embodiment of the present invention is the cell selected from the group consisting of CHO, NS0, SP2/0, YB2/0, YB2/3HL.P2.G11.16Ag.20, NSO, SP2/0-Ag14, BHK cell derived from a syrian hamster kidney tissue, antibody-producing hybridoma cell, human leukemia cell line (Namalwa cell), an embryonic stem cell, and fertilized egg cell.

The cell can be an isolated cell or in cell culture or a cell line.

The protein of interest can be various types of protein, and in particular proteins that benefit from being expressed as glycoproteins In a preferred embodiment the protein is erythropoietin (EPO).

In another embodiment is the protein α1-antitrypsin. In one aspect of the present invention is the protein a recombinant blood factor.

In one embodiment of the present invention is the recombinant blood factor selected from the group consisting of one or more of factor VIII, factor IX, factor XIII A-subunit, thrombin, and factor VIIa.

In one aspect of the present invention is the protein a recombinant thrombolytic, anticoagulant or another blood-related product.

In one embodiment of the present invention is the recombinant thrombolytic, anticoagulant or another blood-related product selected from the group consisting of one or more of tissue plasminogen activator (tPA), hirudin, antithrombin, plasmin, plasma kallikrein inhibitor, and activated protein C.

In one aspect of the present invention is the protein a recombinant hormone.

In one embodiment of the present invention is the recombinant hormone selected from the group consisting of one or more of insulin, insulin degludec, human growth hormone, somatropin, pegvisomant, follicle-stimulating hormone, follitropin alfa, corifollitropin alfa, follitropin beta, metreleptin, liraglutide, parathyroid hormone, lutropin, teriparatide, nesiritide, and glucagon.

In one aspect of the present invention is the protein a recombinant growth hormone.

In one embodiment of the present invention is the recombinant growth hormone selected from the group consisting of one or more of EPO, filgrastim, sargramostim, mecaserim, and palifermin.

In one aspect of the present invention is the protein human growth hormone.

In one aspect of the present invention the protein is a glycosylated variant of human growth hormone.

In one aspect of the present invention is the protein a Recombinant interferon, interleukin or tumor necrosis factor.

In one embodiment of the present invention is the Recombinant interferon, interleukin or tumor necrosis factor selected from the group consisting of one or more of interferon alfa, PEGinterferon alfa, PEGinterferon alfa-2a, PEGinterferon alfa, interferon beta-1b, algulcosidase alfa, and laronidase.

In one aspect of the present invention is the protein an antigen or vaccine component.

In one aspect of the present invention is the protein of the present invention relevant for a disease or disorder selected from the group consisting of one or more of Hemophilia A, Hemophilia B, Acute myocardial infarction, heparinassociated thrombocytopenia, venous thrombosis, Symptomatic vitreomacular adhesion/vitreomacular traction, Acute angioedema, Hereditary antithrombin deficiency, Hereditary angioedema, sepsis, diabetes, diabetes mellitus, Growth failure/growth hormone deficiency, infertility/subfertility, Type 2 diabetes, Osteoporosis, Hypoglycemia, Paget's disease, cancer, Anemia, Neutropenia, Hepatitis C, and Hyperuricemia, Rheumatoid arthritis, hepatitis A and B, Arthritis, colitis, Crohn's, psoriasis, ankylosing spondylitis, Ulcerative colitis.

In one embodiment of the present invention the protein is an antibody.

In a preferred embodiment of the present invention is the antibody an IgG antibody.

In the present invention, the antibody molecule includes any molecule, so long as it comprises the Fc region of an antibody. Examples include an antibody, an antibody fragment, a fusion protein comprising an Fc region, and the like.

The antibody is a protein which is produced in the living body by immune reaction as a result of exogenous antigen stimulation and has an activity to specifically bind to the antigen. Examples of the antibody include an antibody secreted by a hybridoma cell prepared from a spleen cell of an animal immunized with an antigen; an antibody prepared by a genetic recombination technique, namely an antibody obtained by introducing an antibody gene-inserted antibody expression vector into a host cell; and the like. Specific examples include an antibody produced by a hybridoma, a humanized antibody, a human antibody and the like.

A hybridoma is a cell which is obtained by cell fusion between a B cell obtained by immunizing a mammal other than human with an antigen and a myeloma cell derived from mouse or the like and can produce a monoclonal antibody having the desired antigen specificity.

Examples of the humanized antibody include a human chimeric antibody, a human CDR-grafted antibody and the like.

A human chimeric antibody is an antibody which comprises an antibody heavy chain variable region (hereinafter referred to as "HV" or "VH", the heavy chain being "H chain") and an antibody light chain variable region (hereinafter referred to as "LV" or "VL", the light chain being "L chain"), both of an animal other than human, a human antibody heavy chain constant region (hereinafter also referred to as "CH") and a human antibody light chain constant region (hereinafter also referred to as "CL"). As the animal other than human, any animal such as mouse, rat, hamster, rabbit or the like can be used, so long as a hybridoma can be prepared therefrom.

The human chimeric antibody can be produced by obtaining cDNA's encoding VH and VL from a monoclonal antibody-producing hybridoma, inserting them into an expression vector for host cell having genes encoding human antibody CH and human antibody CL to thereby construct a human chimeric antibody expression vector, and then introducing the vector into a host cell to express the antibody.

As the CH of human chimeric antibody, any CH can be used, so long as it belongs to human immunoglobulin (hereinafter referred to as "hIg") can be used. But those belonging to the hIgG class are preferable and any one of the subclasses belonging to the hIgG class, such as hIgG1, hIgG2, hIgG3 and hIgG4, can be used. Also, as the CL of human chimeric antibody, any CL can be used, so long as it belongs to the hIg class, and those belonging to the K class or A class can also be used.

A human CDR-grafted antibody is an antibody in which amino acid sequences of CDR's of VH and VL of an antibody derived from an animal other than human are grafted into appropriate positions of VH and VL of a human antibody.

The human CDR-grafted antibody can be produced by constructing cDNA's encoding V regions in which CDR's of VH and VL of an antibody derived from an animal other than human are grafted into CDR's of VH and VL of a human antibody, inserting them into an expression vector for host cell having genes encoding human antibody CH and human antibody CL to thereby construct a human CDR-grafted antibody expression vector, and then introducing the expression vector into a host cell to express the human CDR-grafted antibody.

As the CH of human CDR-grafted antibody, any CH can be used, so long as it belongs to the hIg, but those of the hIgG class are preferable and any one of the subclasses belonging to the hIgG class, such as hIgG1, hIgG2, hIgG3 and hIgG4, can be used. Also, as the CL of human CDR-grafted antibody, any CL can be used, so long as it belongs to the hIg class, and those belonging to the K class or A class can also be used.

A human antibody is originally an antibody naturally existing in the human body, but it also includes antibodies obtained from a human antibody phage library, a human antibody-producing transgenic animal and a human antibody-producing transgenic plant, which are prepared based on the recent advance in genetic engineering, cell engineering and developmental engineering techniques.

Regarding the antibody existing in the human body, a lymphocyte capable of producing the antibody can be cultured by isolating a human peripheral blood lymphocyte, immortalizing it by its infection with EB virus or the like and then cloning it, and the antibody can be purified from the culture.

The human antibody phage library is a library in which antibody fragments such as Fab, single chain antibody and the like are expressed on the phage surface by inserting a gene encoding an antibody prepared from a human B cell into a phage gene. A phage expressing an antibody fragment having the desired antigen binding activity can be recovered from the library, using its activity to bind to an antigen-immobilized substrate as the marker. The antibody fragment can be converted further into a human antibody molecule comprising two full B chains and two full L chains by genetic engineering techniques.

A human antibody-producing transgenic non-human animal is an animal in which a human antibody gene is introduced into cells. Specifically, a human antibody-producing transgenic animal can be prepared by introducing a human antibody gene into ES cell of a mouse, transplanting the ES cell into an early stage embryo of other mouse and then developing it. By introducing a human chimeric antibody gene into a fertilized egg and developing it, the transgenic animal can be also prepared. Regarding the preparation method of a human antibody from the human antibody-producing transgenic animal, the human antibody can be produced and accumulated in a culture by obtaining a human antibody-producing hybridoma by a hybridoma preparation method usually carried out in mammals other than human and then culturing it.

Examples of the transgenic non-human animal include cattle, sheep, goat, pig, horse, mouse, rat, fowl, monkey, rabbit and the like.

Another aspect of the present invention relates to a method for producing an antibody composition, which comprises culturing the mammalian cell according to the present invention in a medium to produce and accumulate an antibody composition in the culture; and recovering the antibody composition from the culture Also, in the present invention, it is preferable that the antibody is an antibody which recognizes a tumor-related antigen, an antibody which recognizes an allergy- or inflammation-related antigen, an antibody which recognizes circulatory organ disease-related antigen, an antibody which recognizes an autoimmune disease-related antigen or an antibody which recognizes a viral or bacterial infection-related antigen, and a human antibody which belongs to the IgG class is preferable.

An antibody fragment is a fragment which comprises the Fc region of an antibody. Examples of the antibody fragment include an H chain monomer, an H chain dimer and the like.

A fusion protein comprising an Fc region is a composition in which an antibody comprising the Fc region of an antibody or the antibody fragment is fused with a protein such as an enzyme, a cytokine or the like.

One embodiment of the present invention relates to a composition comprising the antibody of the present invention, also referred to as antibody composition.

In one embodiment of the present invention shows the antibody or antibody composition high ADCC activity.

In the present invention, the ADCC activity is a cytotoxic activity in which an antibody bound to a cell surface antigen on a tumor cell in the living body activate an effector cell through an Fc receptor existing on the antibody Fc region and effector cell surface and thereby obstruct the tumor cell and the like. The antibody composition of the present invention has potent antibody-dependent cell-mediated cytotoxic activity (ADCC). An antibody having potent antibody-dependent cell-mediated cytotoxic activity is useful for preventing and treating various diseases including cancers, inflammatory diseases, immune diseases such as autoimmune diseases, allergies and the like, circulatory organ diseases and viral or bacterial infections.

In the case of cancers, namely malignant tumors, cancer cells grow. General anti-tumor agents inhibit the growth of cancer cells. In contrast, an antibody having potent antibody-dependent cell-mediated cytotoxic activity can treat cancers by injuring cancer cells through its cell killing effect, and therefore, it is more effective as a therapeutic agent than the general anti-tumor agents.

In immune diseases such as inflammatory diseases, autoimmune diseases, allergies and the like, in vivo reactions of the diseases are induced by the release of a mediator molecule by immunocytes, so that the allergy reaction can be inhibited by eliminating immunocytes using an antibody having potent antibody-dependent cell-mediated cytotoxic activity.

Examples of the circulatory organ diseases include arteriosclerosis and the like. The arteriosclerosis is treated using balloon catheter at present, but circulatory organ diseases can be prevented and treated by inhibiting growth of arterial cells in restricture after treatment using an antibody having potent antibody-dependent cell-mediated cytotoxic activity.

Various diseases including viral and bacterial infections can be prevented and treated by inhibiting proliferation of cells infected with a virus or bacterium using an antibody having potent antibody-dependent cell-mediated cytotoxic activity.

The antibodies or antibody compositions of the present invention may there for be use to treat immune diseases, cancer viral or bacterial infections or other diseases or disorders mentioned above.

The medicament comprising the antibody composition of the present invention can be administered as a therapeutic agent alone, but generally, it is preferable to provide it as a pharmaceutical formulation produced by an appropriate method well known in the technical field of manufacturing pharmacy, by mixing it with at least one pharmaceutically acceptable carrier.

It is desirable to select a route of administration which is most effective in treatment. Examples include oral administration and parenteral administration, such as buccal, tracheal, rectal, subcutaneous, intramuscular, intravenous or the like. In an antibody preparation, intravenous administration is preferable.

The dosage form includes sprays, capsules, tablets, granules, syrups, emulsions, suppositories, injections, ointments, tapes and the like.

Examples of the pharmaceutical preparation suitable for oral administration include emulsions, syrups, capsules, tablets, powders, granules and the like.

Liquid preparations, such as emulsions and syrups, can be produced using, as additives, water; saccharides, such as sucrose, sorbitol, fructose, etc.; glycols, such as polyethylene glycol, propylene glycol, etc.; oils, such as sesame oil, olive oil, soybean oil, etc.; antiseptics, such as p-hydroxybenzoic acid esters, etc.; flavors, such as strawberry flavor, peppermint, etc.; and the like.

Capsules, tablets, powders, granules and the like can be produced using, as additive, fillers, such as lactose, glucose, sucrose, mannitol, etc.; disintegrating agents, such as starch, sodium alginate, etc.; lubricants, such as magnesium stearate, talc, etc.; binders, such as polyvinyl alcohol, hydroxypropylcellulose, gelatin, etc.; surfactants, such as fatty acid ester, etc.; plasticizers, such as glycerine, etc.; and the like.

Examples of the pharmaceutical preparation suitable for parenteral administration include injections, suppositories, sprays and the like.

Injections may be prepared using a carrier, such as a salt solution, a glucose solution, a mixture of both thereof or the like. Also, powdered injections can be prepared by freeze-drying the antibody composition in the usual way and adding sodium chloride thereto.

Suppositories may be prepared using a carrier such as cacao butter, hydrogenated fat, carboxylic acid or the like.

Also, sprays may be prepared using the antibody composition as such or using a carrier which does not stimulate the buccal or airway mucous membrane of the patient and can facilitate absorption of the antibody composition by dispersing it as fine particles.

Examples of the carrier include lactose, glycerol and the like. Depending on the properties of the antibody composition and the carrier, it is possible to produce pharmaceutical preparations such as aerosols, dry powders and the like. In addition, the components exemplified as additives for oral preparations can also be added to the parenteral preparations.

Although the clinical dose or the frequency of administration varies depending on the objective therapeutic effect, administration method, treating period, age, body weight and the like, it is usually 10 µg/kg to 20 mg/kg per day and per adult.

Definitions

General Glycobiology

Basic glycobiology principles and definitions are described in Varki et al. Essentials of Glycobiology, 2nd edition, 2009.

"N-glycosylation" refers to the attachment of the sugar molecule oligosaccharide known as glycan to a nitrogen atom residue of a protein.

"O-glycosylation" refers to the attachment of a sugar molecule to an oxygen atom in an amino acid residue in a protein.

"Galactosylation" means enzymatic addition of a galactose residue to lipids, carbohydrates or proteins.

"Sialylation" is the enzymatic addition of a neuraminic acid residue.

"Neuraminic acid" is a 9-carbon monosaccharide, a derivative of a ketononose.

"Monoantennary" N-linked glycan is a engineered N-glycan consist of the N-glycan core (Manα1-6(Manα1-3)Manβ1-4GlcNAcβ1-4GlcNAcβ1-Asn-X-Ser/Thr) that elongated with a single GlcNAc residue linked to C-2 and of the mannose α1-3. The single GlcNAc residue can be further elongated for example with Gal or Gal and NeuAc residues.

"Biantennary" N-linked glycan is the simplest of the complex N-linked glycans consist of the N-glycan core (Manα1-6(Manα1-3)Manβ1-4GlcNAcβ1-4GlcNAcβ1-Asn-X-Ser/Thr) elongated with two GlcNAc residues linked to C-2 and of the mannose α1-3 and the mannose α1-6. This core structure can then be elongated or modified by various glycan structures.

"Triantennary" N-linked glycans are formed when an additional GlcNAc residue is added to either the C-4 of the core mannose α1-3 or the C-6 of the core mannose α1-6 of the bi-antennary core structure. This structure can then be elongated or modified by various glycan structures.

"Tetraantennary" N-linked glycans are formed when two additional GlcNAc residues are added to either the C-4 of the core mannose α1-3 or the C-6 of the core mannose α1-6 of the bi-antennary core structure. This core structure can then be elongated or modified by various glycan structures.

"Poly-LacNAc" poly-N-acetyllactosamine ([Galβ1-4GlcNAc]n; n≥2).

"Glycoprofiling" means characterization of glycan structures resident on a biological molecule or cell.

"Glycosylation pathway" refers to assembly of the monosaccharides into complex carbohydrates by the stepwise action of a group of enzymes, known as glycosyltransferases.

"Biosynthetic Step" means addition of a monosaccharide to glycan structure

"Glycosyltransferases" are enzymes that catalyze the formation of the glycosidic linkage to form a glycoside. These enzymes utilize 'activated' sugar phosphates as glycosyl donors, and catalyze glycosyl group transfer to a nucleophilic group, usually an alcohol. The product of glycosyl transfer may be an O-, N-, S-, or C-glycoside; the glycoside may be part of a monosaccharide, oligosaccharide, or polysaccharide.

"Glycosylation capacity" means the ability to produce an amount of a specific glycan structure by a given cell or a given glycosylation process.

"Glycoconjugate" is a macromolecule that contains monosaccharides covalently linked to proteins or lipids.

"HEP" is an abbreviation for heparosan. Heparosan (HEP) is a natural sugar polymer comprising (-GlcUA-1,4-GlcNAc-1,4-) re-peats. It belongs to the glycosaminoglycan polysaccharide family and is a negatively charged polymer at physiological pH. It can be found in the capsule of certain bacteria's but it is also found in higher vertebrate where it serves as precursor for the natural polymers heparin and heparan sulphate.

"PEG" is an abbreviation for polyethylene glycol. PEG polymers are generally used for increasing the half-life of therapeutic molecule. With their high hydrodynamic volume, PEG polymers increases the effective size of drugs and thus slows their clearance from the bloodstream via kidney filtration or by shielding the protein drug towards clearance receptors and proteolytical degradation.

"XTEN" is well defined peptide sequences based on a limited subset of amino acids, and assembled into longer repeating sequences. XTEN also increases the size of therapeutic molecules and prolongs their presence in the bloodstream. "GlycoPEGylation" is the process of covalently attaching PEG to glycans of a protein of interest.

"Enzymatic GlycoPEGylation" is the process of covalently attaching PEG to glycans of a protein of interest using a glycosyltransferase and suitable PEGylated glycosyl transfer groups, such as PEGylated NeuAc-CMP molecules.

"Simple(r) glycan structure" is a glycan structure containing fewer mono-saccharides and/or having lower mass and/or having fewer antennae. "Human like glycosylation" means more sialic acids with a2,6 linkage (more a2,6 sialyltransferase enzyme) and/or less sialic acids with a2,3 linkage and/or more N-acetylneuraminic acid (Neu5Ac) and/or less N-glycolylneuraminic acid (Neu5Gc).

"Reconstruction" refers to Inserting exogeneous gene(s) into cells to obtain modified glycostructures. Typically target cells are producing simple glycan structures as result of deconstruction.

"Deconstruction" means obtaining cells producing a simpler glycan structures by single or stacked knock out of glycosyltransferases "Modified glycan profile" refers to change in number, type or position of oligosaccharides in glycans on a given glycoprotein.

More "homogeneous glycosylation" means that the proportion of identical glycan structures observed by glycoprofiling a given protein expressed in one cell is larger than the proportion of identical glycan structures observed by glycoprofiling the same protein expressed in another cell.

General DNA, mol. biol. Any of various techniques used for separating and recombining segments of DNA or genes, commonly by use of a restriction enzyme to cut a DNA fragment from donor DNA and inserting it into a plasmid or viral DNA. Using these techniques, DNA coding for a protein of interest is recombined/cloned (using PCR and/or restriction enzymes and DNA ligases or ligation independent methods such as USER cloning) into a plasmid (known as an expression vector), which can subsequently be introduced into a cell by transfection using a variety of transfection methods such as calcium phosphate transfection, electroporation, microinjection and liposome transfection. Overview and supplementary information and methods for constructing synthetic DNA sequences, insertion into plasmid vectors and subsequent transfection into cells can be found in Ausubel et al, 2003 and/or Sambrook & Russell, 2001.

"Gene" refers to a DNA region (including exons and introns) encoding a gene product, as well as all DNA regions which regulate the production of the gene product, whether or not such regulatory sequences are adjacent to coding and/or transcribed sequences or situated far away from the gene which function they regulate. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, and locus control regions.

"Targeted gene modifications", "gene editing" or "genome editing" Gene editing or genome editing refer to a process by which a specific chromosomal sequence is changed. The edited chromosomal sequence may comprise an insertion of at least one nucleotide, a deletion of at least one nucleotide, and/or a substitution of at least one nucleotide. Generally, genome editing inserts, replaces or removes nucleic acids from a genome using artificially engineered nucleases such as Zinc finger nucleases (ZFNs), Transcription Activator-Like Effector Nucleases (TALENs), the CRISPR/Cas system, and engineered meganuclease re-engineered homing endonucleases. Genome editing principles are described in Steentoft et al and gene editing methods are described in references therein and also broadly used and thus known to person skilled in the art.

"Endogenous" sequence/gene/protein refers to a chromosomal sequence or gene or protein that is native to the cell or originating from within the cell or organism analyzed.

"Exogenous" sequence or gene refers to a chromosomal sequence that is not native to the cell, or a chromosomal sequence whose native chromosomal location is in a different location in a chromosome or originating from outside the cell or organism analyzed.

"Cleavage" refers to the breakage of the covalent backbone of a DNA molecule.

Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

"Inactivated chromosomal sequence" refer to genome sequence that has been edited resulting in loss of function of a given gene product. The gene is said to be knocked out.

"Heterologous" refers to an entity that is not native to the cell or species of interest.

The terms "nucleic acid" and "polynucleotide" refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogs of natural nucleotides, as well as nucleotides that are modified in the base, sugar and/or phosphate moieties (e.g., phosphorothioate backbones). In general, an analog of a particular nucleotide has the same base-pairing specificity; i.e., an analog of A will base-pair with T.

The term "nucleotide" refers to deoxyribonucleotides or ribonucleotides. The nucleotides may be standard nucleotides (i.e., adenosine, guanosine, cytidine, thymidine, and uridine) or nucleotide analogs. A nucleotide analog refers to a nucleotide having a modified purine or pyrimidine base or a modified ribose moiety. A nucleotide analog may be a naturally occurring nucleotide (e.g., inosine) or a non-naturally occurring nucleotide.

The terms "polypeptide" and "protein" are used interchangeably to refer to a polymer of amino acid residues. These terms may also refer to glycosylated variants of the "polypeptide" or "protein", also termed "glycoprotein". "polypeptide", "protein" and "glycoprotein" is used interchangeably throughout this disclosure.

The term "recombination" refers to a process of exchange of genetic information between two polynucleotides. For the purposes of this disclosure, "homologous recombination" refers to the specialized form of such exchange that takes place, for example, during repair of double-strand breaks in cells. This process requires sequence similarity between the two polynucleotides, uses a "donor" or "exchange" molecule to template repair of a "target" molecule (i.e., the one that experienced the double-strand break), and is variously known as "non-crossover gene conversion" or "short tract gene conversion," because it leads to the transfer of genetic information from the donor to the target. Without being bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized homologous recombination often results in an alteration of the sequence of the target molecule such that part or all of the sequence of the donor polynucleotide is incorporated into the target polynucleotide.

As used herein, the terms "target site" or "target sequence" refer to a nucleic acid sequence that defines a portion of a chromosomal sequence to be edited and to which a targeting endonuclease is engineered to recognize, bind, and cleave.

"Targeted integration" is the method by which exogenous nucleic acid elements are specifically integrated into defined loci of the cellular genome. Target specific double stranded breaks are introduced in the genome by genome editing nucleases that allow for integration of exogenously delivered donor nucleic acid element into the double stranded break site. Thereby the exogenously delivered donor nuclei acid element is stably integrated into the defined locus of the cellular genome.

Sequence identity Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the GenBank website. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EXAMPLES

Example 1

Determining the Glycosyltransferase Repertoire Expressed in a Mammalian CHO Cell Line.

CHO-K1 was obtained from ATCC and CHO-GS (CHOZN GS$^{-/-}$ (Glutamine Synthase) clone produced by ZFN KO) was obtained from Sigma-Aldrich, St. Louis, Mo. All CHO media, supplements and other reagents used were obtained from Sigma-Aldrich unless otherwise specified. CHO-GS cells were maintained as suspension cultures in EX-CELL CHO CD Fusion serum and animal component free media, supplemented with 4 mM L-glutamine. CHO cells were seeded at 0.25×10$^6$ cells/ml in 6 well plate and harvested at exponential phase 48h post inoculation for total RNA extraction with RNeasy mini kit (Qiagen). RNA intergrity and quality were checked by 2100-Bioanalyser (Agilent Technologies). Library construction and next generation sequencing was performed using Illumina HiSeq 2000 System (Illumina, USA) under standard conditions as recommended by the RNAseq service provider. The aligned data was used to calculate the distribution of reads on CHO reference genes and coverage analysis was performed. Only alignment results that passed QC were used for downstream gene expression analysis.

RNAseq analysis was performed on two common CHO lines (CHO-K1, CHO-GS) and two independent CHO-GS triple mgat4a/4b/5 KO clones (ZFN91-1C8, ZFN91-2A6) (TABLE 3). The reported RNAseq analysis of CHO-K1 was included for reference, and this was largely similar to our analyses except that the relative expression levels were higher. Importantly, a few genes including e.g. galnt1 and mgat4b, which was reported not to be expressed in CHO-K1 previously (Xu, Nagarajan et al. 2011), were found to be expressed. Moreover, in the case of mgat4b this gene was found to be essential for the glycoengineering experiments carried out here.

An important observation of the analysis of CHO transcriptomes was that the expression profiles of glycogenes in the two triple KO clones analyses were identical to those of the parental CHO lines, demonstrating that the targeted ko gene editing performed in the CHO cell lines did not alter expression of other glycosyltransferase genes.

Example 2

Gene Inactivation of Glycosyltransferase Genes in the N-Glycosylation Pathway (Deconstruction).

All the glycosyltransferase gene targeted inactivation were performed in CHO-GS and/or in CHO-K1 and cells were grown as described in Example 1. Cells were seeded at $0.5 \times 10^6$ cells/mL in T25 flask (NUNC, Denmark) one day prior to transfection. $2 \times 10^6$ cells and 2 µg endotoxin free plasmid DNA of each ZFN (Sigma, USA) were used for transfection. Each ZFN was tagged with GFP and Crimson by a 2A linker (Duda, Lonowski et al. 2014). Transfections were conducted by electroporation using Amaxa kit V and program U24 with Amaxa Nucleofector 2B (Lonza, Switzerland). Electroporated cells were subsequently plated in 3 mL growth media in a 6-well plate. Cells were moved to 30° C. for a 24h cold shock. 72h post nucleofection the 10-15% highest labeled cell pool for both GFP and Crimson were enriched by FACS. We utilized recent developed methods for enriching KO clones by FACS (GFP/Crimson tagged ZFNs) (Duda, Lonowski et al. 2014) and high throughput screening by an amplicon labeling strategy (IDAA) (Zhang, Steentoft et al. submitted). Cells were single cell FACS sorted again one week later to obtain single clones in round bottom 96 well plates. KO clones were identified by IDAA, and when possible also by immunocytology with appropriate lectins and monoclonal antibodies. Selected clones were further verified by TOPO cloning of PCR products (Invitrogen, US) for in detail Sanger sequencing characterization of mutations introduced in individual TOPO clones. The strategy enabled fast screening and selection of KO clones with appropriate inactivation mutations as outlined herein, and on average we selected 2-5 clones from each targeting event.

The majority of KO clones exhibited out of frame causing insertions and/or deletions (indels) in the range of ±20 bps, and most targeted genes were present with two alleles, while some (mgat4B and mgat5) were present with 1 or 3 alleles, respectively (TABLE 4).

TABLE 4 lists all individual and stacked glycosyltransferase gene inactivation events and the order (ancestry line) of stacking of glycosyltransferase gene inactivation in cells to produce a deconstruction matrix of the N-glycosylation pathway.

Example 3

Gene Insertion of Glycosyltransferase Genes in the N-Glycosylation Pathway (Reconstruction).

Target specific integration (knockin/KI) was directed towards the CHO Safe Harbor #1 locus (S. Bahr et al., BMC Proceedings 2013, 7(Suppl 6):P3.doi:10.1186/1753-6561-7-S6-P3). A modified ObLiGaRe strategy (33) was used where two inverted ZFN binding sites flank the donor plasmid gene of interest to be knocked in. Firstly a shuttle vector designated ObLiGaRe-2X-Ins was synthesized (TABLE 5). ObLiGaRe-2X-Ins was designed in such a way, that any cDNA sequence encoding protein of interest can be inserted into a multiple cloning site where transcription is driven by CMV IE promotor and a BgH terminator. In order to minimize epigenetic silencing, two insulator elements flanking the transcription unit were inserted. In addition an AAVS1 "landing pad" was included at the 3' end of ObLiGaRe-2X-Ins just upstream of the 3' inverted ZFN binding site. A full ST6GAL1 open reading frame was inserted directionally into ObLiGaRe-2X-Ins generating ObLiGaRe-2X-Ins-ST6GAL1 (TABLE 5). Transfection and sorting of clones were performed as described in EXAMPLES 1 and 2. Clones were initially screened by positive SNA lectin staining and selected clones further analyzed by 5' and 3' junction PCR to confirm correct targeted integration event into Safeharbor#1 site in the CHO st3gal4/6 KO clones. The allelic copy number of integration was determined by WT allelic PCR. Subsequently, full human MGAT4A open reading frame was inserted directionally into 2nd allele of Safe Harbor#1 in ST6GAL1 KI clone, followed by inserting full human MGAT5 to AAVS1 "landing pad", which was included at the 3' end of ObLiGaRe-2X-Ins just upstream of the 3' inverted ZFN binding site (TABLE 5).

Example 4

Recombinant Production of Human EPO and IgG in Gene Edited Mammalian CHO Cells.

Expression constructs containing the entire coding sequence of human EPO and a therapeutic IgG cloned into pcDNA3.1/myc-His (C-terminal tags) and pBUDCE4.1 (Invitrogen), respectively, were synthesized by Genewiz, USA. EPO is a 166 amino acid protein with N-glycans at Asn24, Asn38, and Asn83, and IgG has a single N-glycan at Asn297, respectively. Wt or KO CHO cells were transfected with EPO or IgG and maintained at 37° C. as suspension cultures in EX-CELL CHO CD Fusion serum-free media, supplemented with 4 mM L-glutamine and 400 ug/ml Zeocin in 5% $CO_2$ incubator. Clones were scaled up and grown in T75 flasks at a seeding density of $0.5 \times 10^6$ cells/ml, and harvested 72h or 96h later. Cell viability was higher than 90% in all reporter expressing clones and viable cell density are between $2-3 \times 10^6$ cells/ml upon harvest. Cells were removed by centrifugation at 300 g for 5 min, and the supernatant were stored at −80° C. His-tagged recombinant human EPO was purified by nickel affinity purification (Invitrogen, US). Media was mixed 3:1 (v/v) in 4× binding buffer (200 mM Tris, pH 8.0, 1.2 M NaCl) and applied to 0.3 ml packed NiNTA agarose (Invitrogen), pre-equilibrated in binding buffer (50 mM Tris, pH 8.0, 300 mM NaCl). The column was washed with binding buffer and then bound protein was eluted with binding buffer with additional 250 mM imidazole. Fractions containing EPO were determined by SDS-PAGE and further purified on a reverse-phase HPLC purification with a Jupiter C4 column (5 µm, 300 Å, column 250×4.6 mm) (Phenomenex), using 0.1% trifluoroacetic acid (TFA) and a gradient of 10-100% acetonitrile. IgG was purified by HiTrap™ Protein G HP (GE Healthcare, US) pre-equilibrated/washed in PBS and eluted with 0.1 M Glycine (pH 2.7). Purity of protein was evaluated by Coomassie staining of SDS-PAGE gels, and proteins were quantified by BCA Protein Assay Kit (Thermo Scientific, Rockford, US).

Example 4A

Recombinant Production of Human GH and FVII in Gene Edited Mammalian CHO Cells

Four expression constructs containing the entire coding sequence for human GH (hGH) and human Factor VII (hFVII) are cloned into pCGS3 vector (Sigma-Aldrich), that contains a glutamine synthetase (GS) selection cassette. Four hGH constructs carry different individual N-glycosylation sites at L93N, L101T or in combination L93N-L101T and the control without any (hGH WT). The constructs have been described before. Three hFVII constructs have removed different individual N-glycosylation sites at N145Q, N322Q or in combination N145Q_N322Q and the control (hFVII WT). Suspension cells CHO-GS WT, CHO-GS with KO mgat2/4a/4b/5 (allowing production of N-glycans with monoantennary structure), CHO-GS with KO of B3gnt2/mgat4a/4b/5/ST3gal4/6 (allowing production of N-glycans with biantennary structure without poly-LacNAc and without a2,3sia capping), CHO-GS with KI of ST6gal1 in KO of mgat4a/4b/5/ST3gal4/6 (allowing production of N-glycans with biantennary structure without poly-LacNAc and with a2,6sia capping) and CHO-GS with KO of B3gnt2/mgat4a/4b/5 (allowing production of N-glycans with biantennary structure without poly-LacNAc and with a2,3sia capping) are grown in E125 shaker flasks in 30 ml EX-CELL CD CHO medium (Sigma-Aldrich) with 4 mM L-Glutamine (Thermo Fisher Scientific) to a density of 2×10e6 cells/ml. The constructions of the strains are described in EXAMPLE 2 and 3. 2 µg of each construct is transfected into each CHO strain individually with the Nucleofector II device (Kit V, program U-024, LONZA). After nucleofection, the cells are cultivated in 2 ml EX-CELL CD CHO medium 20% conditioned medium and 4 mM L-Glutamine in 6 well plates. 24 hours post transfection 10e5 cells of each transfection sample are transferred to an individual 24 well and cultivated in 500 µl EX-CELL CD CHO medium without L-Glutamine (selection start point). After 10-21 days the cells reach 80% confluence and are splitted 1:5 to a new 24 well ($1^{st}$ split). After 10-14 days the cells reach 80% confluence and are splitted 1:5 to a new 24 well ($2^{nd}$ split). After 7-9 days the cells reach 80% confluence and are splitted 1:10 to a new 24 well ($3^{rd}$ split). Cells are expanded to 6 well format (2 ml culture volume) and T25 flasks (6 ml culture volume) and are then transferred to E125 flasks (30 ml culture volume) for three days cultivation. Each culture is splitted to 0.4×10e6 cells/ml in 30 ml EX-CELL CD CHO medium, with 20% CH CD Efficient Feed B Liquid Nutrient Supplement (Thermo Fisher Scientific) without L-Glutamine and with and without 25 mM MSX in E125 shaker flasks. Vitamin K is added at 5 µg/ml to all hFVII cultures. 7 days after cultivation cells reach densities between 11-1,5×10e6 cells/ml. Cultures are harvested into 50 ml flacon tubes and spin down at 200 g for 5 min. The supernatant is collected and stored at −20 C until further analysis.

The purification methods of hGH and hFVII are described elsewhere (WO 2007026021 A1 and WO 1997010887 A1). N-glycan profiling of purified hGH and hFVII are done like for EPO and IgG in EXAMPLE 5.

Example 5

N-Glycan Profiling of Purified EPO and IgG.

Approximately 25 µg purified EPO was digested with 2 U PNGase F (Roche Diagnostics, Mannheim, Germany) in 50 mM ammonium bicarbonate at 37° C. for overnight. For IgG, 35 µg samples were initially digested (overnight, 37° C.) with trypsin in 50 mM ammonium bicarbonate, and then heated at 95° C. for 15 min and cooled to RT before PNGase F digestion as above. Released N-glycans were separated from intact EPO or IgG tryptic digest using in-house packed Stagetips (Empore disk-C18, 3M) and incubated in 100 mM ammonium acetate, pH 5.0 for 60 min at 22° C. The N-glycans were split in three equal aliquots. One-third was dried in glass vials and permethylated as described previously (Ciucanu and Costello 2003) and the remainder was saved for the native N-glycan analysis. Permethylated N-glycans were extracted with chloroform and desalted by washing the organic phase repeatedly with deionized water. The organic phase was evaporated over a stream of nitrogen gas and the permethylated N-glycans were dissolved in 20 µL 50% (v/v) methanol. Finally, 1 µL sample was co-crystallized with 1 µL matrix composed of 2,5-dihydroxybenzoic acid (10 mg/ml) in 70% (v/v) acetonitrile, 0.1% (v/v) trifluoroacetic acid and 2.5 mM sodium acetate. Permethylated N-glycans were analyzed by positive mode MALDI-TOF (Autoflex Speed, BrukerDaltronics, Bremen) operated in the reflector mode with data acquisition (2000 shots/spot) in the m/z 1000-7000 mass range. Glycan compositional analysis of all spectra was performed by the SysBioWare platform and is presented in Supplementary Table 4 (Vakhrushev, Dadimov et al. 2009). Released native N-glycans were reconstituted in MeOH/$H_2O$ (1/1; v/v, containing 50 mM Ammonium bicarbonate) at the concentration of 0.5 pmol/µl and analyzed on an OrbiTrap Fusion MS (Thermo San Hose, USA). Samples were directly infused via EASY-Spray and analysed by negative ion mode. Flow rate was set to 500 nl/min, spray voltage 1,900-2,100 V, and ion transfer tube temperature 275° C. Precursor ions were selected (isolation width, m/z 3) and subjected to HCD fragmentation at 35% normalized collision energy (default charge state, z=2). All spectra were recorded at resolution 120,000.

Example 6

Inactivation of Glycosyltransferase Genes by Tandem Single Stranded Oligo Deoxy Nucleotide (ssODN)/ZFN Precise Multi Exon Gene Editing.

In this example, gene inactivation is performed by eliminating exons encoding the N-terminal cytoplasmic tail, transmembrane region, and parts of the stem region of the targeted glycosyltransferase gene. The target region deletion is mediated by use of the tandem single stranded oligo deoxy nucleotide (ssODN)/ZFN approach (Duda, Lonowski et al. 2014). The ZFN target site is selected in or as close as possible around the sequence coding for the transmembrane region of the glycosyltransferase. As an example CHO mgat4a is targeted using CHO mgat4a ComposR ZFN's (Sigma) and an ssODN possessing 60 bp homology arm sequences flanking the 5' UTR region including translational start site and 3' flanking mgat4a exon2 ZFN target site (mgata ssODN: gagagagattggtcttgcttgtcatcaccaacgtat-gaaccagtgtgatggtgaaatgagtcGCCGTGCAGGA GCAGCAACTAACGGAAGTAACACTGCATTGACTA-CATTTTCAGGTAC) (SEQ ID NO:54) (5' UTR region shown in lower case, partial ZFN cut site in lower case italics and 3' flanking exons 2 ZFN binding site in upper case), thus removing the exon 1-2 encoding cytoplasmic tail, transmembrane domain and stem of mgat4a. Gene inactivation is performed in CHO-GS as described in Example 2 including mgata ssODN. Transfections were conducted by electroporation using Amaxa kit V and program U24 with Amaxa Nucleofector 2B (Lonza, Switzerland). Electroporated cells were subsequently placed in 3 mL growth media in a 6-well plate. Cells were moved to 30° C. for a 24h cold shock. 72h post nucleofection the 10-15% highest labeled cell pool for both GFP and Crimson were enriched by FACS. Cells were single cell FACS sorted again one week later to obtain single clones in round bottom 96 well plates. Enrichment of KO clones was performed by FACS (GFP/Crimson tagged ZFNs). Clones are analyzed by PCR using primers Mgataex1F (5'-TATCCACTGTGTTGCTTGCTG-3') (SEQ ID NO:55)/Mgataex2R (5'-Actgctcttccagaggtcctg d-3') (SEQ ID NO:56), only detecting correctly target deleted clones. Mono/bi-allelic targeting was determined by PCR wt allele presence detection using primers Mgataex2F (5'-gaacgccttcgaatagctgaacatagg-3') (SEQ ID NO:57)/ Mgataex2R. Genetic PCR results are validated by Southern blot analysis using an intron2 specific probe detecting correct removal of 37 KBp intron1 target region carrying diagnostic Kpn1 sites.

Example 7

Inactivation of Glycosyltransferase Genes by Multi-Exon Dual CRISPR/Cas9 Gene Editing.

Gene inactivation is ensured by removal of exons encoding the cytoplasmic tail/transmembrane and parts of the stem encoded sequences of the desired gene needed to be inactivated. Target region deletion is mediated by use of a pairs of CRISPR/Cas9-gRNAs targeting the flanking regions encoding Mgat4a signal sequence, transmembrane anchoring and stem-regions. CHO Mgat4a is targeted using CHO Mgat4a CRISPR/Cas9 gRNA's Mgat4aEx1gRNA (5'-GGTATACCACATGGCAAAATGGG-3') (SEQ ID NO:58) specific for exon1 andMgat4aEx2gRNA (5'-GTC-CAACAGTTTCGCCGTGCAGG-3') (SEQ ID NO:59) specific for exon2. Both gRNA's were cloned into the BbsI (NEB, USA) gRNA target site of px458 (Addgene, USA) encoding GFP tagged *S. pyogenes* Cas9 and U6 promoter driven gRNA casette, generating px458-CRISPR-Mgat4aex1gRNA and px458-CRISPR-Mgat4aex2gRNA. Precise gene editing by nucleofection using 2 ug of these CRISPR/Cas9-Mgat4a editing tools and target selection validation was performed in CHO-GS cells as described in Examples 2 and 6.

Example 8

Enzymatic GlycoPEGylation of Glycoproteins Monoantennary N-Glycans.

Figure 21:
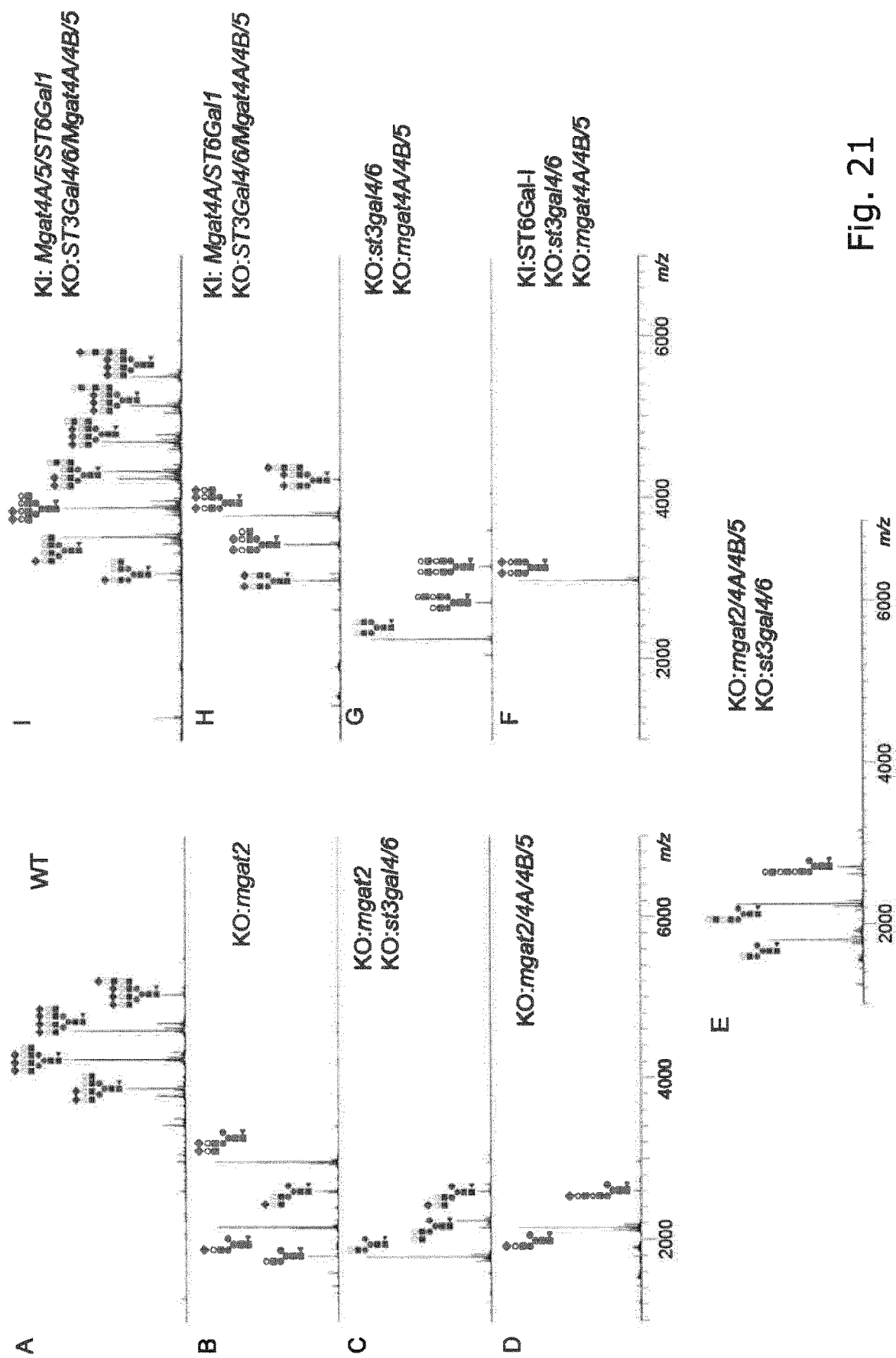
FIG. 21 Glycoprofiling of EPO expressed in CHO with KO of Mgat2 showing loss of tetra and triantennary N-glycan structures and appearance of mono and biantennary N-glycans with galactose and NeuAc capping (PANEL B), and without sialic acid capping with KO of st3gal4/6 (PANEL C). Further KO of mgat4A/4B/5 resulted in monoantennary structures with minor amounts of poly-LacNAc (PANELS D and E). Reintroduction of human MGAT4A and MGAT5 in combination with ST6Gal-I resulted in loss of monoantennary N-glycans and restoration of tri and tetraantennary structures (PANELS H and I).
Figure 22:
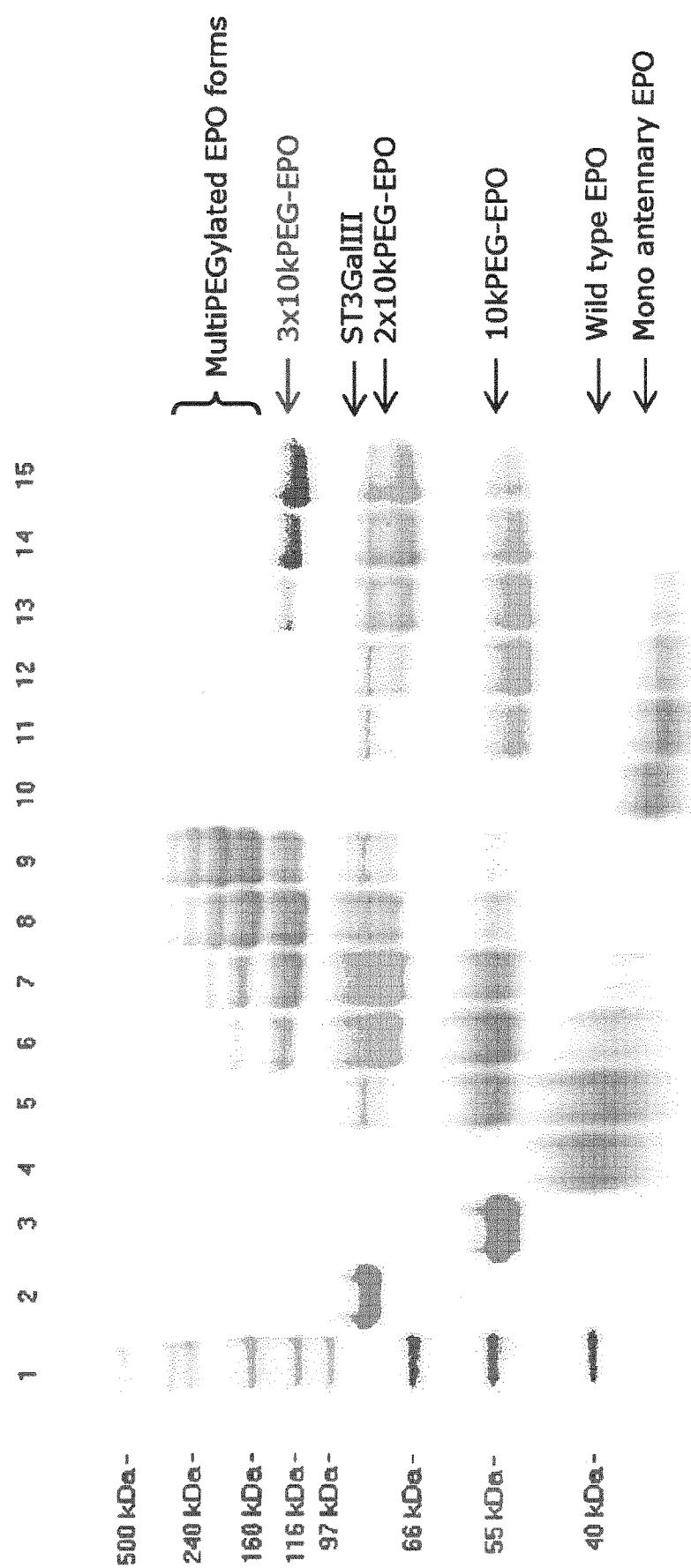
FIG. 22 SDS-PAGE gel analysis of glycoPEGylation reactions of recombinant wildtype EPO-Myc-His6 and recombinant EPO-Myc-His6 with monoantennary N-glycans. Lanes contained: (1) HiMark Standard, (2) ST3Gal3, (3) Sialidase, (4) wt hEPO, wt EPO-Myc-His6 glycoPEGylated with ST3Gal-III and (5) 1×, (6) 5×, (7) 10×, (8) 25×, (9) 50×10 kDa-PSC reagent respectively, (10) EPO-Myc-His6 glycosylation variant and EPO-Myc-His6 glycosylation variant glycoPEGylated with ST3Gal-III and (11) 1×, (12) 5×, (13) 10×, (14) 25×, (15) 50×10 kDa-PSC reagent. Bands above approximately 160 kD indicates GlycoPegylation with more than two PEG chains at one or more N-glycans.
Figure 23:
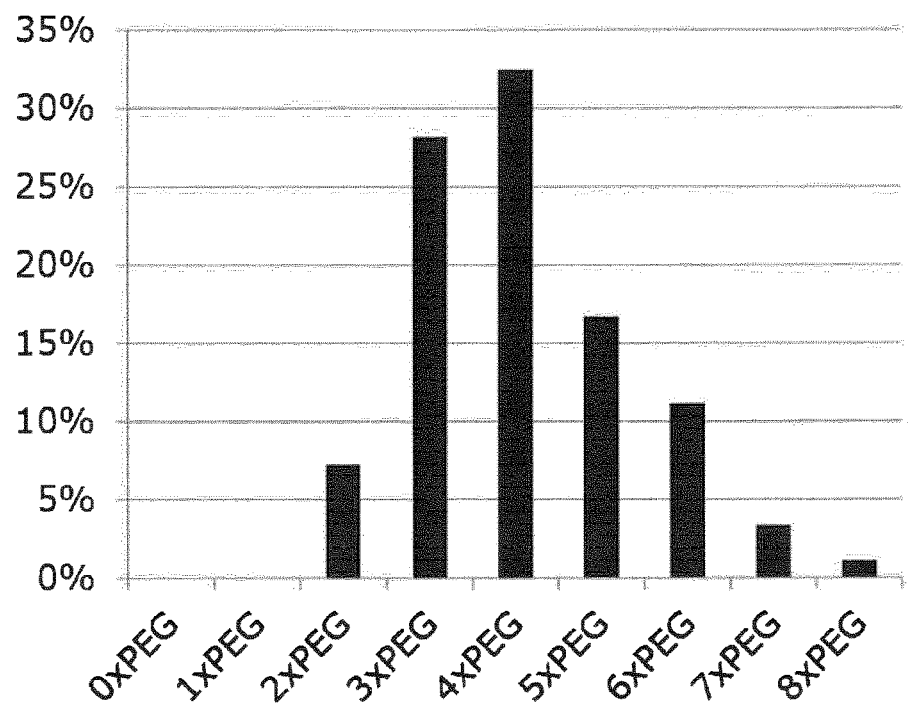
FIG. 23 Quantification of number of attached PEG chains by densitometry of SDS-PAGE gels. (PANEL A) Product profile of enzymatic 10 kDa-GlycoPEGylation reaction with EPO-Myc-His6 produced in ordinary CHO cell lines. (PANEL B) Product profile of enzymatic 10 kDa-GlycoPEGylation reaction with EPO-Myc-His6 produced in Mgat2/4a/4b/5 KO CHO cell lines. Profiles A and B were obtained by densitometry measurements on lane 9 and lane 15 in FIG. 22, respectively.
Figure 23:
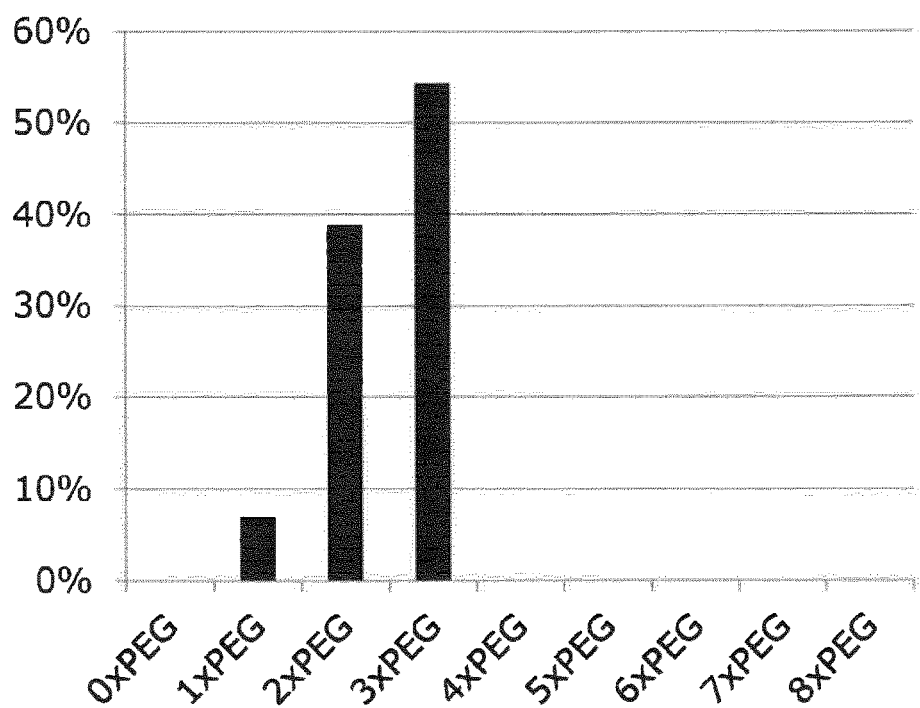

KO of mgat2 in combination with mgat4a/4b/5 in CHO cells resulted in homogeneous monoantennary N-glycans when EPO was expressed (FIG. 21). Reintroduction of human MGAT4A as well as MGAT4A and 5 in combination by knockin resulted in tri and tetraantennary N-glycans, respectively (FIG. 21), demonstrating that the monoantennary N-glycan obtained is linked β1-2 to the α1-3Man branch controlled by mgat1. Enzymatic glycopegylation or transfer of other compounds by sialyltransferases and CMP-(PEG)NeuAc or relevant modified donor was tested using EPO as an example (FIGS. 22-23).

Material and Methods—Glycovariants of EPO-Myc-His6 were produced in CHO with KO mgat2/4a/4b/5 and purified on a nickel-NTA column and buffer exchanged into 100 mM Tris, 150 mM NaCl, 0.005% NaN3, pH 7.2 buffer as described in Example 4. Wild type EPO-Myc-His6 with normal glycosylation profile was produced in non modified CHO cells and in similar way purified on a nickel-NTA column before buffer exchanged into 100 mM Tris, 150 mM NaCl, 0.005% NaN3, pH 7.2 buffer. Protein concentrations were determined by NanoDrop Lite Spectrophotometer (Thermo Scientific™). Sialyltransferase (ST3Gal-III; 1.35 U/ml) in 20 mM HEPES, 120 mM NaCl, 50% glycerol, pH 7.0 stock solution was obtained from FujiFilm Diosynth Biotechnologies, Japan. Sialidase (*Artherobacter urifaciens*) was produced at Novo Nordisk A/S and used as a 200 U/ml stock solution in 20 mM HEPES, 120 mM NaCl, 50% glycerol, pH 7.0. Support bound neuraminidase (*Clostridium perfringens*) on agarose was obtained from Sigma (Cat. # N5254-10UN). The resin was washed extensively in MilliQ water before use. 10k-PSC (cytidine-5'-monophosphoryl-[5-(N-10 kDa-methoxypolyoxyethylene-oxycarboxamido)glycylamido-3,5-dideoxy-D-glycero-n-galacto-2-nonulopyranosuronate], Lot: 3605-A-R0-01-61-1) was obtained from Albany Molecular Research, Inc, Albany, N.Y. 12203, US. 10k-PSC was produced as described in WO03031464. The tris-buffer used in examples below contained 50 mM tris-HCl, 150 mM NaCl, pH 7.6.

SDS-PAGE gel electrophoresis was performed on NuPage precast gels (NuPage 7% Tris-Acetate Gel, 15 wells, Invitrogen cat. No. EA03555BOX) using NuPage Tris-Acetate SDS Running buffer (Invitrogen cat. No. # LA0041). Samples (0.15 mg/ml) were added NuPage Sample Reducing Agent (Invitrogen cat. No. NP0004) and LDS sample buffer (Invitrogen cat. No. NP0008) and heated to 70° C. for 10 min before gel loading. HiMark HMW (Invitrogen cat. No. LC6060) was used as standard. Electrophoresis was performed at 150 V, 120 mA & 25 W for 60 min. Gels were stained with SimplyBlue SafeStain (Invitrogen cat. No. LC5688) according to Invitrogen protocols. Coomasie stained gels were analysed by densitometry using GelQuant software and methods described previously (Rehbein and Schwalbe 2015) (FIG. 23).

HPLC analysis of GlycoPEGylated EPO-Myc-His6 conjugates of the invention was performed as follows. Samples were analysed in non-reduced form. A Zorbax 300SB-C3 column (4.6×50 mm; 3.5 um Agilent, Cat. No.: 865973-909) was used. Column was operated at 30° C. 2.5 ug sample was injected, and column eluted with a water (A)-acetonitrile (B) solvent system containing 0.1% trifluoroacetic acid. The gradient program was as follows: 0 min (25% B); 4 min (25% B); 14 min (46% B); 35 min (52% B); 40 min (90% B); 40.1 min (25% B).

Enzymatic glycoPEGylation of EPO-Myc-His6 variants was performed by either an one-pot method using sialidase in combination with ST3Gal-III, or by a sequential method where the EPO-Myc-His6 variant was first reacted with agarose-neuraminidase gel for 3h at 25° C., then after transferring the supernatant to a fresh vial reacted with the ST3Gal-III and PSC reagent. The one-pot method relies on the fact that *Artherobacter urifaciens* sialidase is unable to desialylate PEGylated sialosides. Use of recombinant glycoproteins with monoantennary N-glycans without sialic acid capping as invented eliminates the need for prior desialylation.

GlycoPEGylation of recombinant human erythropoietin—Recombinant wildtype EPO-Myc-His6 produced in CHO cell lines was dissolved in 100 mM Tris, 150 mM NaCl, 0.005% NaN3 (pH 7.2) to a concentration of 1.17 mg/ml. 10k-PSC reagent (2.0 mg) was dissolved in 100 ul 50 mM Tris-HCl, 150 mM NaCl (pH 7.6) to a concentration of 20 mg/ml. ST3Gal-III and AUS were both dissolved in 20 mM HEPES, 120 mM NaCl, 50% glycerol, pH 7.0 to a volumetric concentration of 1.35 U/ml and 200 U/ml respectively. Reagents were mixed according to scheme below:

|  | Unit | Exp. 1 | Exp. 2 | Exp. 3 | Exp. 4 | Exp. 5 |
| --- | --- | --- | --- | --- | --- | --- |
| wtEPO | ug | 10 | 10 | 10 | 10 | 10 |
| 10k-PSC | eq | 1 | 5 | 10 | 25 | 50 |
| ST3Gal3 | mU/ug wtEPO | 0.196 | 0.196 | 0.196 | 0.196 | 0.196 |
| Sialidase | U/ml | 5 | 5 | 5 | 5 | 5 |
| Tris buffer | ul | 9.0 | 8.4 | 7.6 | 5.3 | 1.3 |
| Final volume | ul | 28.45 | 28.45 | 28.45 | 28.45 | 28.45 |
| Final [wtEPO] | mg/ml | 0.35 | 0.35 | 0.35 | 0.35 | 0.35 |

Reactions were incubated for 18h at 32° C. Samples were then analysed by HPLC and SDS-PAGE (FIG. 22, lanes 5-9).

GlycoPEGylation of erythropoietin produced in CHO cells with KO of mgat2/4A/4B/5—Recombinant wtEPO-Myc-His6 glycosylation variant produced in Mgat2/4a/4b/5 knock-out CHO cell line was dissolved in 100 mM Tris, 150 mM NaCl, pH 7.2 to a concentration of 0.585 mg/ml. 10k-PSC reagent (2.0 mg) was dissolved in 100 ul 50 mM Tris-HCl, 150 mM NaCl, pH 7.6 to a concentration of 20 mg/ml. ST3GalIII and AUS were both dissolved in 20 mM HEPES, 120 mM NaCl, 50% glycerol, pH 7.0 to a volumetric concentration of 1.35 U/ml and 200 U/ml respectively. Reagents were mixed according to scheme below:

|  | Unit | Exp. 1 | Exp. 2 | Exp. 3 | Exp. 4 | Exp. 5 |
| --- | --- | --- | --- | --- | --- | --- |
| EPO-Myc-His6 | ug | 10 | 10 | 10 | 10 | 10 |
| 10k-PSC | eq | 1 | 5 | 10 | 25 | 50 |
| ST3Gal3 | mU/ug EPO | 0.196 | 0.196 | 0.196 | 0.196 | 0.196 |
| Sialidase | U/ml | 5 | 5 | 5 | 5 | 5 |
| Tris buffer | ul | 9.0 | 8.4 | 7.6 | 5.3 | 1.3 |
| Final volume | ul | 28.45 | 28.45 | 28.45 | 28.45 | 28.45 |
| Final [EPO] | mg/ml | 0.35 | 0.35 | 0.35 | 0.35 | 0.35 |

Reactions were incubated for 18h at 32° C. Samples were then analysed by HPLC and SDS-PAGE (FIG. 22, lanes 11-15).

Two step glycoPEGylation reaction of recombinant human erythropoietin—EPO-Myc-His6 (272 ug) in 100 mM Tris, 150 mM NaCl, 0.005% NaN3, pH 7.2 (0.214 mg/ml) was treated with prewashed immobilized sialidase (150 ul suspension, 150 mU) for 3h at room temperature. Resin was then removed by filtration. The filtrate was analysed by LC-MS to confirm formation of asialo EPO-Myc-His6 in monoantennary N-glycan form (calculated mass 25,464.97 Da, analysis 25,465.30 Da).

| Calc. average mass | Found | Assignment |
| --- | --- | --- |
| 26921.23 Da | 26921.53 Da | Penta sialylated EPO-myc-His6 containing 3 mono antennary N-glycanes and one O-glycan |
| 26629.98 Da | 26630.34 Da | Tetra sialylated EPO-myc-His6 containing 3 mono antennary N-glycanes and one O-glycan |
| 26338.72 Da | 26339.16 Da | Tri sialylated EPO-myc-His6 containing 3 mono antennary N-glycanes and one O-glycan |
| 25464.97 Da | 25465.30 Da | Desialylated (neuraminidase treated) EPO-myc-His6 containing 3 mono antennary N-glycanes and one O-glycan |

The filtrate was then added 10k-PSC reagent dissolved in 100 ul 50 mM Tris-HCl, 150 mM NaCl, pH 7.6. ST3Gal-III and AUS were both dissolved in 20 mM HEPES, 120 mM NaCl, 50% glycerol, pH 7.0 to a volumetric concentration of 1.35 U/ml and 200 U/ml respectively. Reagents were mixed according to scheme below:

|  | Unit | Exp. 1 | Exp. 2 | Exp. 3 | Exp. 4 | Exp. 5 |
| --- | --- | --- | --- | --- | --- | --- |
| asialo EPO-Myc-His6 | ug | 20 | 20 | 20 | 20 | 20 |
| 10k-PSC | eq | 1 | 3 | 5 | 10 | 20 |
| St3Gal3 | mU/ug EPO | 0.196 | 0.196 | 0.196 | 0.196 | 0.196 |
| Tris buffer | ul | 14.0 | 12.5 | 11.0 | 7.4 | 0 |
| Final volume | ul | 117.6 | 117.6 | 117.6 | 117.6 | 117.6 |
| Final [EPO] | mg/ml | 0.17 | 0.17 | 0.17 | 0.17 | 0.17 |

Reactions were incubated for 20h at 32° C. Samples were then analysed by HPLC and SDS-PAGE.

Example 9

GlycoPEGylation of Monoantennary N-Glycans FVIIa

Glycovariants of hFVII N145Q, N322Q or in combination N145Q_N322Q and the control (hFVII WT) produced in CHO with KO mgat2/4a/4b/5 are glycoPEGylated on the mono-antennary N-glycan by a 2 step enzymatic process. The FVIIa protein is initially buffer exchanged into a 25 mM HEPES buffer containing approximately 10 mM $CaCl_2$), 100 mM NaCl (pH 7.0). The buffer exchange is performed using a Slide-A-Lyzer cassette (Thermo Scientific) with a 10 kD cut-off. To the FVIIa protein is then added sialidase (1.0 units per mg of FVIIa) and the reaction mixture is incubated at room temperature for an hour. The asialo FVIIa is isolated using the procedure described by Thim, L et al. Biochemistry 1988, 27, 7785-779. FVIIa protein concentration is at this point determined by NanoDrop Lite Spectrophotometer (Thermo Scientific™) against a known FVIIa reference. 5 equivalents of 10k-PSC reagent produced as described in WO03031464 is then added in 50 mM Tris-HCl, 150 mM NaCl (pH 7.6), followed by addition of ST3Gal-III enzyme (0.2 units per mg of asialo FVIIa protein). The reaction is incubated for 18h at 32° C. Excessive 10k-PSC reagent is removed by ion exchange chromatography: the reaction mixture is loaded on to a HiTrap Q ion-exchange column (Amersham Bioscience) pre-equilibrated in 25 mM GlyGly, 50 mM NaCl, pH 8.0. The column is eluded with 25 mM GlyGly, 50 mM NaCl, pH 8.0 (buffer A) over 10 cv; followed by 25 mM GlyGly, 50 mM NaCl, 25 mM $CaCl_2$), pH 8.0 (buffer B) over 15 cv at constant flow and temperature (5° C.). The eluent is monitored by absorbance at 280 nm. Fractions containing protein conjugate are pooled and pH adjusted to 6.0 using 1N HCl. Non pegylated FVIIa is then removed from glycopegylated FVIIa variant(s) by size exclusion chromatography on a Superdex 200 column (Amersham Bioscience) pre-equilibrated in 25 mM GlyGly, 50 mM NaCl, 25 mM $CaCl_2$), pH 6.0. The column is eluted with 25 mM GlyGly, 50 mM NaCl, 25 mM $CaCl_2$), pH 6.0 while monitoring absorbance at 280 nm. Fractions are analysed on SDS-PAGE (4-12% Bis-Tris NuPAGE gels) stained with Simple Blue as described by Invitrogen. Fractions containing PEGylated FVIIa are pooled and concentrated by filtering through an Amicon Ultra™-15 (10K MWCO) centrifuge filter at 4000 rpm, 10° C.

Example 10

GlycoPEGylation of hGH Glycovariant

Glycovariants with individual N-glycosylation sites at L93N, L101T or in combination L93N-L101T of hGH and the control without any (hGH WT) produced in CHO with KO mgat2/4a/4b/5 are glycoPEGylated on the mono-antennary N-glycan by a 2 step enzymatic process similar to the previous example. The hGH protein is initially buffer exchanged into a 25 mM HEPES buffer (pH 7.2). Support bound neuraminidase (*Clostridium perfringens*) on agarose (Sigma Cat. # N5254-10UN) is added and the reaction mixture is incubated at room temperature for one hour. The agarose support is then filtered off, and the hGH protein is added 10k-PSC (WO03031464) reagent (5 equivalents relative to hGH protein) followed by ST3Gal-III enzyme (0.2 units per mg of hGH protein). The reaction is incubated for 18h at 32° C. The glycoPEGylated hGH protein is isolated by a combination of anionic exchange and size exclusion chromatography as described in the previous example. Fractions are analysed on SDS-PAGE stained with Simple Blue as described by Invitrogen. Fractions containing PEGylated hGH are pooled and concentrated by filtering through an Amicon Ultra™-15 (10K MWCO) centrifuge filter at 4000 rpm, 10° C. The glycoPEGylated hGH protein can alternatively be purified by RP-HPLC as described by da Silva Freitas et al. Bioconjugate Chem. 2013, 24, 456-463.

TABLE 4

ZFN design and sequence analysis of CHO glycoengineered clones.

| Clone | Inser & Del | Alignment |
|---|---|---|
| KO:mgat4A | | |
| mgat4A-WT | ZFN | TTCTGAGTTGAA<u>TGCCATTGTCCAACA</u>gtt------------<br>tc<u>GCCGTGCAGGAG</u>CAGCAACTAACGGAAG (SEQ ID NO: 9) |
| mgat4A-alle1 | -5 bp | TTCTGAGTTGAATGCCATTGTCCAACAg-----------------<br>CCGTGCAGGAGCAGCAACTAACGGAAG (SEQ ID NO: 10) |
| mgat4A-alle2 | +13 bp | TTCTGAGTTGAATGCCATTGTCCAACAgttGAATTCTAGATGAtcGCCGTGCAGG<br>AGCAGCAACTAACGGAAG (SEQ ID NO: 11) |
| KO:mgat4A/4B | | |
| mgat4A-WT | ZFN | TTCTGAGTTGAA<u>TGCCATTGTCCAACA</u>gtt------------<br>tc<u>GCCGTGCAGGAG</u>CAGCAACTAACGGAAG (SEQ ID NO: 9) |
| mgat4A-alle1 | -5 bp | TTCTGAGTTGAATGCCATTGTCCAACAg-----------------<br>CCGTGCAGGAGCAGCAACTAACGGAAG (SEQ ID NO: 10) |
| mgat4A-alle2 | +13 bp | TTCTGAGTTGAATGCCATTGTCCAACAgttGAATTCTAGATGAtcGCCGTGCAGG<br>AGCAGCAACTAACGGAAG (SEQ ID NO: 11) |
| mgat4B-WT | ZFN | <u>GCCCTCCAGCAGCCCTCT</u>gagga<u>CTGGATGATCCTGGAGTT</u> (SEQ ID NO: 12) |
| mgat4B-alle1 | -7 bp | GCCCTCCAGCAGCCCTCTg-------GATGATCCTGGAGTT (SEQ ID NO: 13) |
| KO:mgat5 | | |
| mgat5-WT | ZFN | GGGGGATGATGCTTCTGCACTTCACCATCCAg--------------<br>cagcgGACTCAGCCTGAGAGCAGCTCCATGTT (SEQ ID NO: 17) |
| mgat5-alle1 | +14 bp | GGGGGATGATGCTTCTGCACTTCACCATCCAgcaTGAATTCTAGATGAgcgGACT<br>CAGCCTGAGAGCAGCTCCATGTT (SEQ ID NO: 18) |
| mgat5-alle2 | -1 bp | GGGGGATGATGCTTCTGCACTTCACCATCCAg---------------<br>agcgGACTCAGCCTGAGAGCAGCTCCATGTT (SEQ ID NO: 19) |
| mgat5-alle3 | +61 bp | GGGGGATGATGCTTCTGCACTTCACCATCCAgcag (SEQ ID NO: 20)-----<br>(+61 bp)--cgGACTCAGCCTGAGAGCAGCTCCATGTT (SEQ ID NO: 21) |
| KO:mgat4A/4B/5 | | |
| mgat4A-WT | ZFN | TTCTGAGTTGAA<u>TGCCATTGTCCAACA</u>gtt------------<br>tc<u>GCCGTGCAGGAG</u>CAGCAACTAACGGAAG (SEQ ID NO: 9) |
| mgat4A-alle1 | -5 bp | TTCTGAGTTGAATGCCATTGTCCAACAg-----------------<br>CCGTGCAGGAGCAGCAACTAACGGAAG (SEQ ID NO: 10) |
| mgat4A-alle2 | +13 bp | TTCTGAGTTGAATGCCATTGTCCAACAgttGAATTCTAGATGAtcGCCGTGCAGG<br>AGCAGCAACTAACGGAAG (SEQ ID NO: 11) |
| mgat4B-WT | ZFN | <u>GCCCTCCAGCAGCCCTCT</u>gagga<u>CTGGATGATCCTGGAGTT</u> (SEQ ID NO: 12) |
| mgat4B-alle1 | -7 bp | GCCCTCCAGCAGCCCTCTg-------GATGATCCTGGAGTT (SEQ ID NO: 13) |
| mgat5-WT | ZFN | GGGGGATGATGC<u>TTCTGCACTTCACCATCCA</u>g----<br>cagcg<u>GACTCAGCCTGAGAGCAGCT</u>CCATGTT (SEQ ID NO: 17) |

TABLE 4-continued

ZFN design and sequence analysis of CHO glycoengineered clones.

| Clone | Inser & Del | Alignment |
|---|---|---|
| mgat5-alle1 | +4 bp | GGGGGATGATGCTTCTGCACTTCACCATCCAgcagcCAGCgGACTCAGCCTGAGAGCAGCTCCATGTT (SEQ ID NO: 62) |
| mgat5-alle2 | -4 bp | GGGGGATGATGCTTCTGCACTTCACCATCCAg--------gGACTCAGCCTGAGAGCAGCTCCATGTT (SEQ ID NO: 63) |
| mgat5-alle3 | -16 bp | GGGGGATGATGCTTCTGCACTTC--------------------CTCAGCCTGAGAGCAGCTCCATGTT (SEQ ID NO: 64) |
| KO:B3gnt1 | | |
| B3gnt1-WT | ZFN | <u>TGCAGCTGCTCTACCTGTC</u>-----------gctgc<u>TCTCCGGACTGCACG</u> (SEQ ID NO: 25) |
| B3gnt1-alle1 | +11 bp | TGCAGCTGCTCTACCTGTCgcagcTGCTCTACCTGTCTCCGGACTGCACG (SEQ ID NO: 26) |
| B3gnt1-alle2 | -5 bp | TGCAGCTGCTCTACCTGTC----------------TCTCCGGACTGCACG (SEQ ID NO: 27) |
| KO:B3gnt2 | | |
| B3gnt2-WT | ZFN | <u>TTCAGCCCTTCC</u>cgggc<u>GTACTGGAACAGAGAGCA</u> (SEQ ID NO: 28) |
| B3gnt2-alle1 | -1 bp | TTCAGCCCTTCC-gggcGTACTGGAACAGAGAGCA (SEQ ID NO: 29) |
| B3gnt2-alle2 | -4 bp | TTCAGCCCTTCCcg----TACTGGAACAGAGAGCA (SEQ ID NO: 30) |
| KO:B4galt1 | | |
| B4galt1-WT | ZFN | TGCATCCGGTCCTACAGCgccagc----AACTGGACTATGGTA (SEQ ID NO: 31) |
| B4galt1-alle1 | -4 bp | TGCATCCGGTCCTACAGCgccagcCAGCAACTGGACTATGGTA (SEQ ID NO: 32) |
| KO:B4galt2 | | |
| B4galt2-WT | ZFN | <u>CAGCCCCGCCACTTT</u>gcc -----------atc<u>GCCATGGACAAGTTTGGCT</u> (SEQ ID NO: 33) |
| B4galt2-alle1 | +73 bp | CAGCCCCGCCACTTTgcc (SEQ ID NO: 34)--(+73 bp)--atcGCCATGGACAAGTTTGGCT (SEQ ID NO: 35) |
| KO:B4galt3 | | |
| B4galt3-WT | ZFN | <u>CTAGCCCTCAAGTCAGGA</u>tgt------tg<u>CGGAGGCTGCTGGAGAGG</u> (SEQ ID NO: 36) |
| B4galt3-alle1 | +5 bp | CTAGCCCTCAAGTCAGGAtgtCGTGTtgCGGAGGCTGCTGGAGAGG (SEQ ID NO: 37) |
| B4galt3-alle2 | +2 bp | CTAGCCCTCAAGTCAGGAtgt---tgCCCGGAGGCTGCTGGAGAGG (SEQ ID NO: 38) |
| KO:B4galt4 | | |
| B4galt4-WT | ZFN | <u>AACTGGGACTGCTTT</u>at----attc<u>CACGATGTGGACCTGGTG</u> (SEQ ID NO: 39) |
| B4galt4-alle1 | +1 bp | AACTGGGACTGCTTTat---TattcCACGATGTGGACCTGGTG (SEQ ID NO: 40) |
| B4galt4-alle2 | +2 bp | AACTGGGACTGCTTTatattTATTcCACGATGTGGACCTGGTG (SEQ ID NO: 41) |
| KO:B4galt1/2 | | |
| B4galt1-WT | ZFN | <u>TGCATCCGGTCCTACAGC</u>gccagc----<u>AACTGGACTATGGTA</u> (SEQ ID NO: 31) |
| B4galt1-alle1 | +4 bp | TGCATCCGGTCCTACAGCgccagcCAGCAACTGGACTATGGTA (SEQ ID NO: 32) |
| B4galt2-WT | ZFN | <u>CAGCCCCGCCACTTT</u>gccatc<u>GCCATGGACAAGTTTGGCT</u> (SEQ ID NO: 33) |
| B4galt2-alle1 | -8 bp | CAGCCCCGCCAC--------cGCCATGGACAAGTTTGGCT (SEQ ID NO: 65) |
| B4galt2-alle2 | -14 bp | CAGCCC--------------cGCCATGGACAAGTTTGGCT (SEQ ID NO: 66) |
| KO:st3Gal3 | | |
| st3Gal3-WT | ZFN | <u>CTCTCTCTTTGTCCTTGCT</u>ggctt<u>CAAATGGCAGGACTTCAAG</u> (SEQ ID NO: 42) |

TABLE 4-continued

ZFN design and sequence analysis of CHO glycoengineered clones.

| Clone | Inser & Del | Alignment |
|---|---|---|
| st3Gal3-alle1 | -5 bp | CTCTCTCTTTGTCCTTGCt-----CAAATGGCAGGACTTCAAG (SEQ ID NO: 43) |
| st3Gal3-alle2 | -1 bp | CTCTCTCTTTGTCCTTGCtggct-CAAATGGCAGGACTTCAAG (SEQ ID NO: 44) |

KO:st3Gal4

| Clone | Inser & Del | Alignment |
|---|---|---|
| st3Gal4-WT | ZFN | GGCAGCCTCCAGTGTCGTCgttgt----gTTGTGGTGGGGAATGGGC (SEQ ID NO: 45) |
| st3Gal4-alle1 | +4 bp | GGCAGCCTCCAGTGTCGTCgttgtTTGTgTTGTGGTGGGGAATGGGC (SEQ ID NO: 46) |
| st3Gal4-alle2 | -4 bp | GGCAGCCTCCAGTGTCGTCg--------gTTGTGGTGGGGAATGGGC (SEQ ID NO: 47) |

KO:st3Gal6

| Clone | Inser & Del | Alignment |
|---|---|---|
| st3Gal6-WT | ZFN | CGGTACCTCTGATTTTGCTttgccCTATGGGACAAGGCC (SEQ ID NO: 48) |
| st3Gal6-alle1 | -4 bp | CGGTACCTCTGATTTTGCTt----CTATGGGACAAGGCC (SEQ ID NO: 49) |
| st3Gal6-alle2 | -22 bp | CGGTACCTCTGA----------------------AGGCC (SEQ ID NO: 50) |

KO:st3Gal3/4

| Clone | Inser & Del | Alignment |
|---|---|---|
| st3Gal3-WT | ZFN | CTCTCTCTTTGTCCTTGCtggcttCAAATGGCAGGACTTCAAG (SEQ ID NO: 42) |
| st3Gal3-alle1 | -5 bp | CTCTCTCTTTGTCCTTGCt-----CAAATGGCAGGACTTCAAG (SEQ ID NO: 43) |
| st3Gal3-alle2 | -1 bp | CTCTCTCTTTGTCCTTGCtggct-CAAATGGCAGGACTTCAAG (SEQ ID NO: 44) |
| st3Gal4-WT | ZFN | GGCAGCCTCCAGTGTCGTCgttgt-----gTTGTGGTGGGGAATGGGC (SEQ ID NO: 45) |
| st3Gal4-alle1 | -4 bp | GGCAGCCTCCAGTGTCGTCg---------gTTGTGGTGGGGAATGGGC (SEQ ID NO: 67) |
| st3Gal4-alle2 | +5 bp | GGCAGCCTCCAGTGTCGTCgACACGttgtgTTGTGGTGGGGAATGGGC (SEQ ID NO: 69) |

KO:st3Gal4/6

| Clone | Inser & Del | Alignment |
|---|---|---|
| st3Gal4-WT | ZFN | GGCAGCCTCCAGTGTCGTCgttgt----gTTGTGGTGGGGAATGGGC (SEQ ID NO: 45) |
| st3Gal4-alle1 | +4 bp | GGCAGCCTCCAGTGTCGTCgttgtTTGTgTTGTGGTGGGGAATGGGC (SEQ ID NO: 46) |
| st3Gal4-alle2 | -4 bp | GGCAGCCTCCAGTGTCGTCg--------gTTGTGGTGGGGAATGGGC (SEQ ID NO: 47) |
| st3Gal6-WT | ZFN | CGGTACCTCTGATTTTGCT-ttgccCTATGGGACAAGGCC (SEQ ID NO: 48) |
| st3Gal6-alle1 | +1 bp | CGGTACCTCTGATTTTGCTTttgccCTATGGGACAAGGCC (SEQ ID NO: 70) |
| st3Gal6-alle2 | -7 bp | CGGTACCTCTGATTTTG--------CTATGGGACAAGGCC (SEQ ID NO: 72) |

KO:B3gnt2/mgat4A/4B/5

| Clone | Inser & Del | Alignment |
|---|---|---|
| mgat4A-WT | ZFN | TTCTGAGTTGAATGCCATTGTCCAACAgtt-------------tcGCCGTGCAGGAGCAGCAACTAACGGAAG (SEQ ID NO: 9) |
| mgat4A-alle1 | -5 bp | TTCTGAGTTGAATGCCATTGTCCAACAg-----------------CCGTGCAGGAGCAGCAACTAACGGAAG (SEQ ID NO: 10) |
| mgat4A-alle2 | +13 bp | TTCTGAGTTGAATGCCATTGTCCAACAgttGAATTCTAGATGAtcGCCGTGCAGGAGCAGCAACTAACGGAAG (SEQ ID NO: 11) |
| mgat4B-WT | ZFN | GCCCTCCAGCAGCCCTCTgaggaCTGGATGATCCTGGAGTT (SEQ ID NO: 12) |
| mgat4B-alle1 | -7 bp | GCCCTCCAGCAGCCCTCTg-------GATGATCCTGGAGTT (SEQ ID NO: 13) |
| mgat5-WT | ZFN | GGGGGATGATGCTTCTGCACTTCACCATCCAg----cagcgGACTCAGCCTGAGAGCAGCTCCATGTT (SEQ ID NO: 17) |
| mgat5-alle1 | +4 bp | GGGGGATGATGCTTCTGCACTTCACCATCCAgcagcCAGCgGACTCAGCCTGAGAGCAGCTCCATGTT (SEQ ID NO: 62) |
| mgat5-alle2 | -4 bp | GGGGGATGATGCTTCTGCACTTCACCATCCAg--------gGACTCAGCCTGAGAGCAGCTCCATGTT (SEQ ID NO: 63) |
| mgat5-alle3 | -16 bp | GGGGGATGATGCTTCTGCACTTC--------------------CTCAGCCTGAGAGCAGCTCCATGTT (SEQ ID NO: 64) |

TABLE 4-continued

ZFN design and sequence analysis of CHO glycoengineered clones.

| Clone | Inser & Del | Alignment |
|---|---|---|
| B3gnt2-WT | ZFN | <u>TTCAGCCCTTCC</u>--cgggc<u>GTACTGGAACAGAGAGCA</u> (SEQ ID NO: 28) |
| B3gnt2-alle1 | +2 bp | TTCAGCCCTTCCCCcgggcGTACTGGAACAGAGAGCA (SEQ ID NO: 73) |
| B3gnt2-alle2 | +1 bp | TTCAGCCCTTCCC-cgggcGTACTGGAACAGAGAGCA (SEQ ID NO: 74) |

KO:st3Gal4/6/mgat4A/4B/5

| Clone | Inser & Del | Alignment |
|---|---|---|
| mgat4A-WT | ZFN | TTCTGAGTTGAAT<u>GCCATTGTCCAACA</u>gtt------------- tc<u>GCCGTGCAGGAG</u>CAGCAACTAACGGAAG (SEQ ID NO: 9) |
| mgat4A-alle1 | -5 bp | TTCTGAGTTGAATGCCATTGTCCAACAg------------------ CCGTGCAGGAGCAGCAACTAACGGAAG (SEQ ID NO: 10) |
| mgat4A-alle2 | +13 bp | TTCTGAGTTGAATGCCATTGTCCAACAgttGAATTCTAGATGAtcGCCGTGCAGG AGCAGCAACTAACGGAAG (SEQ ID NO: 11) |
| mgat4B-WT | ZFN | <u>GCCCTCCAGCAGCCCTCT</u>gagga<u>CTGGATGATCCTGGAGTT</u> (SEQ ID NO: 12) |
| mgat4B-alle1 | -7 bp | GCCCTCCAGCAGCCCTCTg-------GATGATCCTGGAGTT (SEQ ID NO: 13) |
| mgat5-WT | ZFN | GGGGGATGATG<u>CTTCTGCACTTCACCATCCA</u>g---- cagcg<u>GACTCAGCCTGAGAGCAGCT</u>CCATGTT (SEQ ID NO: 17) |
| mgat5-alle1 | +4 bp | GGGGGATGATGCTTCTGCACTTCACCATCCAgcagcCAGCgGACTCAGCCTGAGA GCAGCTCCATGTT (SEQ ID NO: 62) |
| mgat5-alle2 | -4 bp | GGGGGATGATGCTTCTGCACTTCACCATCCAg-------- gGACTCAGCCTGAGAGCAGCTCCATGTT (SEQ ID NO: 63) |
| mgat5-alle3 | -16 bp | GGGGGATGATGCTTCTGCACTTC------------------- CTCAGCCTGAGAGCAGCTCCATGTT (SEQ ID NO: 64) |
| st3Gal4-WT | ZFN | <u>GGCAGCCTCCAGTGTCGTC</u>gttgt----g<u>TTGTGGTGGGGAATGGGC</u> (SEQ ID NO: 45) |
| st3Gal4-alle1 | -5 bp | GGCAGCCTCCAGTGTCGTCgttgt---------gGTGGGGAATGGGC (SEQ ID NO: 68) |
| st3Gal4-alle2 | +4bp | GGCAGCCTCCAGTGTCGTCgTTGTttgtGTTGTGGTGGGGAATGGGC (SEQ ID NO: 46) |
| st3Gal6-WT | ZFN | <u>CGGTACCTCTGATTTTGCT</u>ttgcc<u>CTATGGGACAAGGCC</u> (SEQ ID NO: 48) |
| st3Gal6-alle1 | -4 bp | CGGTACCTCTGATTTTGCTt----CTATGGGACAAGGCC (SEQ ID NO: 49) |
| st3Gal6-alle2 | -2 bp | CGGTACCTCTGATTTTGCTttg--CTATGGGACAAGGCC (SEQ ID NO: 71) |

KI:ST6GAL1/KO:st3gal4/6

| Clone | Inser & Del | Alignment |
|---|---|---|
| st3Gal4-WT | ZFN | <u>GGCAGCCTCCAGTGTCGTC</u>gttgt----g<u>TTGTGGTGGGGAATGGGC</u> (SEQ ID NO: 45) |
| st3Gal4-alle1 | +4 bp | GGCAGCCTCCAGTGTCGTCgttgtTTGTgTTGTGGTGGGGAATGGGC (SEQ ID NO: 46) |
| st3Gal4-alle2 | -4 bp | GGCAGCCTCCAGTGTCGTCg--------gTTGTGGTGGGGAATGGGC (SEQ ID NO: 47) |
| st3Gal6-WT | ZFN | <u>CGGTACCTCTGATTTTGCT</u>-ttgcc<u>CTATGGGACAAGGCC</u> (SEQ ID NO: 48) |
| st3Gal6-alle1 | +1 bp | CGGTACCTCTGATTTTGCTTttgccCTATGGGACAAGGCC (SEQ ID NO: 70) |
| st3Gal6-alle2 | -7 bp | CGGTACCTCTGATTTTG--------CTATGGGACAAGGCC (SEQ ID NO: 72) |

KI:ST6GAL1/KO:st3gal4/6/mgat4A/4B/5

| Clone | Inser & Del | Alignment |
|---|---|---|
| mgat4A-WT | ZFN | TTCTGAGTTGAAT<u>GCCATTGTCCAACA</u>gtt------------- tc<u>GCCGTGCAGGAG</u>CAGCAACTAACGGAAG (SEQ ID NO: 9) |
| mgat4A-alle1 | -5 bp | TTCTGAGTTGAATGCCATTGTCCAACAg------------------ CCGTGCAGGAGCAGCAACTAACGGAAG (SEQ ID NO: 10) |
| mgat4A-alle2 | +13 bp | TTCTGAGTTGAATGCCATTGTCCAACAgttGAATTCTAGATGAtcGCCGTGCAGG AGCAGCAACTAACGGAAG (SEQ ID NO: 11) |
| mgat4B-WT | ZFN | <u>GCCCTCCAGCAGCCCTCT</u>gagga<u>CTGGATGATCCTGGAGTT</u> (SEQ ID NO: 12) |
| mgat4B-alle1 | -7 bp | GCCCTCCAGCAGCCCTCTg-------GATGATCCTGGAGTT (SEQ ID NO: 13) |
| mgat5-WT | ZFN | GGGGGATGATG<u>CTTCTGCACTTCACCATCCA</u>g---- cagcg<u>GACTCAGCCTGAGAGCAGCT</u>CCATGTT (SEQ ID NO: 17) |
| mgat5-alle1 | +4 bp | GGGGGATGATGCTTCTGCACTTCACCATCCAgcagcCAGCgGACTCAGCCTGAGA GCAGCTCCATGTT (SEQ ID NO: 62) |
| mgat5-alle2 | -4 bp | GGGGGATGATGCTTCTGCACTTCACCATCCAg-------- gGACTCAGCCTGAGAGCAGCTCCATGTT (SEQ ID NO: 63) |

TABLE 4-continued

ZFN design and sequence analysis of CHO glycoengineered clones.

| Clone | Inser & Del | Alignment |
|---|---|---|
| mgat5-alle3 | -16 bp | GGGGGATGATGCTTCTGCACTTC--------------------CTCAGCCTGAGAGCAGCTCCATGTT (SEQ ID NO: 64) |
| st3Gal4-WT | ZFN | <u>GGCAGCCTCCAGTGTCGTC</u>gttgt----g<u>TTGTGGTGGGGAATGGGC</u> (SEQ ID NO: 45) |
| st3Gal4-alle1 | -5 bp | GGCAGCCTCCAGTGTCGTCgttgt---------gGTGGGGAATGGGC (SEQ ID NO: 68) |
| st3Gal4-alle2 | +4 bp | GGCAGCCTCCAGTGTCGTCgTTGTttgtgTTGTGGTGGGGAATGGGC (SEQ ID NO: 46) |
| st3Gal6-WT | ZFN | <u>CGGTACCTCTGATTTTGCT</u>ttgcc<u>CTATGGGACAAGGCC</u> (SEQ ID NO: 48) |
| st3Gal6-alle1 | -4 bp | CGGTACCTCTGATTTTGCTt----CTATGGGACAAGGCC (SEQ ID NO: 49) |
| st3Gal6-alle2 | -2 bp | CGGTACCTCTGATTTTGCTttg--CTATGGGACAAGGCC (SEQ ID NO: 71) |

KO:mgat2

| Clone | Inser & Del | Alignment |
|---|---|---|
| mgat2-WT | TALEN | <u>TCCTTTGTCGCCCATTGCT</u>gctccagaggacgaag<u>CCGCAGGCGGCCACCACGA</u> (SEQ ID NO: 3) |
| mgat2-alle1 | -4 bp | TCCTTTGTCGCCCATTGCTgctcc----gacgaagccgcaggcggccaccacga (SEQ ID NO: 61) |

KO:mgat2/stgal4/6

| Clone | Inser & Del | Alignment |
|---|---|---|
| mgat2-WT | TALEN | <u>TCCTTTGTCGCCCATTGCT</u>gctccagaggacgaag<u>CCGCAGGCGGCCACCACGA</u> (SEQ ID NO: 3) |
| mgat2-alle1 | -4 bp | TCCTTTGTCGCCCATTGCTgctccag----cgaagCCGCAGGCGGCCACCACGA (SEQ ID NO: 78) |
| st3Gal4-WT | ZFN | <u>GGCAGCCTCCAGTGTCGTC</u>gttgt----g<u>TTGTGGTGGGGAATGGGC</u> (SEQ ID NO: 45) |
| st3Gal4-alle1 | +4 bp | GGCAGCCTCCAGTGTCGTCgttgtTTGTgTTGTGGTGGGGAATGGGC (SEQ ID NO: 46) |
| st3Gal4-alle2 | -4 bp | GGCAGCCTCCAGTGTCGTCg--------gTTGTGGTGGGGAATGGGC (SEQ ID NO: 47) |
| st3Gal6-WT | ZFN | <u>CGGTACCTCTGATTTTGCT</u>-ttgcc<u>CTATGGGACAAGGCC</u> (SEQ ID NO: 48) |
| st3Gal6-alle1 | +1 bp | CGGTACCTCTGATTTTGCTTttgccCTATGGGACAAGGCC (SEQ ID NO: 70) |
| st3Gal6-alle2 | -7 bp | CGGTACCTCTGATTTTG--------CTATGGGACAAGGCC (SEQ ID NO: 72) |

KO:mgat2/mgat4A/4B/5

| Clone | Inser & Del | Alignment |
|---|---|---|
| mgat2-WT | TALEN | <u>TCCTTTGTCGCCCATTGCT</u>gctccagaggacgaag<u>CCGCAGGCGGCCACCACGA</u> (SEQ ID NO: 3) |
| mgat2-alle1 | -4 bp | TCCTTTGTCGCCCATTGCTgctccag----cgaagCCGCAGGCGGCCACCACGA (SEQ ID NO: 78) |
| mgat4A-WT | ZFN | <u>TTCTGAGTTGAATGCCATTGTCCAACA</u>gtt-------------tc<u>GCCGTGCAGGAG</u>CAGCAACTAACGGAAG (SEQ ID NO: 9) |
| mgat4A-alle1 | -5 bp | TTCTGAGTTGAATGCCATTGTCCAACAg------------------CCGTGCAGGAGCAGCAACTAACGGAAG (SEQ ID NO: 10) |
| mgat4A-alle2 | +13 bp | TTCTGAGTTGAATGCCATTGTCCAACAgttGAATTCTAGATGAtcGCCGTGCAGGAGCAGCAACTAACGGAAG (SEQ ID NO: 11) |
| mgat4B-WT | ZFN | <u>GCCCTCCAGCAGCCCTCT</u>gagga<u>CTGGATGATCCTGGAGTT</u> (SEQ ID NO: 12) |
| mgat4B-alle1 | -7 bp | GCCCTCCAGCAGCCCTCTg-------GATGATCCTGGAGTT (SEQ ID NO: 13) |
| mgat5-WT | ZFN | GGGGGATGATGC<u>TTCTGCACTTCACCATCCA</u>g----cagcg<u>GACTCAGCCTGAGAGCAGCT</u>CCATGTT (SEQ ID NO: 17) |
| mgat5-alle1 | +4 bp | GGGGGATGATGCTTCTGCACTTCACCATCCAgcagcCAGCgGACTCAGCCTGAGAGCAGCTCCATGTT (SEQ ID NO: 62) |
| mgat5-alle2 | -4 bp | GGGGGATGATGCTTCTGCACTTCACCATCCAg--------gGACTCAGCCTGAGAGCAGCTCCATGTT (SEQ ID NO: 63) |
| mgat5-alle3 | -16 bp | GGGGGATGATGCTTCTGCACTTC--------------------CTCAGCCTGAGAGCAGCTCCATGTT (SEQ ID NO: 64) |

KO:mgat2/st3gal4/6/mgat4A/4B/5

| Clone | Inser & Del | Alignment |
|---|---|---|
| mgat2-WT | TALEN | <u>TCCTTTGTCGCCCATTGCT</u>gctccagaggacgaag<u>CCGCAGGCGGCCACCACGA</u> (SEQ ID NO: 3) |
| mgat2-alle1 | -5 bp | TCCTTTGTCGCCCATTGCTgctcca-----cgaaGCCGCAGGCGGCCACCACGA (SEQ ID NO: 4) |
| mgat4A-WT | ZFN | <u>TTCTGAGTTGAATGCCATTGTCCAACA</u>gtt-------------tc<u>GCCGTGCAGGAG</u>CAGCAACTAACGGAAG (SEQ ID NO: 9) |

TABLE 4-continued

ZFN design and sequence analysis of CHO glycoengineered clones.

| Clone | Inser & Del | Alignment |
|---|---|---|
| mgat4A-alle1 | -5 bp | TTCTGAGTTGAATGCCATTGTCCAACAg-----------------CCGTGCAGGAGCAGCAACTAACGGAAG (SEQ ID NO: 10) |
| mgat4A-alle2 | +13 bp | TTCTGAGTTGAATGCCATTGTCCAACAgttGAATTCTAGATGAtcGCCGTGCAGGAGCAGCAACTAACGGAAG (SEQ ID NO: 11) |
| mgat4B-WT | ZFN | GCCCTCCAGCAGCCCTCTgaggaCTGGATGATCCTGGAGTT (SEQ ID NO: 12) |
| mgat4B-alle1 | -7 bp | GCCCTCCAGCAGCCCTCTg-------GATGATCCTGGAGTT (SEQ ID NO: 13) |
| mgat5-WT | ZFN | GGGGGATGATGCTTCTGCACTTCACCATCCAg----cagcgGACTCAGCCTGAGAGCAGCTCCATGTT (SEQ ID NO: 17) |
| mgat5-alle1 | +4 bp | GGGGGATGATGCTTCTGCACTTCACCATCCAgcagcCAGCgGACTCAGCCTGAGAGCAGCTCCATGTT (SEQ ID NO: 62) |
| mgat5-alle2 | -4 bp | GGGGGATGATGCTTCTGCACTTCACCATCCAg--------gGACTCAGCCTGAGAGCAGCTCCATGTT (SEQ ID NO: 63) |
| mgat5-alle3 | -16 bp | GGGGGATGATGCTTCTGCACTTC-------------------CTCAGCCTGAGAGCAGCTCCATGTT (SEQ ID NO: 64) |
| st3Gal4-WT | ZFN | GGCAGCCTCCAGTGTCGTCgttgt----gTTGTGGTGGGGAATGGGC (SEQ ID NO: 45) |
| st3Gal4-alle1 | -5 bp | GGCAGCCTCCAGTGTCGTCgttgt---------gGTGGGGAATGGGC (SEQ ID NO: 68) |
| st3Gal4-alle2 | +4 bp | GGCAGCCTCCAGTGTCGTCgTTGtttgtGTTGTGGTGGGGAATGGGC (SEQ ID NO: 46) |
| st3Gal6-WT | ZFN | CGGTACCTCTGATTTTGCTttgccCTATGGGACAAGGCC (SEQ ID NO: 48) |
| st3Gal6-alle1 | -4 bp | CGGTACCTCTGATTTTGCTt----CTATGGGACAAGGCC (SEQ ID NO: 49) |
| st3Gal6-alle2 | -2 bp | CGGTACCTCTGATTTTGCTttg--CTATGGGACAAGGCC (SEQ ID NO: 71) |
| KO:fut8 | | |
| fut8-WT | CRISPR | CAAATACTTGATCCGTCCACAACCT-TGGCTGGAAAGGGAA (SEQ ID NO: 51) |
| fut8-alle1 | -1 bp | CAAATACTTGATCCGTCCACAACC--TGGCTGGAAAGGGAA (SEQ ID NO: 52) |
| fut8-alle2 | +1 bp | CAAATACTTGATCCGTCCACAACCTTTGGCTGGAAAGGGAA (SEQ ID NO: 53) |
| KO:fut8/B4galt1 | | |
| fut8-WT | CRISPR | CAAATACTTGATCCGTCCACAACCT-TGGCTGGAAAGGGAA (SEQ ID NO: 51) |
| fut8-alle1 | -4 bp | CAAATACTTGATCCGTCCACAA-----GGCTGGAAAGGGAA (SEQ ID NO: 77) |
| fut8-alle2 | +1 bp | CAAATACTTGATCCGTCCACAACCTTTGGCTGGAAAGGGAA (SEQ ID NO: 53) |
| B4galt1-WT | ZFN | TGCATCCGGTCCTACAGCgccagc----AACTGGACTATGGTA (SEQ ID NO: 31) |
| B4galt1-alle1 | +4 bp | TGCATCCGGTCCTACAGCgccagcCAGCAACTGGACTATGGTA (SEQ ID NO: 32) |
| KO:mgat3 | | |
| mgat3-WT | ZFN | TTCCTGGACCACTTCCCAcccggt----------GGCCGGCAGGATGGC (SEQ ID NO: 5) |
| mgat3-alle1 | -21 bp | TTCCTGGACCACT-------------------------ATGGC (SEQ ID NO: 6) |
| mgat3-alle2 | +293 bp | TTCCTGGACCACTGATACcc (SEQ ID NO: 7)--+293 bp--cggtGGCCGGCAGGATGGC (SEQ ID NO: 8) |
| KO:mgat4C | | |
| mgat4C-WT | ZFN | ATACTTCAGACTATtatgtAATGCTCGAAGATGATGTT (SEQ ID NO: 14) |
| mgat4C-alle1 | -13 bp | ATACTTCAGACT-------------CGAAGATGATGTT (SEQ ID NO: 15) |
| mgat4C-alle2 | -8 bp | ATACTTCAGACTAT--------GCTCGAAGATGATGTT (SEQ ID NO: 16) |

TABLE 4-continued

ZFN design and sequence analysis of CHO glycoengineered clones.

| Clone | Inser & Del | Alignment |
|---|---|---|
| KO:mgat5B | | |
| mgat5B-WT | ZFN | <u>CGTGGCGCCCTCCGCAAG</u>atgagt<u>GACCTGCTGGAGCTG</u> (SEQ ID NO: 22) |
| mgat5B-alle1 | -7 bp | CAGCTCCAGCAGGT-------CTTGCGGAGGGCGCCACG (SEQ ID NO: 23) |
| mgat5B-alle2 | -5 bp | CAGCTCCAGCAGGT-----ATCTTGCGGAGGGCGCCACG (SEQ ID NO: 24) |
| KO:B3gnt8 | | |
| B3gnt8-WT | TALEN | <u>TGGTCCAGAGATAGCTAAT</u>gaagcttctagggtg<u>GAGAAGCTGGGGCTGCTGA</u> (SEQ ID NO: 75) |
| B3gnt8-alle1 | -17 bp | TGGTCCAGAGG-----------------AGGGTGGAGAAGCTGGGGCTGCTGA (SEQ ID NO: 76) |
| KO:mgat1 | | |
| mgat1-WT | ZFN | <u>AACAAGTTCAAGTTC</u>ccagca<u>GCTGTGGTAGTGGAGGAC</u> (SEQ ID NO: 1) |
| mgat1-alle1 | -2 bp | <u>AACAAGTTCAAGTTC</u>c--gca<u>GCTGTGGTAGTGGAGGAC</u> (SEQ ID NO: 2) |

Gene targeting region underlined.

TABLE 5

(SEQ ID NO: 60)
tcgcgcgtttcggtgatgacggtgaaaacctctgacacatgcagctccc
ggagacggtcacagcttgtctgtaagcggatgccgggagcagacaagcc
cgtcagggcgcgtcagcgggtgttggcgggtgtcggggctggcttaact
atgcggcatcagagcagattgtactgagagtgcaccatatgcgcgtgtga
aataccgcacagatgcgtaaggagaaaataccgcatcaggcgccattcg
ccattcaggctgcgcaactgttgggaagggcgatcggtgcgggcctctt
cgctattacgccagctggcgaaaggggatgtgctgcaaggcgattaag
ttgggtaacgccagggttttcccagtcacgacgttgtaaaacgacggcc
agtgaattcgagctcggtaccaagcttggttgcatgctgtccggagtct
cagcgttataccagaagtgacctgggtcggggaagactatagtgtcacc
taaatctctagagccctttcattaggcgcgccaatcccattgcaaattct
acaaaaggagtgtttcccaactgctctatcaagaggaatgttgcacact
gtgacctgaatgcaaacatcacacgcgccagcagagaggaagaagagag
gcttccctgaccgggaatcgaacccgggccgcggcggtgagagcgccga
atcctaaccactagaccaccagggagcacgcgccagcagattcaatgagct
ataattatccccttggaaaacctacaaaaacagtgtttcaaaactgctc
tgtgaaaagggacctttgctagcacgcggcgccaggcaaaacgtgggca
cgctgcgttggccgggaatcgaacccgggtcaactgcttggaaggcagc
tatgctcaccactataccaccaacgcgcacacgcgccagcagattctac
gggaagagtgtttcaaaactgctctatcaagagaaatgttccaccttgt
gtgtggaatgcagccatcacacgcgtccatgaaagggcttaattaagat
atcgtttaaacgtcgacctgcagaggccggcggataactagctgatcgc
ggaatcctgtccctaggccaccactgtgggtgcccttcattaggcgc
gccaatcccattgcaaattctacaaaaaggagtgtttcccaactgctcta
tcaagaggaatgttgcacactgtgacctgaatgcaaacatcacacgcgc
cagcagagaggaagaagagaggcttccctgaccgggaatcgaacccggg
ccgcggcggtgagagcgccgaatcctaaccactagaccaccagggagca
cgcgccaaagctcaatgagctataattatcccctttggaaaactacaaa
aacagtgtttcaaaactgctctgtgaaaagggacctttgctagcacgcg
gcgccaggcaaaacgtgggcacgctgcgttggccgggaatcgaaccggg
gtcaactgcttggaaggcagctatgctcaccactataccaccaacgcgc
acacgcgccagcagattctacgggaagagtgtttcaaaactgctctatc
aagagaaatgttccaccttgtgtgtggaatgcagccatcacacgcgtcc
atgaaagggcggttgcatgctgtccggagtctcagcgttataccagaag
tgacctgggtcggggaagaaagcttcatggtcatagctgtttcctgtg
tgaaattgttatccgctcacaattccacacaacatacgagccggaagca
taaagtgtaaagcctggggtgcctaatgagtgagctaactcacattaat
tgcgttgcgctcactgcccgctttccagtcgggaaacctgtcgtgccag
ctgcattaatgaatcggccaacgcgcggggagaggcggtttgcgtattg
ggcgctcttccgcttcctcgctcactgactcgctgcgctcggtcgttcg
gctgcggcgagcggtatcagctcactcaaaggcggtaatacggttatcc
acagaatcaggggataacgcaggaaagaacatgtgagcaaaaggccagc aaaaggccaggaaccgtaaaaaggccgcgttgctggcgttttttccatag
gctccgcccccctgacgagcatcacaaaaatcgacgctcaagtcagagg
tggcgaaacccgacaggactataaagataccaggcgtttccccctggaa
gctccctcgtgcgctctcctgttccgaccctgccgcttaccggatacct
gtccgcctttctcccttcgggaagcgtggcgctttctcatagctcacgc
tgtaggtatctcagttcggtgtaggtcgttcgctccaagctgggctgtg
tgcacgaaccccccgttcagcccgaccgctgcgccttatccggtaacta
tcgtcttgagtccaacccggtaagacacgacttatcgccactggcagca
gccactggtaacaggattagcagagcgaggtatgtaggcggtgctacag
agttcttgaagtggtggcctaactacggctacactagaagaacagtatt
tggtatctgcgctctgctgaagcagttaccttcggaaaaagagttggt
agctcttgatccggcaaacaaaccaccgctggtagcggtggtttttttg
tttgcaagcagcagattacgcgcagaaaaaaaggatctcaagaagatcc
tttgatcttttctacggggtctgacgctcagtggaacgaaaactcacgt
taagggattttggtcatgagattatcaaaaaggatcttcacctagatcc
ttttaaattaaaaatgaagttttaaatcaatctaaagtatatatgagta
aacttggtctgacagttagaaaaactcatcgagcatcaaatgaaactgc
aatttattcatatcaggattatcaataccatattttgaaaaagccgtt
tctgtaatgaaggagaaaactcaccgaggcagttccataggatggcaag
atcctggtatcggtctgcgattccgactcgtccaacatcaatacaacct
attaatttcccctcgtcaaaaataaggttatcaagtgagaaatcaccat
gagtgacgactgaatccggtgagaatggcaaaagtttatgcatttcttt
ccagacttgttcaacaggccagccattacgctcgtcatcaaaatcactc
gcatcaaccaaaccgttattcattcgtgattgcgcctgagcgagacgaa
atacgcgatcgctgttaaaaggacaattacaaacaggaatcgaatgcaa
ccggcgcaggaacactgccagcgcatcaacaatattttcacctgaatca
ggatattcttctaatacctggaatgctgttttcccagggatcgcagtgg
tgagtaaccatgcatcatcaggagtacggataaaatgcttgatggtcgg
aagagcataaattccgtcagccagtttagtctgaccatctcatctgta
acatcattggcaacgctacctttgccatgtttcagaaacaactctggcg
catcgggcttcccatacaatcgatagattgtcgcacctgattgcccgac
attatcgcgagcccatttatacccatataaatcagcatccatgttggaa
tttaatcgcggcctagagcaagacgtttcccgttgaatatggctcatac
tcttcctttttcaatattattgaagcatttatcagggttattgtctcat
gagcggatacatatttgaatgtatttagaaaaataaacaaataggggtt
ccgcgcacatttccccgaaaagtgccacctgacgtctaagaaaccatta
ttatcatgacattaacctataaaaataggcgtatcacgaggccctttcg
tc

The invention claimed is:

1. A mammalian cell comprising one or more glycosyltransferase genes that have been partially or fully inactivated, and that has more homogeneous glycosylation capacities, wherein Alpha-1,6-Mannosyl-Glycoprotein 2-Beta-N-Acetylglucosaminyltransferase (mgat2) has been knocked out (KO), and, optionally wherein Alpha-1,3-Mannosyl-Glycoprotein 4-Beta-N-Acetylglucosaminyltransferase (mgat4A) and/or Alpha-1,3-Mannosyl-Glycoprotein 4-Beta-N-Acetylglucosaminyltransferase B (mgat4B) and/or Alpha-1,6-Mannosylglycoprotein 6-Beta-N-Acetylglucosaminyltransferase (mgat5) has been KO, allowing production of N-glycans with monoantennary structure, and further comprising KO of at least one sialyltransferase and KO of a UDP-GlcNAc:betaGal beta-1,3-N-acetylglucosaminyltransferase 2 (B3 gnt2) gene, allowing production of N-glycans with monoantennary structure and without sialic acid capping and without Poly-N-acetyllactosamine (poly-LacNAc).

2. The mammalian cell according to claim 1, wherein the cell is derived from Chinese hamster ovary (CHO) or from human kidney.

3. The mammalian cell according to claim 1, wherein the cell is selected from the group consisting of Chinese hamster ovary cell (CHO), mouse myeloma cell (NS0), mouse myeloma cell (SP2/0), rat myeloma cell (YB2/0), Chinese hamster ovary cell (CHO-K1), Chinese hamster ovary cell (CHO-DXB11), Chinese hamster ovary cell (CHO-DG44), Chinese hamster ovary cell (CHO-S), human embryonic kidney cell (HEK293), human umbilical vein endothelial cell (HUVEC), hybrid cell of human kidney and B-cell (HKB), and human fetal retinoblast cell (PER-C6) or derivatives of any of these cells.

4. The mammalian cell according to claim 1, wherein the cell is a CHO cell.

5. The mammalian cell according to claim 1, further encoding an exogenous nucleic acid encoding an exogeneous protein.

* * * * *

SEQUENCE LISTING

<160> NUMBER OF SEQ ID NOS: 78

<210> SEQ ID NO 1
<211> LENGTH: 39
<212> TYPE: DNA
<213> ORGANISM: Artificial Sequence
<220> FEATURE:
<223> OTHER INFORMATION: mgat1-WT

<400> SEQUENCE: 1
aacaagttca agttcccagc agctgtggta gtggaggac        39

<210> SEQ ID NO 2
<211> LENGTH: 37
<212> TYPE: DNA
<213> ORGANISM: Artificial Sequence
<220> FEATURE:
<223> OTHER INFORMATION: mgat1-alle1

<400> SEQUENCE: 2
aacaagttca agttccgcag ctgtggtagt ggaggac        37

<210> SEQ ID NO 3
<211> LENGTH: 54
<212> TYPE: DNA
<213> ORGANISM: Artificial Sequence
<220> FEATURE:
<223> OTHER INFORMATION: mgat2-WT

<400> SEQUENCE: 3
tcctttgtcg cccattgctg ctccagagga cgaagccgca ggcggccacc acga        54

<210> SEQ ID NO 4
<211> LENGTH: 49
<212> TYPE: DNA
<213> ORGANISM: Artificial Sequence
<220> FEATURE:
<223> OTHER INFORMATION: mgat2-alle1

<400> SEQUENCE: 4
tcctttgtcg cccattgctg ctccacgaag ccgcaggcgg ccaccacga        49

<210> SEQ ID NO 5
<211> LENGTH: 39
<212> TYPE: DNA
<213> ORGANISM: Artificial Sequence
<220> FEATURE:
<223> OTHER INFORMATION: mgat3-WT

<400> SEQUENCE: 5
ttcctggacc acttcccacc cggtggccgg caggatggc        39

<210> SEQ ID NO 6
<211> LENGTH: 18
<212> TYPE: DNA
<213> ORGANISM: Artificial Sequence
<220> FEATURE:
<223> OTHER INFORMATION: mgat3-alle1

<400> SEQUENCE: 6
ttcctggacc actatggc        18

<210> SEQ ID NO 7
<211> LENGTH: 20
<212> TYPE: DNA
<213> ORGANISM: Artificial Sequence

```
<220> FEATURE:
<223> OTHER INFORMATION: mgat3-alle2 (N-terminus)

<400> SEQUENCE: 7
ttcctggacc actgataccc                                                    20

<210> SEQ ID NO 8
<211> LENGTH: 19
<212> TYPE: DNA
<213> ORGANISM: Artificial Sequence
<220> FEATURE:
<223> OTHER INFORMATION: mgat3-alle2 (C-terminus)

<400> SEQUENCE: 8
cggtggccgg caggatggc                                                     19

<210> SEQ ID NO 9
<211> LENGTH: 60
<212> TYPE: DNA
<213> ORGANISM: Artificial Sequence
<220> FEATURE:
<223> OTHER INFORMATION: mgat4A-WT

<400> SEQUENCE: 9
ttctgagttg aatgccattg tccaacagtt tcgccgtgca ggagcagcaa ctaacggaag        60

<210> SEQ ID NO 10
<211> LENGTH: 55
<212> TYPE: DNA
<213> ORGANISM: Artificial Sequence
<220> FEATURE:
<223> OTHER INFORMATION: mgat4A-alle1

<400> SEQUENCE: 10
ttctgagttg aatgccattg tccaacagcc gtgcaggagc agcaactaac ggaag             55

<210> SEQ ID NO 11
<211> LENGTH: 73
<212> TYPE: DNA
<213> ORGANISM: Artificial Sequence
<220> FEATURE:
<223> OTHER INFORMATION: mgat4A-alle2

<400> SEQUENCE: 11
ttctgagttg aatgccattg tccaacagtt gaattctaga tgatcgccgt gcaggagcag        60
caactaacgg aag                                                           73

<210> SEQ ID NO 12
<211> LENGTH: 41
<212> TYPE: DNA
<213> ORGANISM: Artificial Sequence
<220> FEATURE:
<223> OTHER INFORMATION: mgat4B-WT

<400> SEQUENCE: 12
gccctccagc agccctctga ggactggatg atcctggagt t                            41

<210> SEQ ID NO 13
<211> LENGTH: 34
<212> TYPE: DNA
<213> ORGANISM: Artificial Sequence
<220> FEATURE:
<223> OTHER INFORMATION: mgat4B-alle1

<400> SEQUENCE: 13
```

-continued gccctccagc agccctctgg atgatcctgg agtt                                        34

<210> SEQ ID NO 14
<211> LENGTH: 38
<212> TYPE: DNA
<213> ORGANISM: Artificial Sequence
<220> FEATURE:
<223> OTHER INFORMATION: mgat4C-WT

<400> SEQUENCE: 14
atacttcaga ctattatgta atgctcgaag atgatgtt                                    38

<210> SEQ ID NO 15
<211> LENGTH: 25
<212> TYPE: DNA
<213> ORGANISM: Artificial Sequence
<220> FEATURE:
<223> OTHER INFORMATION: mgat4C-alle1

<400> SEQUENCE: 15
atacttcaga ctcgaagatg atgtt                                                  25

<210> SEQ ID NO 16
<211> LENGTH: 30
<212> TYPE: DNA
<213> ORGANISM: Artificial Sequence
<220> FEATURE:
<223> OTHER INFORMATION: mgat4C-alle2

<400> SEQUENCE: 16
atacttcaga ctatgctcga agatgatgtt                                             30

<210> SEQ ID NO 17
<211> LENGTH: 64
<212> TYPE: DNA
<213> ORGANISM: Artificial Sequence
<220> FEATURE:
<223> OTHER INFORMATION: mgat5-WT

<400> SEQUENCE: 17
gggggatgat gcttctgcac ttcaccatcc agcagcggac tcagcctgag agcagctcca           60
tgtt                                                                         64

<210> SEQ ID NO 18
<211> LENGTH: 78
<212> TYPE: DNA
<213> ORGANISM: Artificial Sequence
<220> FEATURE:
<223> OTHER INFORMATION: mgat5-alle1

<400> SEQUENCE: 18
gggggatgat gcttctgcac ttcaccatcc agcatgaatt ctagatgagc ggactcagcc           60
tgagagcagc tccatgtt                                                          78

<210> SEQ ID NO 19
<211> LENGTH: 63
<212> TYPE: DNA
<213> ORGANISM: Artificial Sequence
<220> FEATURE:
<223> OTHER INFORMATION: mgat5-alle2

<400> SEQUENCE: 19
gggggatgat gcttctgcac ttcaccatcc agagcggact cagcctgaga gcagctccat           60
gtt                                                                          63

<210> SEQ ID NO 20
<211> LENGTH: 35
<212> TYPE: DNA
<213> ORGANISM: Artificial Sequence
<220> FEATURE:
<223> OTHER INFORMATION: mgat5-alle3 (N-terminus)

<400> SEQUENCE: 20
gggggatgat gcttctgcac ttcaccatcc agcag                        35

<210> SEQ ID NO 21
<211> LENGTH: 29
<212> TYPE: DNA
<213> ORGANISM: Artificial Sequence
<220> FEATURE:
<223> OTHER INFORMATION: mgat5-alle3 (C-terminus)

<400> SEQUENCE: 21
cggactcagc ctgagagcag ctccatgtt                              29

<210> SEQ ID NO 22
<211> LENGTH: 39
<212> TYPE: DNA
<213> ORGANISM: Artificial Sequence
<220> FEATURE:
<223> OTHER INFORMATION: mgat5B-WT

<400> SEQUENCE: 22
cgtggcgccc tccgcaagat gagtgacctg ctggagctg                    39

<210> SEQ ID NO 23
<211> LENGTH: 32
<212> TYPE: DNA
<213> ORGANISM: Artificial Sequence
<220> FEATURE:
<223> OTHER INFORMATION: mgat5B-alle1

<400> SEQUENCE: 23
cagctccagc aggtcttgcg gagggcgcca cg                           32

<210> SEQ ID NO 24
<211> LENGTH: 34
<212> TYPE: DNA
<213> ORGANISM: Artificial Sequence
<220> FEATURE:
<223> OTHER INFORMATION: mgat5B-alle2

<400> SEQUENCE: 24
cagctccagc aggtatcttg cggagggcgc cacg                         34

<210> SEQ ID NO 25
<211> LENGTH: 39
<212> TYPE: DNA
<213> ORGANISM: Artificial Sequence
<220> FEATURE:
<223> OTHER INFORMATION: B3gnt1-WT

<400> SEQUENCE: 25
tgcagctgct ctacctgtcg ctgctctccg gactgcacg                    39

<210> SEQ ID NO 26
<211> LENGTH: 50
<212> TYPE: DNA
<213> ORGANISM: Artificial Sequence
<220> FEATURE:

-continued

<223> OTHER INFORMATION: B3gnt1-alle1

<400> SEQUENCE: 26
tgcagctgct ctacctgtcg cagctgctct acctgtctcc ggactgcacg        50

<210> SEQ ID NO 27
<211> LENGTH: 34
<212> TYPE: DNA
<213> ORGANISM: Artificial Sequence
<220> FEATURE:
<223> OTHER INFORMATION: B3gnt1-alle2

<400> SEQUENCE: 27
tgcagctgct ctacctgtct ctccggactg cacg                         34

<210> SEQ ID NO 28
<211> LENGTH: 35
<212> TYPE: DNA
<213> ORGANISM: Artificial Sequence
<220> FEATURE:
<223> OTHER INFORMATION: B3gnt2-WT

<400> SEQUENCE: 28 ttcagcccttt cccgggcgta ctggaacaga gagca                       35

<210> SEQ ID NO 29
<211> LENGTH: 34
<212> TYPE: DNA
<213> ORGANISM: Artificial Sequence
<220> FEATURE:
<223> OTHER INFORMATION: B3gnt2-alle1

<400> SEQUENCE: 29
ttcagccctt ccgggcgtac tggaacagag agca                         34

<210> SEQ ID NO 30
<211> LENGTH: 31
<212> TYPE: DNA
<213> ORGANISM: Artificial Sequence
<220> FEATURE:
<223> OTHER INFORMATION: B3gnt2-alle2

<400> SEQUENCE: 30
ttcagccctt cccgtactgg aacagagagc a                            31

<210> SEQ ID NO 31
<211> LENGTH: 39
<212> TYPE: DNA
<213> ORGANISM: Artificial Sequence
<220> FEATURE:
<223> OTHER INFORMATION: B4galt1-WT

<400> SEQUENCE: 31
tgcatccggt cctacagcgc cagcaactgg actatggta                    39

<210> SEQ ID NO 32
<211> LENGTH: 43
<212> TYPE: DNA
<213> ORGANISM: Artificial Sequence
<220> FEATURE:
<223> OTHER INFORMATION: B4galt1-alle1

<400> SEQUENCE: 32
tgcatccggt cctacagcgc cagccagcaa ctggactatg gta               43

```
<210> SEQ ID NO 33
<211> LENGTH: 40
<212> TYPE: DNA
<213> ORGANISM: Artificial Sequence
<220> FEATURE:
<223> OTHER INFORMATION: B4galt2-WT

<400> SEQUENCE: 33
cagccccgcc actttgccat cgccatggac aagtttggct                 40

<210> SEQ ID NO 34
<211> LENGTH: 18
<212> TYPE: DNA
<213> ORGANISM: Artificial Sequence
<220> FEATURE:
<223> OTHER INFORMATION: B4galt2-alle1 (N-terminus)

<400> SEQUENCE: 34
cagccccgcc actttgcc                                         18

<210> SEQ ID NO 35
<211> LENGTH: 22
<212> TYPE: DNA
<213> ORGANISM: Artificial Sequence
<220> FEATURE:
<223> OTHER INFORMATION: B4galt2-alle1 (C-terminus)

<400> SEQUENCE: 35
atcgccatgg acaagtttgg ct                                    22

<210> SEQ ID NO 36
<211> LENGTH: 41
<212> TYPE: DNA
<213> ORGANISM: Artificial Sequence
<220> FEATURE:
<223> OTHER INFORMATION: B4galt3-WT

<400> SEQUENCE: 36
ctagccctca agtcaggatg ttgcggaggc tgctggagag g               41

<210> SEQ ID NO 37
<211> LENGTH: 46
<212> TYPE: DNA
<213> ORGANISM: Artificial Sequence
<220> FEATURE:
<223> OTHER INFORMATION: B4galt3-alle1

<400> SEQUENCE: 37
ctagccctca agtcaggatg tcgtgttgcg gaggctgctg gagagg          46

<210> SEQ ID NO 38
<211> LENGTH: 43
<212> TYPE: DNA
<213> ORGANISM: Artificial Sequence
<220> FEATURE:
<223> OTHER INFORMATION: B4galt3-alle2

<400> SEQUENCE: 38
ctagccctca agtcaggatg ttgcccggag gctgctggag agg             43

<210> SEQ ID NO 39
<211> LENGTH: 39
<212> TYPE: DNA
<213> ORGANISM: Artificial Sequence
<220> FEATURE:
<223> OTHER INFORMATION: B4galt4-WT
```

<400> SEQUENCE: 39
aactgggact gctttatatt ccacgatgtg gacctggtg                    39

<210> SEQ ID NO 40
<211> LENGTH: 40
<212> TYPE: DNA
<213> ORGANISM: Artificial Sequence
<220> FEATURE:
<223> OTHER INFORMATION: B4galt4-alle1

<400> SEQUENCE: 40
aactgggact gctttattat tccacgatgt ggacctggtg                   40

<210> SEQ ID NO 41
<211> LENGTH: 43
<212> TYPE: DNA
<213> ORGANISM: Artificial Sequence
<220> FEATURE:
<223> OTHER INFORMATION: B4galt4-alle2

<400> SEQUENCE: 41
aactgggact gctttatatt tattccacga tgtggacctg gtg               43

<210> SEQ ID NO 42
<211> LENGTH: 43
<212> TYPE: DNA
<213> ORGANISM: Artificial Sequence
<220> FEATURE:
<223> OTHER INFORMATION: st3Gal3-WT

<400> SEQUENCE: 42
ctctctcttt gtccttgctg gcttcaaatg gcaggacttc aag               43

<210> SEQ ID NO 43
<211> LENGTH: 38
<212> TYPE: DNA
<213> ORGANISM: Artificial Sequence
<220> FEATURE:
<223> OTHER INFORMATION: st3Gal3-alle1

<400> SEQUENCE: 43
ctctctcttt gtccttgctc aaatggcagg acttcaag                     38

<210> SEQ ID NO 44
<211> LENGTH: 42
<212> TYPE: DNA
<213> ORGANISM: Artificial Sequence
<220> FEATURE:
<223> OTHER INFORMATION: st3Gal3-alle2

<400> SEQUENCE: 44
ctctctcttt gtccttgctg gctcaaatgg caggacttca ag                42

<210> SEQ ID NO 45
<211> LENGTH: 43
<212> TYPE: DNA
<213> ORGANISM: Artificial Sequence
<220> FEATURE:
<223> OTHER INFORMATION: st3Gal4-WT

<400> SEQUENCE: 45
ggcagcctcc agtgtcgtcg ttgtgttgtg gtggggaatg ggc               43

<210> SEQ ID NO 46
<211> LENGTH: 47

<212> TYPE: DNA
<213> ORGANISM: Artificial Sequence
<220> FEATURE:
<223> OTHER INFORMATION: st3Gal4-alle1

<400> SEQUENCE: 46
ggcagcctcc agtgtcgtcg ttgtttgtgt tgtggtgggg aatgggc      47

<210> SEQ ID NO 47
<211> LENGTH: 39
<212> TYPE: DNA
<213> ORGANISM: Artificial Sequence
<220> FEATURE:
<223> OTHER INFORMATION: st3Gal4-alle2

<400> SEQUENCE: 47
ggcagcctcc agtgtcgtcg gttgtggtgg ggaatgggc      39

<210> SEQ ID NO 48
<211> LENGTH: 39
<212> TYPE: DNA
<213> ORGANISM: Artificial Sequence
<220> FEATURE:
<223> OTHER INFORMATION: st3Gal6-WT

<400> SEQUENCE: 48
cggtacctct gattttgctt tgccctatgg gacaaggcc      39

<210> SEQ ID NO 49
<211> LENGTH: 35
<212> TYPE: DNA
<213> ORGANISM: Artificial Sequence
<220> FEATURE:
<223> OTHER INFORMATION: st3Gal6-alle1

<400> SEQUENCE: 49
cggtacctct gattttgctt ctatgggaca aggcc      35

<210> SEQ ID NO 50
<211> LENGTH: 17
<212> TYPE: DNA
<213> ORGANISM: Artificial Sequence
<220> FEATURE:
<223> OTHER INFORMATION: st3Gal6-alle2

<400> SEQUENCE: 50
cggtacctct gaaggcc      17

<210> SEQ ID NO 51
<211> LENGTH: 40
<212> TYPE: DNA
<213> ORGANISM: Artificial Sequence
<220> FEATURE:
<223> OTHER INFORMATION: fut8-WT

<400> SEQUENCE: 51
caaatacttg atccgtccac aaccttggct ggaaagggaa      40

<210> SEQ ID NO 52
<211> LENGTH: 39
<212> TYPE: DNA
<213> ORGANISM: Artificial Sequence
<220> FEATURE:
<223> OTHER INFORMATION: fut8-alle1

<400> SEQUENCE: 52
caaatacttg atccgtccac aacctggctg gaaagggaa        39

<210> SEQ ID NO 53
<211> LENGTH: 41
<212> TYPE: DNA
<213> ORGANISM: Artificial Sequence
<220> FEATURE:
<223> OTHER INFORMATION: fut8-alle2

<400> SEQUENCE: 53
caaatacttg atccgtccac aacctttggc tggaaaggga a        41

<210> SEQ ID NO 54
<211> LENGTH: 120
<212> TYPE: DNA
<213> ORGANISM: Artificial Sequence
<220> FEATURE:
<223> OTHER INFORMATION: ssODN with 60bp homology arm sequences

<400> SEQUENCE: 54
gagagagatt ggtcttgctt gtcatcacca acgtatgaac cagtgtgatg gtgaaatgag        60
tcgccgtgca ggagcagcaa ctaacggaag taacactgca ttgactacat tttcaggtac        120

<210> SEQ ID NO 55
<211> LENGTH: 21
<212> TYPE: DNA
<213> ORGANISM: Artificial Sequence
<220> FEATURE:
<223> OTHER INFORMATION: Mgataex1F

<400> SEQUENCE: 55
tatccactgt gttgcttgct g        21

<210> SEQ ID NO 56
<211> LENGTH: 21
<212> TYPE: DNA
<213> ORGANISM: Artificial Sequence
<220> FEATURE:
<223> OTHER INFORMATION: Mgataex2R

<400> SEQUENCE: 56
actgctcttc cagaggtcct g        21

<210> SEQ ID NO 57
<211> LENGTH: 27
<212> TYPE: DNA
<213> ORGANISM: Artificial Sequence
<220> FEATURE:
<223> OTHER INFORMATION: Mgataex2F

<400> SEQUENCE: 57
gaacgccttc gaatagctga acatagg        27

<210> SEQ ID NO 58
<211> LENGTH: 23
<212> TYPE: DNA
<213> ORGANISM: Artificial Sequence
<220> FEATURE:
<223> OTHER INFORMATION: Mgat4aEx1gRNA

<400> SEQUENCE: 58
ggtataccac atggcaaaat ggg        23

<210> SEQ ID NO 59
<211> LENGTH: 23

```
<212> TYPE: DNA
<213> ORGANISM: Artificial Sequence
<220> FEATURE:
<223> OTHER INFORMATION: Mgat4aEx2gRNA

<400> SEQUENCE: 59
gtccaacagt tcgccgtgc agg                                              23

<210> SEQ ID NO 60
<211> LENGTH: 3873
<212> TYPE: DNA
<213> ORGANISM: Artificial Sequence
<220> FEATURE:
<223> OTHER INFORMATION: Shuttle vector

<400> SEQUENCE: 60
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt accaagcttg     420
gttgcatgct gtccggagtc tcagcgttat accagaagtg acctgggtcg gggaagacta     480
tagtgtcacc taaatctcta gagcccttca ttaggcgcgc caatcccatt gcaaattcta     540
caaaaggagt gtttcccaac tgctctatca agaggaatgt tgcacactgt gacctgaatg     600
caaacatcac acgcgccagc agagaggaag aagagaggct tccctgaccg ggaatcgaac     660
ccgggccgcg gcggtgagag cgccgaatcc taaccactag accaccaggg agcacgcgcc     720
aaagctcaat gagctataat tatccccttg gaaaacctac aaaaacagtg tttcaaaact     780
gctctgtgaa aagggacctt tgctagcacg cggcgccagg caaaacgtgg gcacgctgcg     840
ttggccggga tcgaacccg gtcaactgct tggaaggca gctatgctca ccactatacc      900
accaacgcgc acacgcgcca gcagattcta cgggaagagt gtttcaaaac tgctctatca     960
agagaaatgt tccaccttgt gtgtggaatg cagccatcac acgcgtccat gaaagggctt    1020
aattaagata tcgtttaaac gtcgacctgc agaggccggc ggataactag ctgatcgcgg    1080
aatcctgtcc ctaggccacc cactgtgggg tgcccttcat taggcgcgcc aatcccattg    1140
caaattctac aaaaggagtg tttcccaact gctctatcaa gaggaatgtt gcacactgtg    1200
acctgaatgc aaacatcaca cgcgccagca gagaggaaga agagaggctt ccctgaccgg    1260
gaatcgaacc cggccgcgg cggtgagagc gccgaatcct aaccactaga ccaccaggga    1320
gcacgcgcca aagctcaatg agctataatt atcccttgg aaaacctaca aaaacagtgt    1380
ttcaaaactg ctctgtgaaa agggaccttt gctagcacgc ggcgccaggc aaaacgtggg    1440
cacgctgcgt tggccgggaa tcgaacccgg tcaactgctt ggaaggcag ctatgctcac     1500 cactatacca ccaacgcgca cacgcgccag cagattctac gggaagagtg tttcaaaact    1560
gctctatcaa gagaaatgtt ccaccttgtg tgtggaatgc agccatcaca cgcgtccatg    1620
aaagggcggt tgcatgctgt ccggagtctc agcgttatac cagaagtgac ctgggtcggg    1680
gaagaaaagc ttcatggtca tagctgtttc ctgtgtgaaa ttgttatccg ctcacaattc    1740
cacacaacat acgagccgga agcataaagt gtaaagcctg gggtgcctaa tgagtgagct    1800
```

```
aactcacatt aattgcgttg cgctcactgc ccgctttcca gtcgggaaac ctgtcgtgcc   1860
agctgcatta atgaatcggc caacgcgcgg ggagaggcgg tttgcgtatt gggcgctctt   1920
ccgcttcctc gctcactgac tcgctgcgct cggtcgttcg gctgcggcga gcggtatcag   1980
ctcactcaaa ggcggtaata cggttatcca cagaatcagg ggataacgca ggaaagaaca   2040
tgtgagcaaa aggccagcaa aaggccagga accgtaaaaa ggccgcgttg ctggcgtttt   2100
tccataggct ccgcccccct gacgagcatc acaaaaatcg acgctcaagt cagaggtggc   2160
gaaacccgac aggactataa agataccagg cgtttccccc tggaagctcc ctcgtgcgct   2220
ctcctgttcc gaccctgccg cttaccggat acctgtccgc ctttctccct tcgggaagcg   2280
tggcgctttc tcatagctca cgctgtaggt atctcagttc ggtgtaggtc gttcgctcca   2340
agctgggctg tgtgcacgaa ccccccgttc agcccgaccg ctgcgcctta tccggtaact   2400
atcgtcttga gtccaacccg gtaagacacg acttatcgcc actggcagca gccactggta   2460
acaggattag cagagcgagg tatgtaggcg gtgctacaga gttcttgaag tggtggccta   2520
actacggcta cactagaaga acagtatttg gtatctgcgc tctgctgaag ccagttacct   2580
tcggaaaaag agttggtagc tcttgatccg gcaaacaaac caccgctggt agcggtggtt   2640
tttttgtttg caagcagcag attacgcgca gaaaaaaagg atctcaagaa gatcctttga   2700
tcttttctac ggggtctgac gctcagtgga acgaaaactc acgttaaggg attttggtca   2760
tgagattatc aaaaaggatc ttcacctaga tccttttaaa ttaaaaatga agttttaaat   2820
caatctaaag tatatatgag taaacttggt ctgacagtta gaaaaactca tcgagcatca   2880
aatgaaactg caatttattc atatcaggat tatcaatacc atatttttga aaaagccgtt   2940
tctgtaatga aggagaaaac tcaccgaggc agttccatag gatggcaaga tcctggtatc   3000
ggtctgcgat tccgactcgt ccaacatcaa tacaacctat taatttcccc tcgtcaaaaa   3060
taaggttatc aagtgagaaa tcaccatgag tgacgactga atccggtgag aatggcaaaa   3120
gtttatgcat ttctttccag acttgttcaa caggccagcc attacgctcg tcatcaaaat   3180
cactcgcatc aaccaaaccg ttattcattc gtgattgcgc ctgagcgaga cgaaatacgc   3240
gatcgctgtt aaaaggacaa ttacaaacag gaatcgaatg caaccggcgc aggaacactg   3300
ccagcgcatc aacaatattt tcacctgaat caggatattc ttctaatacc tggaatgctg   3360
ttttcccagg gatcgcagtg gtgagtaacc atgcatcatc aggagtacgg ataaaatgct   3420
tgatggtcgg aagaggcata aattccgtca gccagtttag tctgaccatc tcatctgtaa   3480
catcattggc aacgctacct ttgccatgtt tcagaaacaa ctctggcgca tcgggcttcc   3540
catacaatcg atagattgtc gcacctgatt gcccgacatt atcgcgagcc catttatacc   3600
catataaatc agcatccatg ttggaattta atcgcggcct agagcaagac gtttcccgtt   3660
gaatatggct catactcttc cttttcaat attattgaag catttatcag ggttattgtc   3720
tcatgagcgg atacatattt gaatgtattt agaaaaataa acaaataggg gttccgcgca   3780
catttccccg aaaagtgcca cctgacgtct aagaaaccat tattatcatg acattaacct   3840
ataaaaatag gcgtatcacg aggccctttc gtc                               3873
```

<210> SEQ ID NO 61
<211> LENGTH: 50
<212> TYPE: DNA
<213> ORGANISM: Artificial Sequence
<220> FEATURE:
<223> OTHER INFORMATION: mgat2-allel

<400> SEQUENCE: 61
tcctttgtcg cccattgctg ctccgacgaa gccgcaggcg gccaccacga        50

<210> SEQ ID NO 62
<211> LENGTH: 68
<212> TYPE: DNA
<213> ORGANISM: Artificial Sequence
<220> FEATURE:
<223> OTHER INFORMATION: mgat5-alle1

<400> SEQUENCE: 62 ggggatgat gcttctgcac ttcaccatcc agcagccagc ggactcagcc tgagagcagc        60
tccatgtt        68

<210> SEQ ID NO 63
<211> LENGTH: 60
<212> TYPE: DNA
<213> ORGANISM: Artificial Sequence
<220> FEATURE:
<223> OTHER INFORMATION: mgat5-alle2

<400> SEQUENCE: 63
gggggatgat gcttctgcac ttcaccatcc agggactcag cctgagagca gctccatgtt        60

<210> SEQ ID NO 64
<211> LENGTH: 48
<212> TYPE: DNA
<213> ORGANISM: Artificial Sequence
<220> FEATURE:
<223> OTHER INFORMATION: mgat5-alle3

<400> SEQUENCE: 64
gggggatgat gcttctgcac ttcctcagcc tgagagcagc tccatgtt        48

<210> SEQ ID NO 65
<211> LENGTH: 32
<212> TYPE: DNA
<213> ORGANISM: Artificial Sequence
<220> FEATURE:
<223> OTHER INFORMATION: B4galt2-alle1

<400> SEQUENCE: 65
cagccccgcc accgccatgg acaagtttgg ct        32

<210> SEQ ID NO 66
<211> LENGTH: 26
<212> TYPE: DNA
<213> ORGANISM: Artificial Sequence
<220> FEATURE:
<223> OTHER INFORMATION: B4galt2-alle2

<400> SEQUENCE: 66
cagccccgcc atggacaagt ttggct        26

<210> SEQ ID NO 67
<211> LENGTH: 39
<212> TYPE: DNA
<213> ORGANISM: Artificial Sequence
<220> FEATURE:
<223> OTHER INFORMATION: st3Gal4-alle1

<400> SEQUENCE: 67
ggcagcctcc agtgtcgtcg gttgtggtgg ggaatgggc        39

<210> SEQ ID NO 68

```
<211> LENGTH: 38
<212> TYPE: DNA
<213> ORGANISM: Artificial Sequence
<220> FEATURE:
<223> OTHER INFORMATION: st3Gal4-alle1

<400> SEQUENCE: 68
ggcagcctcc agtgtcgtcg ttgtggtggg gaatgggc                                38

<210> SEQ ID NO 69
<211> LENGTH: 48
<212> TYPE: DNA
<213> ORGANISM: Artificial Sequence
<220> FEATURE:
<223> OTHER INFORMATION: st3Gal4-alle2

<400> SEQUENCE: 69
ggcagcctcc agtgtcgtcg acacgttgtg ttgtggtggg gaatgggc                     48

<210> SEQ ID NO 70
<211> LENGTH: 40
<212> TYPE: DNA
<213> ORGANISM: Artificial Sequence
<220> FEATURE:
<223> OTHER INFORMATION: st3Gal6-alle1

<400> SEQUENCE: 70
cggtacctct gattttgctt ttgccctatg ggacaaggcc                              40

<210> SEQ ID NO 71
<211> LENGTH: 37
<212> TYPE: DNA
<213> ORGANISM: Artificial Sequence
<220> FEATURE:
<223> OTHER INFORMATION: st3Gal6-alle2

<400> SEQUENCE: 71
cggtacctct gattttgctt tgctatggga caaggcc                                 37

<210> SEQ ID NO 72
<211> LENGTH: 32
<212> TYPE: DNA
<213> ORGANISM: Artificial Sequence
<220> FEATURE:
<223> OTHER INFORMATION: st3Gal6-alle2

<400> SEQUENCE: 72
cggtacctct gattttgcta tgggacaagg cc                                      32

<210> SEQ ID NO 73
<211> LENGTH: 37
<212> TYPE: DNA
<213> ORGANISM: Artificial Sequence
<220> FEATURE:
<223> OTHER INFORMATION: B3gnt2-alle1

<400> SEQUENCE: 73 ttcagcccctt cccccgggcg tactggaaca gagagca                                37

<210> SEQ ID NO 74
<211> LENGTH: 36
<212> TYPE: DNA
<213> ORGANISM: Artificial Sequence
<220> FEATURE:
<223> OTHER INFORMATION: B3gnt2-alle2

<400> SEQUENCE: 74
```

```
                                  -continued ttcagcccttt ccccgggcgt actggaacag agagca                      36

<210> SEQ ID NO 75
<211> LENGTH: 53
<212> TYPE: DNA
<213> ORGANISM: Artificial Sequence
<220> FEATURE:
<223> OTHER INFORMATION: B3gnt8-WT

<400> SEQUENCE: 75
tggtccagag atagctaatg aagcttctag ggtggagaag ctggggctgc tga    53

<210> SEQ ID NO 76
<211> LENGTH: 36
<212> TYPE: DNA
<213> ORGANISM: Artificial Sequence
<220> FEATURE:
<223> OTHER INFORMATION: B3gnt8-alle1

<400> SEQUENCE: 76
tggtccagag gagggtggag aagctggggc tgctga                       36

<210> SEQ ID NO 77
<211> LENGTH: 36
<212> TYPE: DNA
<213> ORGANISM: Artificial Sequence
<220> FEATURE:
<223> OTHER INFORMATION: fut8-alle1

<400> SEQUENCE: 77
caaatacttg atccgtccac aaggctggaa agggaa                       36

<210> SEQ ID NO 78
<211> LENGTH: 50
<212> TYPE: DNA
<213> ORGANISM: Artificial Sequence
<220> FEATURE:
<223> OTHER INFORMATION: mgat2-alle1

<400> SEQUENCE: 78
tcctttgtcg cccattgctg ctccagcgaa gccgcaggcg gccaccacga        50
```